US012611284B2

(12) United States Patent
Christianson et al.

(10) Patent No.: US 12,611,284 B2
(45) Date of Patent: Apr. 28, 2026

(54) SURGICAL EYEWEAR LIGHTING SYSTEMS AND METHODS

(71) Applicants: Hawkeye Surgical Lighting Inc., Coralville, IA (US); University of Iowa Research Foundation, Iowa City, IA (US)

(72) Inventors: David Christianson, Coralville, IA (US); Jeffrey F. Haynes, Clifton, VA (US)

(73) Assignees: Hawkeye Surgical Lighting, Inc., Coralville, IA (US); University of Iowa Research Foundation, Iowa City, IA (US)

( * ) Notice: Subject to any disclaimer, the term of this patent is extended or adjusted under 35 U.S.C. 154(b) by 301 days.

(21) Appl. No.: 18/087,154

(22) Filed: Dec. 22, 2022

(65) Prior Publication Data

US 2023/0277273 A1     Sep. 7, 2023

Related U.S. Application Data

(60) Provisional application No. 63/294,744, filed on Dec. 29, 2021.

(51) Int. Cl.
  *A61B 90/30*        (2016.01)
  *F21L 4/02*         (2006.01)
       (Continued)

(52) U.S. Cl.
  CPC .............. *A61B 90/30* (2016.02); *F21L 4/027* (2013.01); *F21V 23/0414* (2013.01);
       (Continued)

(58) Field of Classification Search
  CPC ..... A61B 90/30; F21V 29/508; F21V 29/773; F21V 23/0414; F21V 23/0457; F21V 23/0492; F21L 4/027
  See application file for complete search history.

(56) References Cited

U.S. PATENT DOCUMENTS 5,667,291 A      9/1997  Caplan et al.
7,828,465 B2 *  11/2010  Roberge .................. F21V 29/80
                                                          362/147
                   (Continued)

FOREIGN PATENT DOCUMENTS

CN        111557750 A      8/2020
DE    102010023242 A1 *  12/2011   .............. F21V 29/70
                   (Continued)

OTHER PUBLICATIONS

Van Dyke, Lucas , "Surgical Headlamp", Online: Coroflot.com, 2011.

*Primary Examiner* — Abdulmajeed Aziz
*Assistant Examiner* — Jessica M Apenteng
(74) *Attorney, Agent, or Firm* — Dentons Davis Brown, P.C.; Matthew Warner-Blankenship

(57)          ABSTRACT

The present application discloses a surgical lamp. The surgical lamp includes a light source, a housing, and a heat sink into which heat from the light source is transferred. The housing includes a thermal insulating shell substantially surrounding the heat sink, and a plurality of ports that enable to airflow to dissipate the heat transferred to the heat sink.

24 Claims, 45 Drawing Sheets

(51) Int. Cl.

| | |
|---|---|
| *F21V 23/04* | (2006.01) |
| *F21V 29/508* | (2015.01) |
| *F21V 29/77* | (2015.01) |
| *F21W 131/20* | (2006.01) |
| *F21Y 113/13* | (2016.01) |
| *F21Y 115/10* | (2016.01) |
| *G02C 11/04* | (2006.01) |

(52) U.S. Cl.

CPC ...... *F21V 23/0457* (2013.01); *F21V 23/0492* (2013.01); *F21V 29/508* (2015.01); *F21V 29/773* (2015.01); *G02C 11/04* (2013.01); *F21W 2131/20* (2013.01); *F21Y 2113/13* (2016.08); *F21Y 2115/10* (2016.08)

(56) References Cited

U.S. PATENT DOCUMENTS

| | | | | |
|---|---|---|---|---|
| 8,152,330 | B2 * | 4/2012 | Waters | F21V 21/0885 |
| | | | | 351/158 |
| 9,249,964 | B2 * | 2/2016 | Hansen | F21V 29/507 |
| 9,562,672 | B2 * | 2/2017 | Jørgensen | F21V 29/50 |
| 10,344,960 | B2 | 7/2019 | Boesen | |
| 10,620,460 | B2 | 4/2020 | Carabin | |
| 10,620,913 | B2 * | 4/2020 | Beatty | F21V 3/02 |
| 10,708,990 | B1 | 7/2020 | Ferguson | |
| 10,842,002 | B2 | 11/2020 | Chang | |
| 11,112,102 | B2 * | 9/2021 | Pan | H05B 47/105 |
| 11,119,309 | B1 | 9/2021 | Feinbloom et al. | |
| 2010/0060132 | A1 * | 3/2010 | Liu | F21V 29/74 |
| | | | | 313/46 |
| 2011/0050124 | A1 * | 3/2011 | Bailey | F21K 9/23 |
| | | | | 313/46 |
| 2012/0120636 | A1 | 5/2012 | Wilt et al. | |
| 2017/0231058 | A1 * | 8/2017 | Sadwick | H05B 47/19 |
| 2021/0306599 | A1 | 9/2021 | Pierce | |
| 2021/0307145 | A1 | 9/2021 | Oelgarth et al. | |
| 2021/0341131 | A1 * | 11/2021 | Plash, IV | F21V 15/01 |
| 2021/0352442 | A1 | 11/2021 | Baker et al. | |

FOREIGN PATENT DOCUMENTS

| | | | |
|---|---|---|---|
| TW | 607434 U | * | 2/2021 |
| TW | M607434 | | 2/2021 |

* cited by examiner

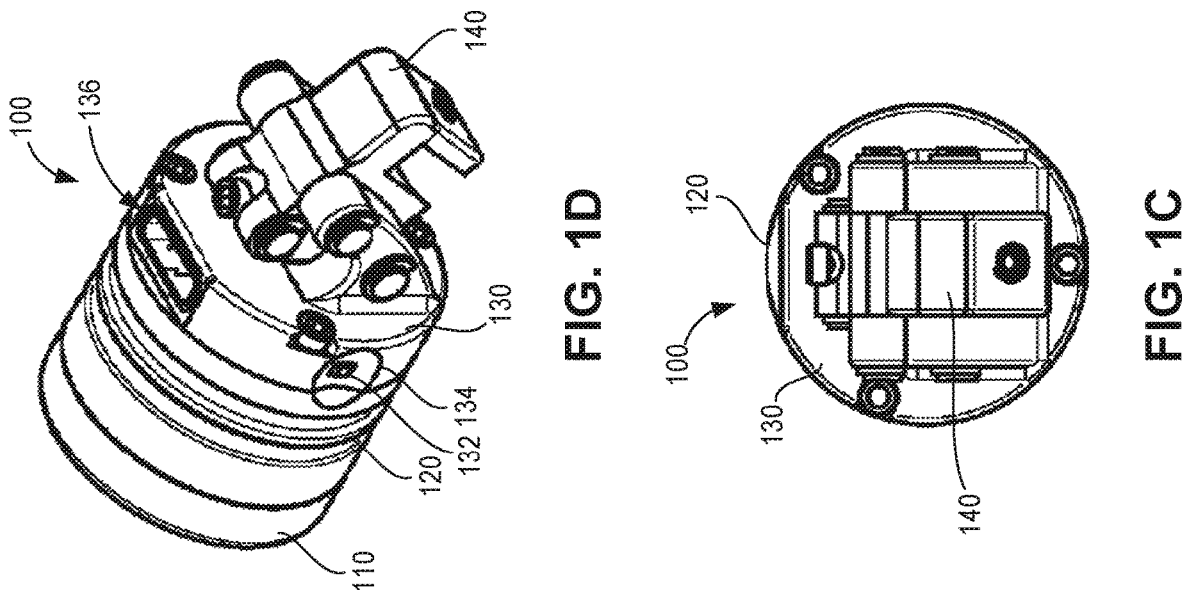
FIG. 1D
FIG. 1C
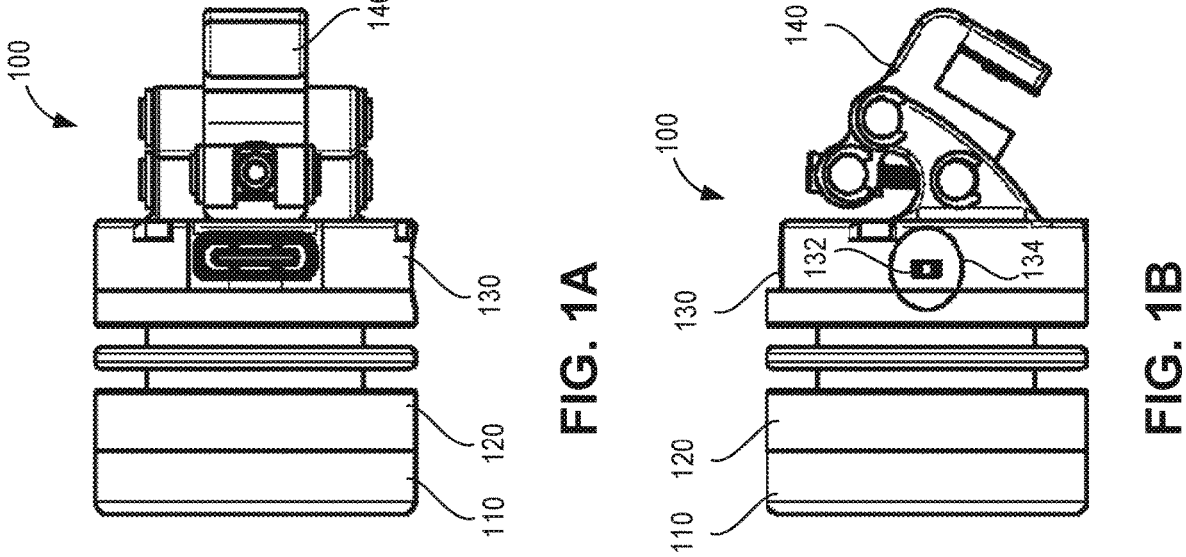
FIG. 1A
FIG. 1B

Top hinge pin
Middle hinge pin
Bottom hinge pin
178
174
172
176
100
Light body
LED star
Lens
Bezel
114
112
110
120
150
136
138
PCB
130
Rear cap
116
161
162
164
163
166
165
140
117
Glasses bracket
Glasses set screw
145

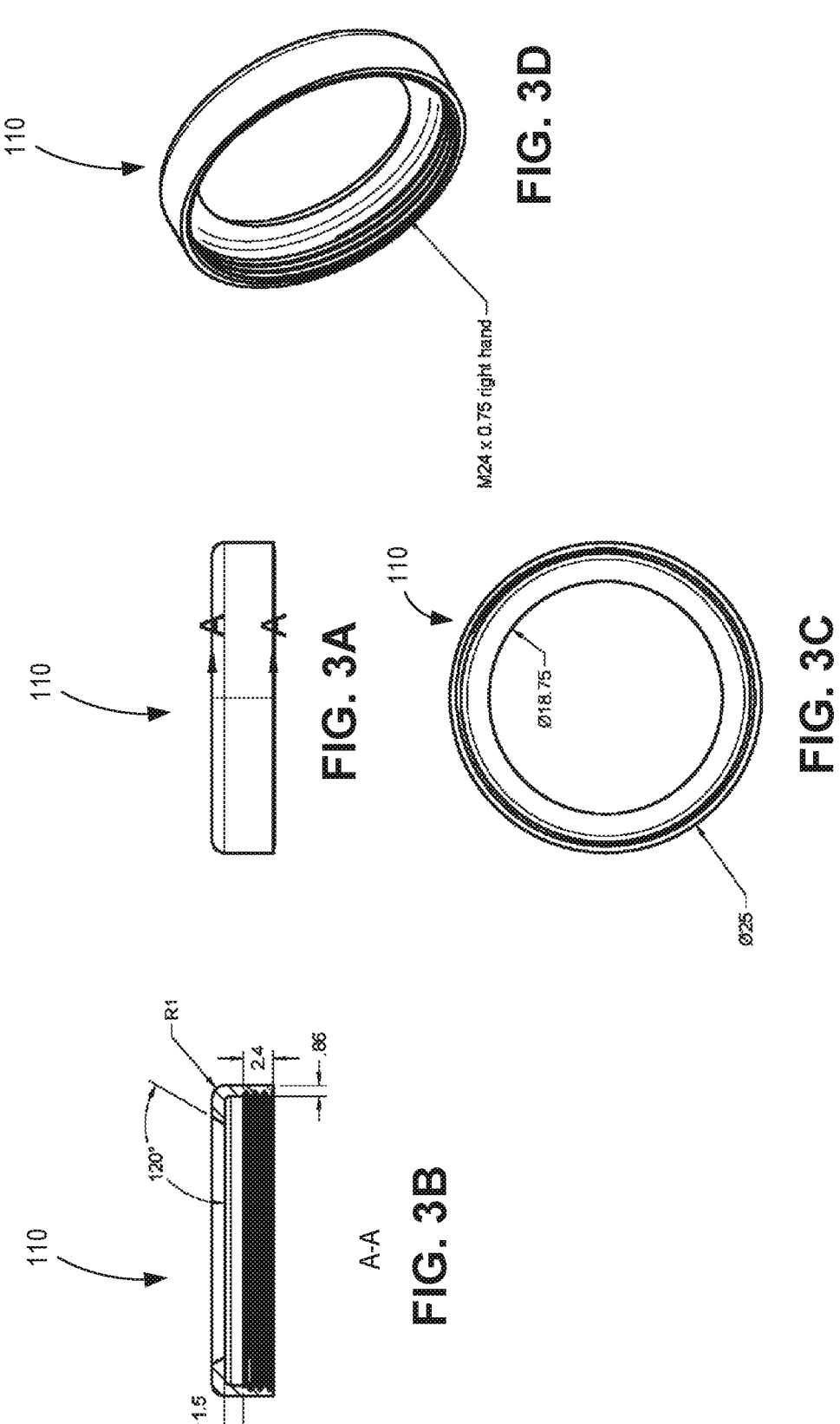

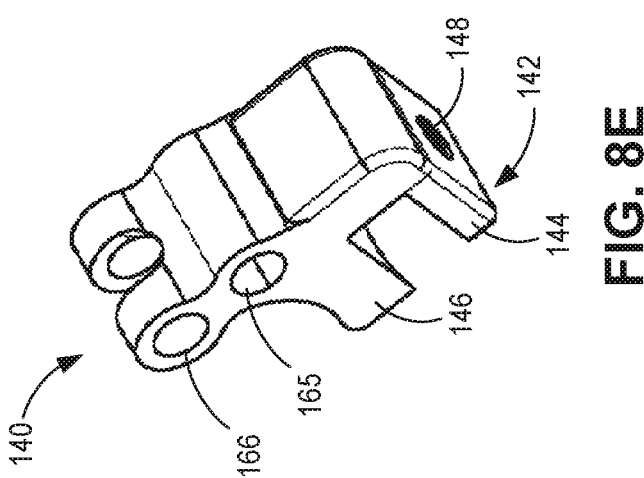
FIG. 8E
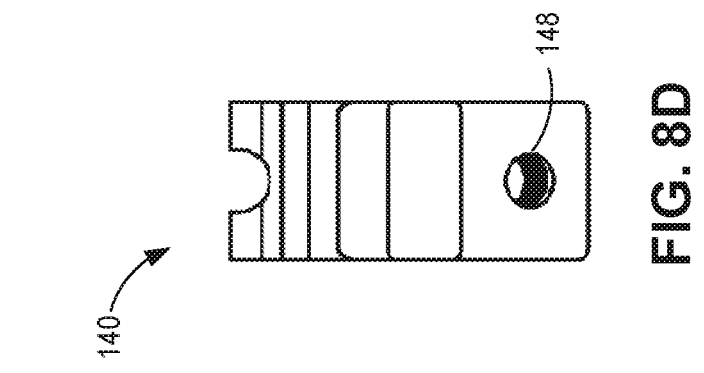
FIG. 8D
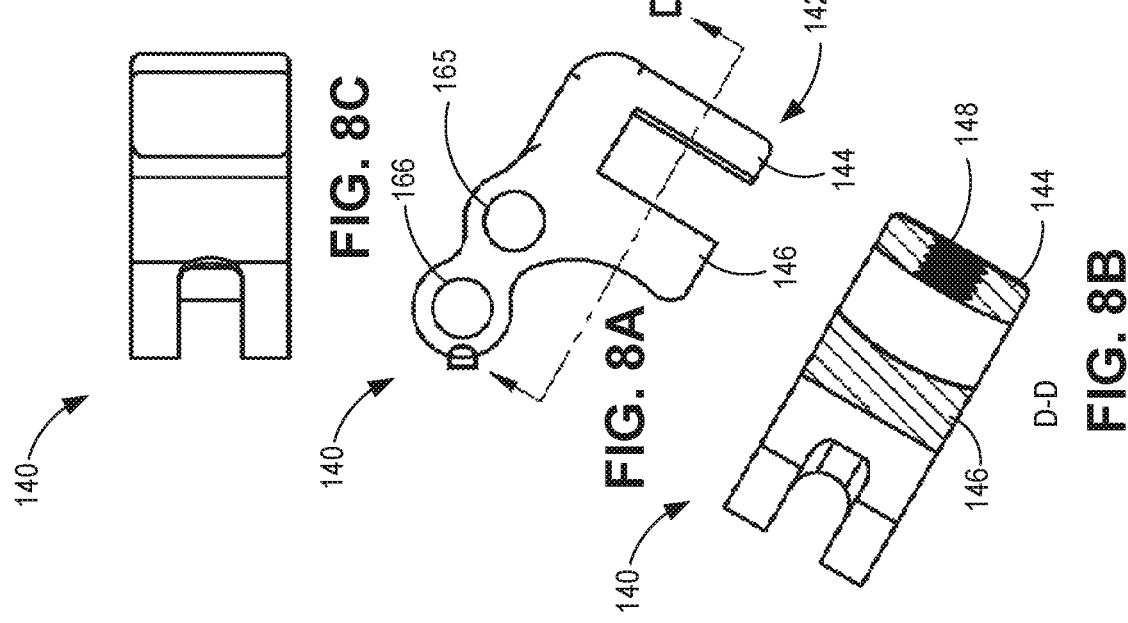
FIG. 8C
FIG. 8A
FIG. 8B

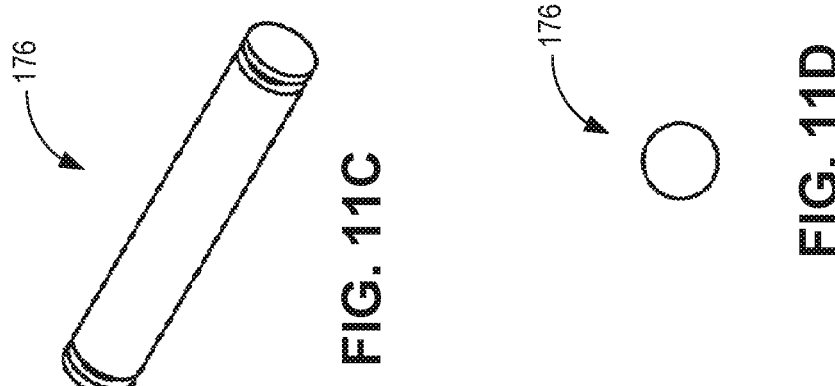
FIG. 11C
FIG. 11D
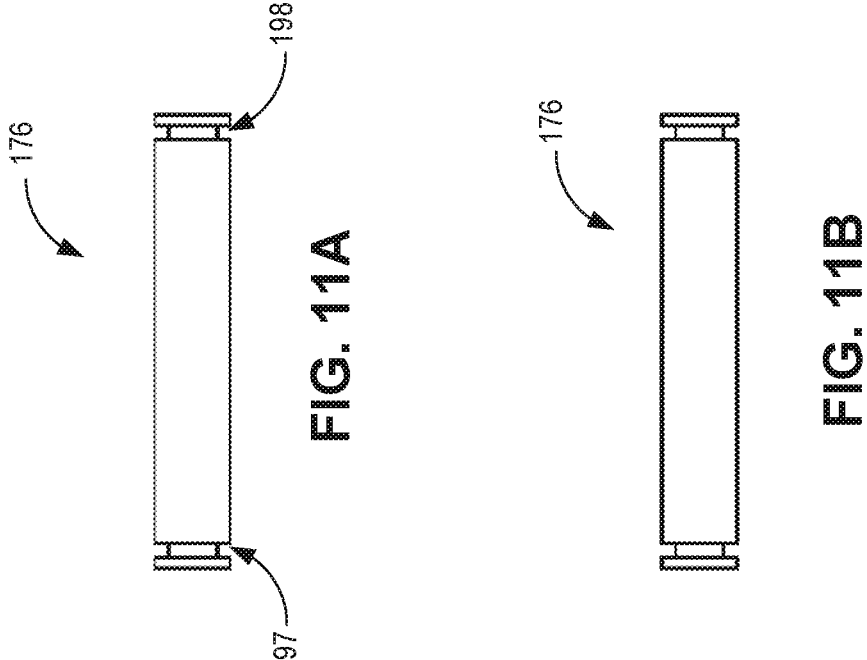
FIG. 11A
FIG. 11B

514

554

510                  512

2230

2250

2270

2200

2260

2218

2214

2212

2210

2230

2250

2262

2263

2264

2210

2216

2210

2300

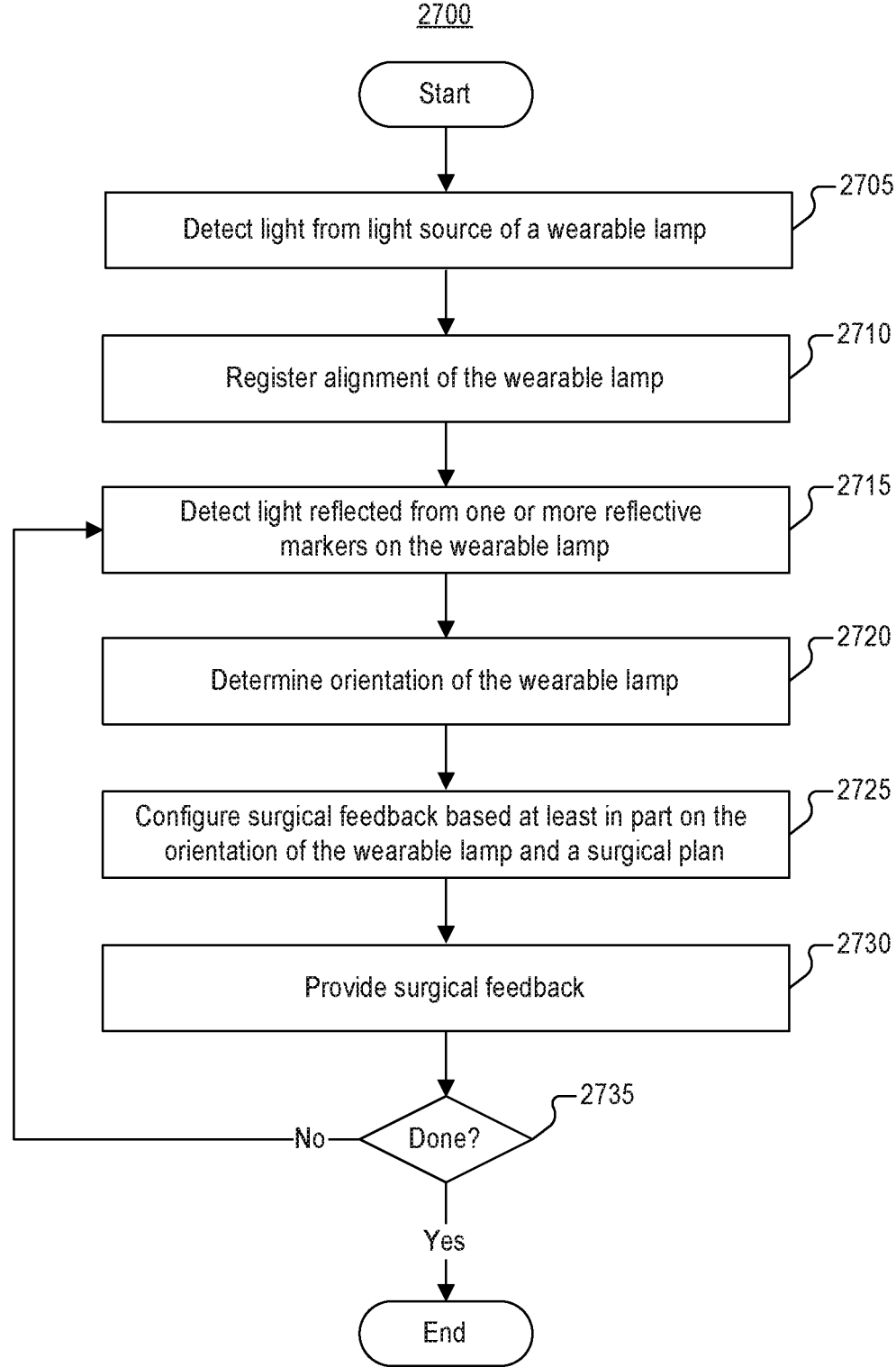

2700

Start

Detect light from light source of a wearable lamp  —2705

Register alignment of the wearable lamp  —2710

Detect light reflected from one or more reflective markers on the wearable lamp  —2715

Determine orientation of the wearable lamp  —2720

Configure surgical feedback based at least in part on the orientation of the wearable lamp and a surgical plan  —2725

Provide surgical feedback  —2730

Done?  —2735

No

Yes

End

FIG. 27

SURGICAL EYEWEAR LIGHTING SYSTEMS AND METHODS

CROSS REFERENCE TO OTHER APPLICATIONS

This application claims priority to U.S. Provisional Patent Application No. 63/294,744 entitled SURGICAL EYEWEAR LIGHTING SYSTEMS AND METHODS filed Dec. 29, 2021 which is incorporated herein by reference for all purposes.

TECHNICAL FIELD

The present disclosure relates to surgical lighting systems, and in particular to surgical eyewear lighting systems.

BACKGROUND OF THE INVENTION

Wearable lamps have become popular for contexts in which hands-free use of the lamp is desired. Examples of such contexts are surgical interventions, and dental applications. Hands-free contexts such as surgical or dental applications generally require a human user to engage the patient with fine precision. Thus, adequately illuminating the field of view is an important consideration when selecting a wearable lamp. Dentists and other care providers such as surgeons, doctors, and other professionals may also use loupes. Loupes are magnifying devices that a care provider may wear to improve his or her ability to accurately view the surgical area, such as for example, a patient's anatomy. Some lamps are configured to be fitted on loupes so that the field of view of the surgical site is illuminated and magnified suitably throughout the surgical intervention.

BRIEF DESCRIPTION OF THE DRAWINGS

Various embodiments of the invention are disclosed in the following detailed description and the accompanying drawings.

FIGS. 1A, 1B, 1C, and 1D illustrate top, side, rear, and perspective views, respectively, of a surgical light of the present disclosure, in accordance with various embodiments.

FIGS. 3A, 3B, 3C, and 3D illustrate top, section, rear, and perspective views, respectively, of a bezel for a surgical light of the present disclosure, in accordance with various embodiments.

FIGS. 8A, 8B, 8C, 8D, and 8E illustrate side, section, top, rear, and perspective views, respectively, of a glasses bracket of a surgical light of the present disclosure, in accordance with various embodiments.

FIGS. 11A, 11B, 11C, and 11D illustrate top, front, perspective, and side views, respectively, of a middle hinge pin of a surgical light of the present disclosure, in accordance with various embodiments.

FIG. 27 illustrates a flow diagram of a method for providing surgical feedback based at least in part on an orientation of a wearable lamp according to various embodiments.

DETAILED DESCRIPTION

Figure 2A:
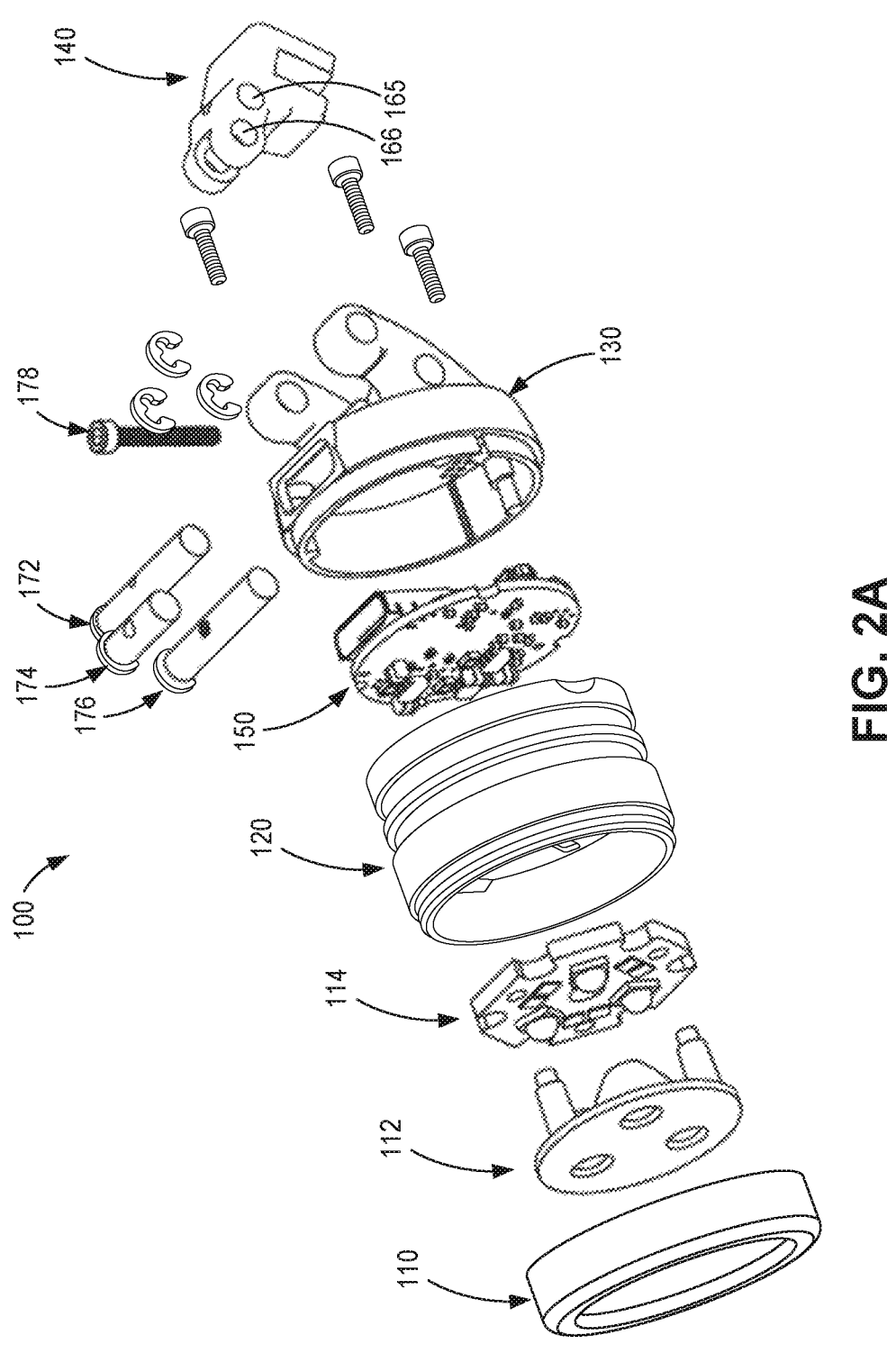
FIGS. 2A and 2B illustrate assembly views of a surgical light of the present disclosure, in accordance with various embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

For the sake of brevity, conventional techniques and components for wearable surgical lighting systems may not be described in detail herein. Furthermore, the connecting lines shown in various figures contained herein are intended to represent exemplary functional relationships and/or physical couplings between various elements. It should be noted that many alternative or additional functional relationships or physical connections may be present in exemplary passive exoskeleton systems and/or components thereof.

A problem that all practitioners that perform interventions upon patients encounter daily is that of adequate lighting for visualization of the surgical site or sites. Focused and directed lighting is even more important and difficult to achieve in delicate, microsurgical interventions that require telescopic magnification of the surgical field as the targets are often smaller and deeper within a wound. In much the same way that a deep valley receives the smallest portion of daily sunlight, these deep wounds are very challenging to illuminate with overhead lighting in the operating room (OR) as the surgeon's head and line of sight are often in common with the light source overhead causing considerable shadowing of the field. This problem has typically been addressed with a head mounted lighting system that, after being secured to the forehead, appropriately plugged in and powered, adjusted and directed, projects focused light into the field of view of the surgeon. The light projected has typically been supplied by a light source in a separate box and conveyed to the surgeon by a fiber optic cable. The light source is typically similar in size to a lunchbox, and is typically mounted on a stand and plugged into a wall receptacle for power. The light source is typically generated by a Xenon or halogen bulb which is housed in the roll around box that is positioned behind the surgeon. The bulb makes considerable heat in producing the light which is dissipated actively by a fan within the light box.

While Xenon or halogen bulb the light source is effective in illuminating the surgical target, there are many challenges associated with this type of device: the light is attached to the head through a clamping type of headband. The clamping portion is uncomfortable. The headband and associated light are heavy and cause considerable muscle fatigue during long procedures which serve as a distraction to the surgeon. The considerable surface area of the band also commonly becomes warm. The surgeon is tethered to a box that is connected to a receptacle—this requires an additional person to disconnect the surgeon and follow them wherever they go in the OR and to reconnect them, often to a different light source if the surgeon needs to relocate (such as to move to the other side of the patient). The headlight must be manually adjusted to align the light with the surgeon's field of view every time that it is donned. This tends to be a problem once the surgeon is "scrubbed in" and sterile as she or he may no longer touch the device and is again reliant upon a helper in the OR to carefully adjust the light until it is focused and directed correctly. This step is often time consuming and is a point of increased risk for surgical contamination as the assistant works directly in front of the surgeon's sterile field. Another shortcoming of this design is that the light is not easily dimmable. Further, the light can temporarily disturb the vision of others in the room when the surgeon looks away from the surgical field as it can inadvertently be directed into the eyes of others without the surgeon being aware. Further, the quality of the light source degrades over time because wear and tear on the fiberoptic cable that connects the headlight to the source slowly degrades as fibers break.

These challenges to proper operation serve to reduce the overall number of times that a surgeon will elect to use a traditional headlight. The surgeon may tend to elect to operate with suboptimal lighting for certain parts of a procedure because the time and inconvenience is too great. One example window of a procedure that most surgeons will not go through the process of replacing a headlight is as follows: During many microsurgical procedures, the approach to the surgical target will be performed with operative telescopes, or loupes, and a headlight until the target is appropriately exposed. At this time, the surgeon will often bring a large surgical microscope that is equipped with its own lighting system into the field and remove their loupes and headlight. Once the portion of the procedure requiring the microscope is complete, the surgeon often elects to remove the microscope from the field and have their loupes replaced but will not go through the additional struggle of replacing the headlamp due to the above-described challenges of appropriately focusing and directing the light as well as added risk of contamination. As a result, the latter portion of microscope-based procedures are often completed without the benefit of a headlight which degrades the quality of the procedure completion.

Over the last decade, significant advances have been made in light emitting diode (LED) and lithium ion/lithium polymer battery technologies which has led to the ability to make very bright light with a very small and lightweight footprint, with significantly less heat production, that are powered by batteries rather than typical power receptacles. These LEDs have been adopted into similar headlights as described above. These devices have advertised LUX performance of ~200,000 LUX at ~13" working distance which is similar in performance to the earlier "tethered" designs. They have successfully removed the roll around light box and reliance upon wall receptacles and replaced them with battery power supplies that are typically mounted on the surgeon. While the light box/tethering problem has largely been solved by this innovation, the remaining problems outlined remain and a few new challenges have been introduced. One new challenge is that supplying the same amount of light as the wall receptacle powered devices requires significant battery storage solutions, which adds to the weight of equipment worn by the surgeon and increases fatigue. Due to this constraint, the need for ever more efficient light sources is still needed to make the lights as functional as possible without intruding on the user in ways that detract from their ability to focus solely on the task at hand. A problem which remains from the previous designs but is slightly different with cordless LED headlight technology is the surgeon's reliance on another person to make it functional during the surgery. While LED lighting with battery power supply allows the surgeon freedom to move around the OR without tethers, most designs require assistance to safely adjust the brightness, turn on or off, and disconnect, change batteries, etc.

There are certain types of surgeons, particularly in the fields of otolaryngology and plastic surgery, that require focused surgical illumination that can readily be made brighter and dimmer during the course of a procedure. In attempts to solve this problem, some surgeons place the dimming controller (if the particular light has a dimmer) under their surgical gown but within reach so that they can adjust the light through the gown by grasping and turning a dial or pressing a button. Unfortunately, the battery and light controller, which is typically a single unit, is designed to clip to one's waist, which is outside of the accepted sterile field of the surgeon. As a result, the line of good sterility can become blurred in order for the surgeon to be able to change the light intensity during surgery. Other lights have no dimming functionality or have brightness controls in a location that only an assistant can access (which can increase risk of contamination). Finally, the cord that powers the light can be very annoying to the surgeon is it is not successfully routed from the front of the head to the back of the neck in a way that avoids the ear and doesn't shift considerably during changes in head position as this is very distracting.

Typically, and before scrubbing ones hands in preparation for surgery, a surgeon turns on their light, ensures that it is directed appropriately and then leaves the light on while scrubbing and getting gowned, draping the patient, setting up OR equipment, going through time-out checkpoints, etc. before it is actually needed. This is typically done to simplify the process and not require assistance from a non-sterile person to turn it on and incur additional risk of contamination. This need to turn the light on before scrubbing can reduce the effective surgical time for the battery by as much as 30 minutes at the start. Further, there tends to be an increased waste of battery during surgery when the surgeon is looking away from the surgical field during which time the light is on but is not providing benefit to the procedure and can at times be a detriment by temporarily blinding other people in the room if the light is inadvertently directed towards them. Moreover, there tend to be very few ways to acceptably position the battery of the light source such that it can be controlled by the surgeon during surgery.

Another problem in the design of a surgical light source is that of exhausting heat. A surgical light source may have limited surface to radiate heat. If the surface area becomes too hot, it can create a burn hazard. While LEDs do not heat up as much as other conventional light sources, the use of an LED assembly may still cause the temperature of surrounding areas to increase, especially during medical operations that span hours.

Medical lighting of different colors can provide various benefits. Distinguishing various tissue types, assisting a color-blind surgeon or simple personal preference may cause a color blend that is optimal for a first surgeon, in a first situation, is not optimal for a second surgeon in a second situation.

A surgical light of the present disclosure solves these problems: It is lighter than other existing lights by about 25% (current~28 g, the disclosed~12-16 g). A surgical light of the present disclosure may be about 20% brighter than other existing lights and the illuminated area fills most surgeon's field of view (FOV) (not all telescopes have the same FOV) rather than only ~50% of it like other existing lights. In the brightest setting, a surgical light of the present disclosure may be slightly more than twice as bright as other existing lights. A single LED surgical light of the present disclosure may have a smaller area of illumination, which does not fill the surgeon's FOV, but which is about 250% brighter than existing surgical lights (at ~250,000 LUX). It tends to be difficult to compare advertised brightness of surgical lights because different companies measure brightness at different working distances. Because LUX decreases exponentially relative to distance, the claim of ~250,000 LUX by an existing company may be reported at a working distance that will probably not be viable for most/all surgeons. In contrast, a single LED surgical light of the present disclosure may have a brightness of ~250,000 LUX at a working distance which is viable for most/all surgeons.

Various embodiments include a wearable lamp. The wearable lamp may be a surgical lamp that is mountable to eyewear worn by a user. The wearable lamp is configured to provide at least 300 lumens and weighs less than 25 grams. In some embodiments, the wearable lamp is configured to provide between 350 and 600 lumens. In some embodiments, the wearable lamp weighs less than 20 grams. In some embodiments, the wearable lamp is configured to provide between 200,000 LUX and 300,000 LUX at 13 inches. In some embodiments, the wearable lamp is configured to provide 250,000 LUX at 13 inches with a spot size between 30 mm and 40 mm. For example, wearable lamp is configured to provide 250,000 LUX at 13 inches with a spot size of 33 mm. In some embodiments, the wearable lamp weighs less than 20 grams. As an example, the wearable lamp weighs 16.5 g. In some embodiments, the wearable lamp weighs less than 15 grams. In some embodiments, the wearable lamp weighs less than 10 grams. A wearable lamp may be a surgical lamp, a dental lamp, a recreational lamp, etc.

Various embodiments include a surgical lamp. The surgical lamp includes (i) a light source, (ii) a housing, and (iii) a heat sink into which heat from the light source is transferred. The housing includes a thermal insulating shell substantially surrounding the heat sink, and a plurality of ports that enable to airflow to dissipate the heat transferred to the heat sink.

Various embodiments include a wearable surgical lamp or dental lamp. The wearable surgical lamp includes (i) a light source, (ii) a housing, and (iii) a heat sink into which heat from the light source is transferred. In some embodiments, the wearable surgical lamp includes a plurality of pathways via which air flows from the heat sink to ports in the housing at the back of the wearable surgical lamp (e.g., a side closest to a surgeon's face). The plurality of pathways is configured to direct heat around a circuit board comprising a processor that drives the light source. In some embodiments, the wearable surgical lamp includes a thermally insulative spacer that is connected to the heat sink and is configured to provide spacing between the heat sink and the circuit board disposed at a rear of the heat sink. The thermally insulative spacer is configured to direct air dissipating from the heat sink to an outside of the circuit board (e.g., around the circuit board), or through one or more through holes comprised in the circuit board.

A surgical light of the present disclosure may be powered by a portable power supply. For example, in various embodiments, any conventional USB power supply able to provide a suitable electric current (e.g., 2.5 A). A surgical light of the present disclosure may be designed to be powered by any of the commonly available USB battery charging banks.

A surgical light of the present disclosure may be able to be controlled by a motion sensor (e.g., an accelerometer) with user adjustable settings such that it will turn off, or reduce a brightness, automatically when the surgeons head is positioned away from the surgical site. In some embodiments, the surgical light comprises a processor (e.g., a microcontroller, a microprocessor, etc.) that adjusts the light source based on a tilt detected by the motion sensor (e.g., accelerometer). The accelerometer may also be used to turn the light on and off (e.g., using gestures). User settings can adjust the timing and degree of sensitivity to movement and when the accelerometer and associated processor determines that the light has not moved, even subtly, for a set amount of time, it may automatically turn off. Conversely, the accelerometer and processor can turn the light on when sensing motion and position consistent with predefined settings, such as user-entered settings. In various embodiments, some of the settings controlling the functionality of a surgical light of the present disclosure may be adjusted by an integrated software (e.g., a phone app) that receives real time updates on brightness, position, and additional functionality. A surgical light of the present disclosure may independently drive three separate LEDs by microprocessor control. A surgical light of the present disclosure may be made brighter and dimmer, and change addressed LED light output by voice command. A surgical light of the present disclosure may provide auditory feedback that a command has been properly registered and executed through onboard amplifier.

In various embodiments, a surgical light of the present disclosure may also record voice memos during surgery that are saved through the phone app on the user's phone. The voice memos may also be saved in onboard memory within the surgical light. The voice memos may be converted to text by the surgical light or integrated software (e.g., a phone app) that receives the voice memos from the surgical light. In various embodiments, a surgical light of the present disclosure may also change settings on other devices in the room, for example that are addressed by Bluetooth low energy communication protocols. A surgical light of the present disclosure includes an adjustable attachment device (e.g., an adjustable clamp) for providing light down angle adjustment that is easy to adjust but very repeatable and does not require repeated adjustment after first time the light is mounted to the loupes.

FIG. 1A through FIG. 1D illustrate various views of a surgical light 100 of the present disclosure, in accordance with various embodiments. Surgical light 100 may include a bezel 110, a light body 120, a rear cap 130, and a bracket 140 (also referred to herein as a glasses bracket). Bezel 110, light body 120, and rear cap 130 may be generally coaxially aligned in the installed position. In various embodiments, bezel 110, light body 120, and rear cap 130 are made of thermally insulative material. For example, bezel 110 and/or rear cap 130 are plastic. As another example, light body 120 is plastic or a carbon fiber composite, etc. In various embodiments, an ON/OFF switch 132 may extend from rear cap 130. A dimple 134 may be formed in rear cap 130 to accommodate ON/OFF switch 132. In this manner, ON/OFF switch 132 may be disposed within the peripheral profile (e.g., see the round profile of surgical light 100 in FIG. 1C) while still allowing access to ON/OFF switch 132. Dimple 134 may be formed into both rear cap 130 and light body 120. Stated differently, rear cap 130 and light body 120 may define dimple 134.

Surgical light 100 further includes a power supply connector 136 for connecting a power supply to surgical light 100. Power supply connector 136 may be a USB (Universal Series Bus) connector. Power supply connector 136 may be a mini-USB connector, a micro-USB connector, a USB-C connector, or the like. Power supply connector 136 may generally comprise a metal casing, a plastic core member mounted in the metal casing, and a plurality of metal terminals bonded to the plastic core member. When in use, power supply connector 136 is bonded to a circuit board (i.e., see PCB 150 of FIG. 2A).

Figure 2B:
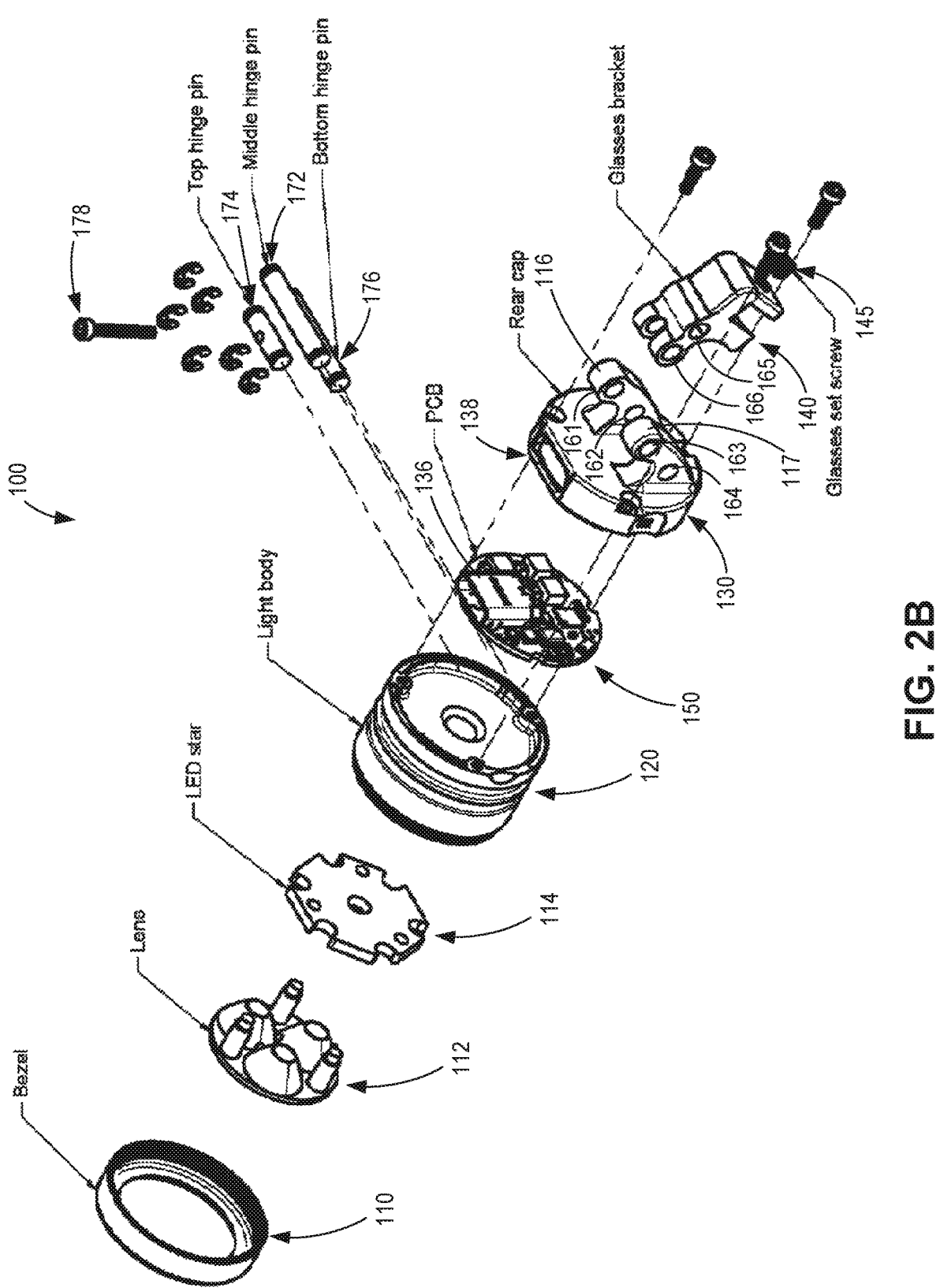
Figures 4A, 4B, 4C, 4D:
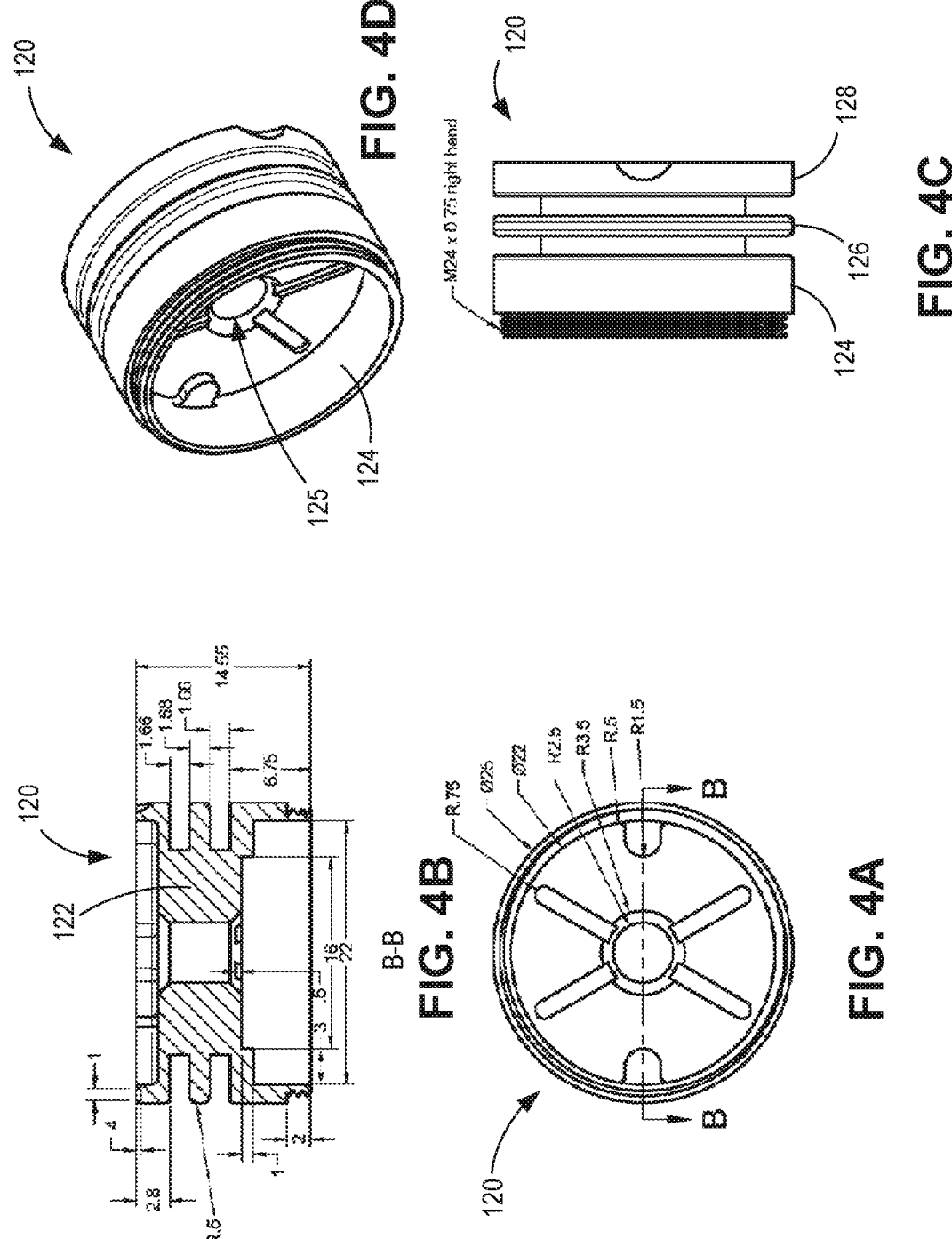
FIGS. 4A, 4B, 4C, 4D, 4E, 4F, 4G, and 4H illustrate front, section, side, front perspective, rear, section, side, and rear perspective views, respectively, of a light body of a surgical light, in accordance with various embodiments.
Figures 4E, 4F, 4G, 4H:
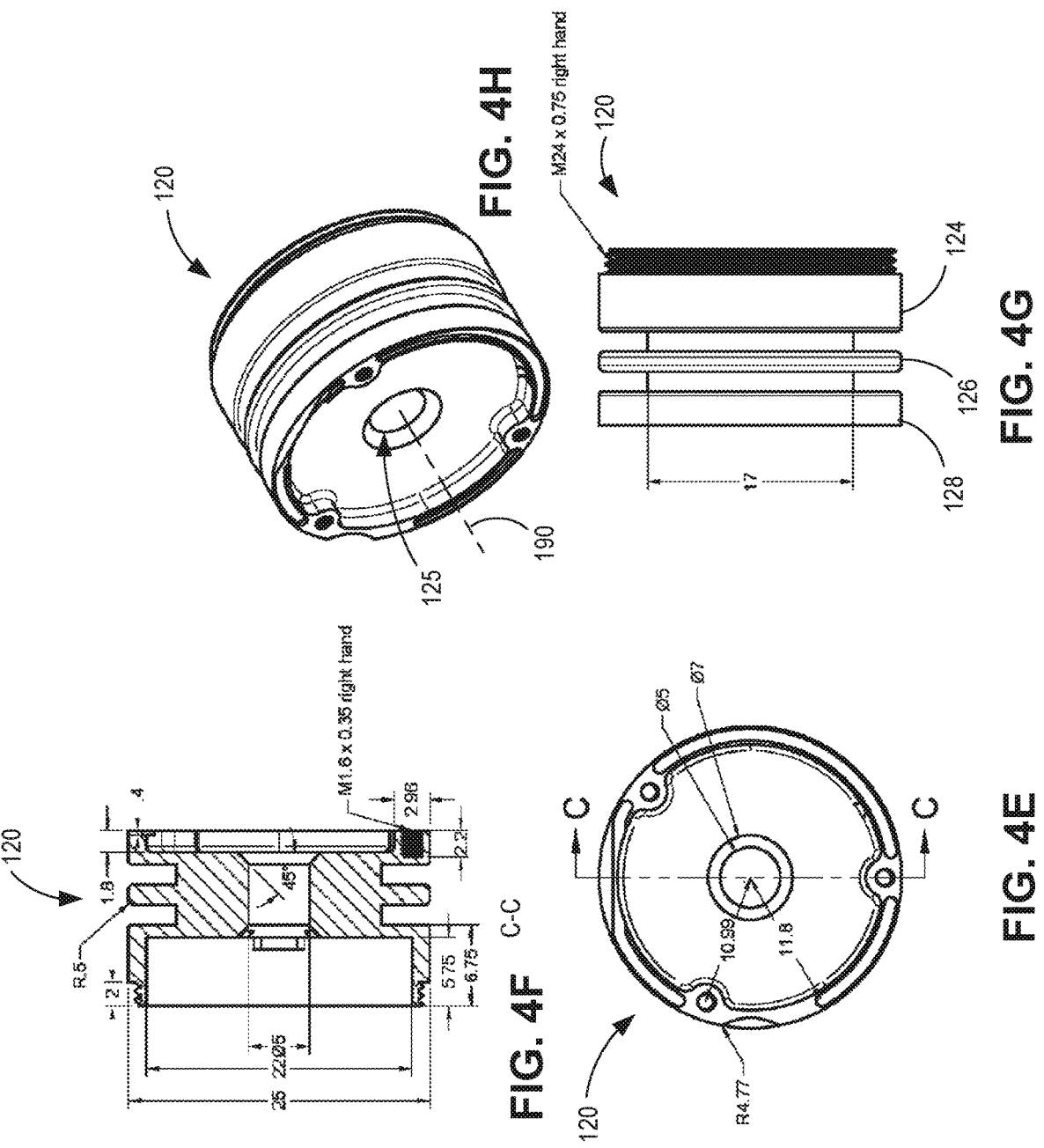

FIG. 2A and FIG. 2B illustrate assembly views of surgical light 100, in accordance with various embodiments. Surgical light 100 may further include a lens 112 for focusing light emitted from one or more LEDs (light emitting diodes) disposed on LED star 114. In this manner, LED star 114 may be disposed between lens 112 and light body 120. Lens 112 may be disposed between bezel 110 and LED star 114. Lens 112 may be made of polycarbonate. In various embodiments, a subset of two or more LEDs disposed on the LED store are configured to emit light of different wavelengths/color. For example, a first subset of one or more LEDs is configured to emit white light, and a second subset of the one or more LEDs is configured to emit UV light.

Surgical light 100 may further include a PCB 150. PCB 150 may be disposed between light body 120 and rear cap 130. Rear cap 130 may include an opening 138 for accommodating power supply connector 136.

Rear cap 130 may further include a first attachment bracket 116 and a second attachment bracket 117. Bracket 140 may be received between first attachment bracket 116 and a second attachment bracket 117. In various embodiments, first attachment bracket 116 includes a first aperture 161 and a second aperture 162. In various embodiments, second attachment bracket 117 includes a third aperture 163 in coaxial alignment with the first aperture 161 and a fourth aperture 164 in coaxial alignment with the second aperture 162. Bracket 140 may include a fifth aperture 165 and a sixth aperture 166. Surgical light 100 may further include a middle hinge pin 172. The fifth aperture 165 is configured to receive the middle hinge pin 172. The glasses bracket 140 is configured to rotate about the middle hinge pin 172 to adjust an angle of surgical light 100 with respect to a user's glasses and/or head as desired. Surgical light 100 further includes a top hinge pin 174 and a bottom hinge pin 176. The sixth aperture 166 is configured to receive the top hinge pin 174. The second aperture 162 and the fourth aperture 164 are configured to receive the bottom hinge pin 176. Surgical light 100 may further include an adjustment member 178 configured to be threadingly coupled to the bottom hinge pin 176. Adjustment member 178 may be configured to extend through the top hinge pin 174, such that rotation of the adjustment member 178 with respect to bottom hinge pin 176 in a first rotational direction (e.g., counter-clockwise) causes the top hinge pin to move away from the bottom hinge pin 176 (see FIG. 12A) and rotation of the adjustment member 178 with respect to bottom hinge pin 176 in a second rotational direction (e.g., clockwise) causes the top hinge pin to move toward bottom hinge pin 176 (see FIG. 12B). In this manner, with top hinge pin 174 coupled to bracket 140, the glasses bracket 140 is configured to rotate about the middle hinge pin 172 with respect to the rear cap 130 in response to the adjustment member 178 rotating with respect to the bottom hinge pin 176 so as to adjust an angle of surgical light 100 with respect to a user's glasses and/or head as desired.

FIG. 3A through FIG. 3D illustrate various views of the bezel 110 of the surgical light 100, in accordance with various embodiments. Bezel 110 may comprise an annular body with a threaded inner diameter surface whereby bezel 110 is threadingly coupled to light body 120 (see FIG. 1A).

FIG. 4A through FIG. 4H illustrate various views of the light body 120 of the surgical light 100, in accordance with various embodiments. Light body 120 may comprise an annular body 122. Annular body 122 may define a center aperture 125 whereby wires and/or other components of surgical light 100 may be routed. A first flange 124 may extend from annular body 122 and may be configured to receive LED star 114 (see FIG. 2A). A second flange 126 may extend from annular body 122. Second flange 126 may increase the overall surface area of light body 120 to provide enhanced cooling to surgical light 100. A third flange 128 may extend from annular body 122. Third flange 128 may be configured to receive PCB 150 (see FIG. 2B). Third flange 128 may be coupled to rear cap 130 (see FIG. 1A).

Figures 5A, 5B, 5C, 5D:
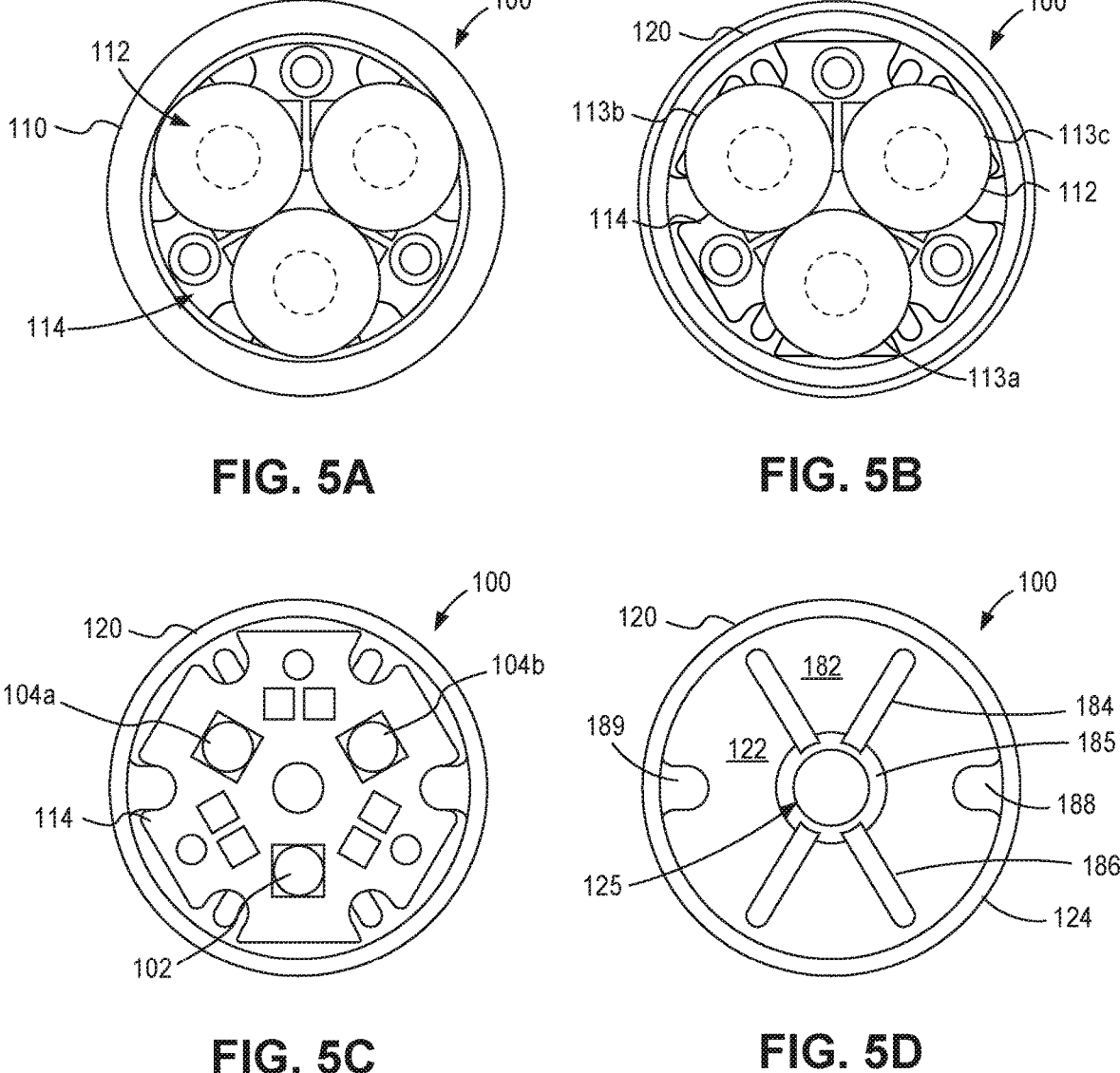
FIG. 5A illustrates a front view of a surgical light of the present disclosure, in accordance with various embodiments.
FIG. 5B illustrates a front view of the surgical light of FIG. 5A with the bezel removed, in accordance with various embodiments.
FIG. 5C illustrates a front view of the surgical light of FIG. 5B with the lens removed, in accordance with various embodiments.
FIG. 5D illustrates a front view of the surgical light of FIG. 5C with the LED star removed, in accordance with various embodiments.

FIG. 5A illustrates a front view of the surgical light 100, in accordance with various embodiments.

FIG. 5B illustrates a front view of the surgical light 100 of FIG. 5A with the bezel 110 removed, in accordance with various embodiments. Lens 112 may include a plurality of frustoconical portion (e.g., frustoconical portions 113a, 113b, 113c), each for focusing light emitted from an associated LED.

FIG. 5C illustrates a front view of the surgical light 100 of FIG. 5B with the lens 112 removed, in accordance with various embodiments. LED star 114 may include three LEDs. In an example embodiment, LED star 114 includes first LED 102, second LED 104a, and third LED 104b. First LED 102 may comprise an ultraviolet-emitting LED. Second LED 104a and third LED 104b may produce white light. It should be noted that white LED lights (e.g., second LED 104a and/or third LED 104b) may be a cool white LED, or a neutral white LED, or a warm white LED depending on the particular intended application. It should be further noted that second LED 104a and third LED 104b may be capable of emitting other color lights (e.g., blue, green, yellow, red, etc.) and that the color of light of second LED 104a and third LED 104b is not particularly limited. Second and third LEDs 104a, 104b may be capable of emitting 25,000-200,000 LUX of light, in accordance with various embodiments.

First LED 102 may be configured to emit ultraviolet (or near ultraviolet) light (also referred to as ultraviolet visible (UVV). In various embodiments, first LED 102 is configured to emit ultraviolet light having a wavelength of between 400-420 nm, and in various embodiments, having a wavelength of between 405-410 nm or 490-505 nm In various embodiments, surgical light 100 may be configured to switch between first LED 102, second LED 104a, and third LED 104b (e.g., first LED 102 OFF and second and third LEDs 104a, 104b ON, or first LED 102 ON and second and third LEDs 104a, 104b OFF, etc.) depending on a user's preference (e.g., by a user's voice command). Moreover, surgical light 100 may be configured to initiate a strobe sequence back and forth between first LED 102 and second and third LEDs 104a, 104b to allow a surgeon to switch between visible white light to view the surgical site, and UV light to view pathologic cells with the aid of various compounds (e.g., fluorescent dyes, among others) that act to make pathologic tissue glow or in other ways be visually distinct from normal tissues. For example, a user may use a voice command (e.g., "STROBE" or "SWEEP") and the controller (e.g., the processor) of surgical light 100 may automatically command a strobe sequence back and forth between white light and UV or narrow bandwidth light. Moreover, the user may use other commands to dim, brighten, turn on, turn off, and switch between different LEDs using voice commands. In this manner, a surgeon is able to maintain their field of sterility during a surgical procedure without reaching for dials to adjust light parameters.

FIG. 5D illustrates a front view of the surgical light 100 of FIG. 5C with the LED star 114 removed, in accordance with various embodiments. First flange 124 of light body 120 may define an opening having a back face 182 at least partially defined by annular body 122. One or more channels may be disposed in back face 182 for routing wires from center aperture 125 around LED star 114 (see FIG. 5C). For example, back face 182 may comprise a first channel 184 extending outwardly from center aperture 125. Back face 182 may further comprise a second channel 186 extending outwardly from center aperture 125. Annular body 122 may comprise a bevel 185 at the interface between the inner diameter surface defining center aperture 125 and back face 182 to accommodate the routing of wires. Bevel 185 may further prevent wires from kinking, fraying, or damage. One or more keys (e.g., first key 188 and/or second key 189) may extend longitudinally (i.e., with respect to the centerline axis 190 (see FIG. 4H) of light body 120) from back face 182. Keys 188, 189 may comprise structural bosses extending from back face 182. Keys 188, 189 may be received by corresponding cutouts in LED star 114 (see FIG. 5C) to prevent LED star 114 from rotating with respect to light body 120 in the installed position. As illustrated in FIG. 5D, light body 120 comprises a hole in back face 182. Surgical light may comprise a circuit board more proximal than LED star 114 (and light body 120), and LED star 114 is driven by a circuit (e.g., a processor) on the circuit board. Connections between the circuit board and LED star 114 may be drawn through the hole in back face 182 to supply power or control signals to LED star 114 during operation.

FIG. 6A through FIG. 6E illustrate various views of the PCB 150 of the surgical light 100, in accordance with various embodiments. PCB 150 may include one or more processors, such as processor 210. Processor 210 may include one or more controllers (e.g., processors) and one or more tangible, non-transitory memories capable of implementing digital or programmatic logic. In various embodiments, for example, the one or more controllers are one or more of a general purpose processor, digital signal processor (DSP), application specific integrated circuit (ASIC), field programmable gate array (FPGA), a microcontroller, an embedded processor, an application-specific system processors (ASSP), an application-specific instruction set processor (ASIP), an ASIC processor, and/or a multiprocessor, or other programmable logic device, discrete gate, transistor logic, or discrete hardware components, or any various combinations thereof or the like. In various embodiments, processor 210 controls, at least various parts of, and operation of various components of, the surgical light 100. For example, processor 210 controls various parameters of the LEDs, such as brightness, turning ON and/or OFF, strobe sequences of the LED, switching back and forth between different types of LEDs that emit different frequencies of light, etc. The processor 210 may utilize voice commands and/or sensor input for controlling the LEDs.

Processor 210 may utilize temperature sensor input for controlling the brightness of the LEDs. More particularly, processor 210 may be configured to reduce the brightness of the LEDs in response to the temperature sensor measuring a temperature that exceeds a maximum allowable temperature. In this manner, processor 210 may control the surgical light 100 brightness so as to not exceed the maximum allowable temperature. In this manner, the surgical light 100 may be limited to a brightness and/or duration of said brightness so that the device is able to effectively dissipate the generated heat. Stated differently, the light may be thermally controlled.

In some embodiments, processor 210 controls a light source (e.g., one or more LEDs) based at least in part on a detected temperature (e.g., detected heat) at, or in proximity to, the circuit board. In response to detecting that the temperature exceeds a predefined temperature threshold, processor 210 controls to decrease the brightness of the light source (e.g., decrease the amount of power that processor drives the light source. In various embodiments, processor 210 uses a plurality of predefined temperature thresholds to progressively decrease the brightness of the light source (and thus heat generated by the light source) as the temperature detected at the circuit board increases. As an example, the system stores (i) a first temperature threshold corresponding to 80% of a predefined maximum operating temperature, (ii) a second temperature threshold corresponding to 90% of predefined maximum operating temperature, and (iii) a third temperature threshold corresponding to 95% of the predefined maximum temperature. In response to detecting that the temperature exceeds the first temperature threshold (e.g., the temperature is greater than the first temperature threshold but less than the second temperature threshold), processor 210 controls to decrease the brightness by a first brightness value (e.g., decreases power to the light source by 5%). In some embodiments, the first temperature threshold is set at 70° C. In response to detecting that the temperature exceeds the second temperature threshold (e.g., the temperature is greater than the second temperature threshold and less than the third temperature threshold), processor 210 controls to decrease the brightness by a second brightness value (e.g., decreases the brightness or power to the light source by 5%, such as a further 5% reduction after the power being reduced after exceeding the first temperature threshold). In response to detecting that the temperature exceeds the third temperature threshold (e.g., the temperature is greater than the third temperature threshold), processor 210 controls to decrease the brightness by a third brightness value (e.g., decreases the brightness or power to the light source by 5%, such as a further 5% reduction after the power being reduced after exceeding the second temperature threshold). The foregoing temperature threshold and corresponding brightness values (e.g., by which the brightness of the light source is reduced) are merely examples.

Various other temperature thresholds and brightness values may be implemented, and various numbers of thresholds may be implemented. For example, in various embodiments a sufficient number of temperature thresholds and corresponding brightness values are implemented to provide more granular control of the light source (e.g., control responsive to detected temperature) to cause the change in brightness of light source during operation to be substantially imperceptible. The temperature threshold and/or brightness values may be configurable, such as by a user via integrated software (e.g., a phone app running on a phone that is connected to surgical light 100).

Processor 210 may be configured to command visual feedback for various commands. In various embodiments, processor 210 may cause the LEDs to blink (e.g., blink twice) when the surgical light 100 is at the end of an adjustment range. For example, the LEDs may be configured to provide visual feedback (e.g., blink twice) when a user asks the surgical light 100 to be brighter, and the surficial light is already at the brightest setting. Conversely, the LEDs may be configured to provide visual feedback (e.g., blink twice) when a user asks the surgical light 100 to be dimmer, and the surgical light is already at the dimmest setting. In this manner, the surgical light 100 may be configured to provide visual feedback (e.g., by blinking) to let the user know that no more adjustments are available.

Moreover, processor 210 may be configured to command visual feedback (e.g., cause the LEDs to blink) when the surgeon asks (e.g., via voice command) the surgical light 100 to recall and record a trajectory. The surgical light 100 may provide visual feedback when the surgical light 100 is again oriented in that trajectory (e.g., by blinking). The surgical light 100 may utilize accelerometers to monitor the orientation of the surgical light. In addition to blinking on and off, surgical light 100 may use rate of oscillation of intensity as a means to provide the surgeon with feedback about position relative to a saved or targeted position. For example, when a surgeon looks down the shaft of a navigated tool during surgery and asks the light to record the trajectory. When searching for the proper trajectory, the surgeon may ask for guidance. Guidance feedback may involve the light output changing between 50% and 100% intensity in a sinusoidal pattern with a first predetermined period (e.g., 1 second) while the difference in angle is greater than 50%. When the difference is greater than 25% but less than 50% the period may increase (e.g., to 0.5 seconds) and so on. As the difference between saved trajectory and surgeon head position reaches 0, the rate of oscillation may increase. The converse may also be used where the rate decreases as the difference decreases.

PCB 150 may further include an audio output amplifier 202. Audio output amplifier 202 may be used to provide auditory feedback that a command has been properly registered and executed, or to provide surgical feedback provided by a surgical navigational system with which surgical light 100 is registered. Audio output amplifier 202 may also be used to provide auditory feedback about surgeon view/head position relative to a saved trajectory, etc., as well. This may be similar to the above description with respect to the LED light in that the feedback tone may increase as the difference between surgeon position and saved trajectory decreases.

PCB 150 may further include an accelerometer 204. Accelerometer 204 may supply surgical light orientation feedback to processor 210. Processor 210 may be configured to turn various LEDs ON and/or OFF based upon the orientation of surgical light 100. Additionally, accelerometer 204 can be used along with processor 210 to understand motion commands that can be trained by the user to invoke any and all of the functionality of the surgical light 100. For example, double fast head nod may be trained as a light brighter command, double negative head nod may equal light dimmer, etc. As previously noted, the light on and off may be controlled by movement of the device. When the accelerometer 204 detects subtle motion, processor 210 may control the light to be turned on and if processor 210 senses no motion for greater than a preset amount of time (e.g., a user definable parameter) processor 210 may control the light to be turned off.

PCB 150 may further include a digital microphone 206. Processor 210 may receive voice commands via digital microphone 206. Various other microphones may be implemented. For example, surgical light 100 may include a stereo microphone arrangement or a microphone array (e.g., for the purpose of beam forming). Various other orientations of the microphone may be implemented. For example, the microphone 206 may be disposed on either side of PCB 150. Although the sound port for digital microphone 206 is illustrated as facing anteriorly, in various embodiments, the sound port may be oriented to face posteriorly.

PCB 150 may further include ON/OFF switch 132 for turning the surgical light ON or OFF.

PCB 150 may further include an antenna 208. Processor 210 may communicate with a remote computing device (e.g., a cellphone) whereby various parameters of surgical light 100 may be adjusted. Moreover, processor 210 may record information to the remote computing device via antenna 208, such as voice-generated notes made during a procedure.

PCB 150 may further include a temperature sensor.

In various embodiments, PCB 150 includes one or more cutaways (e.g., through holes) that partly define one or more pathways via which heat is vented through the back of the surgical light (e.g., a proximal side of surgical light). The one or more cutaways may be configured to draw heat from the heat sink and away from other components on PCB 150.

Figures 6A, 6B, 6C, 6D, 6E:
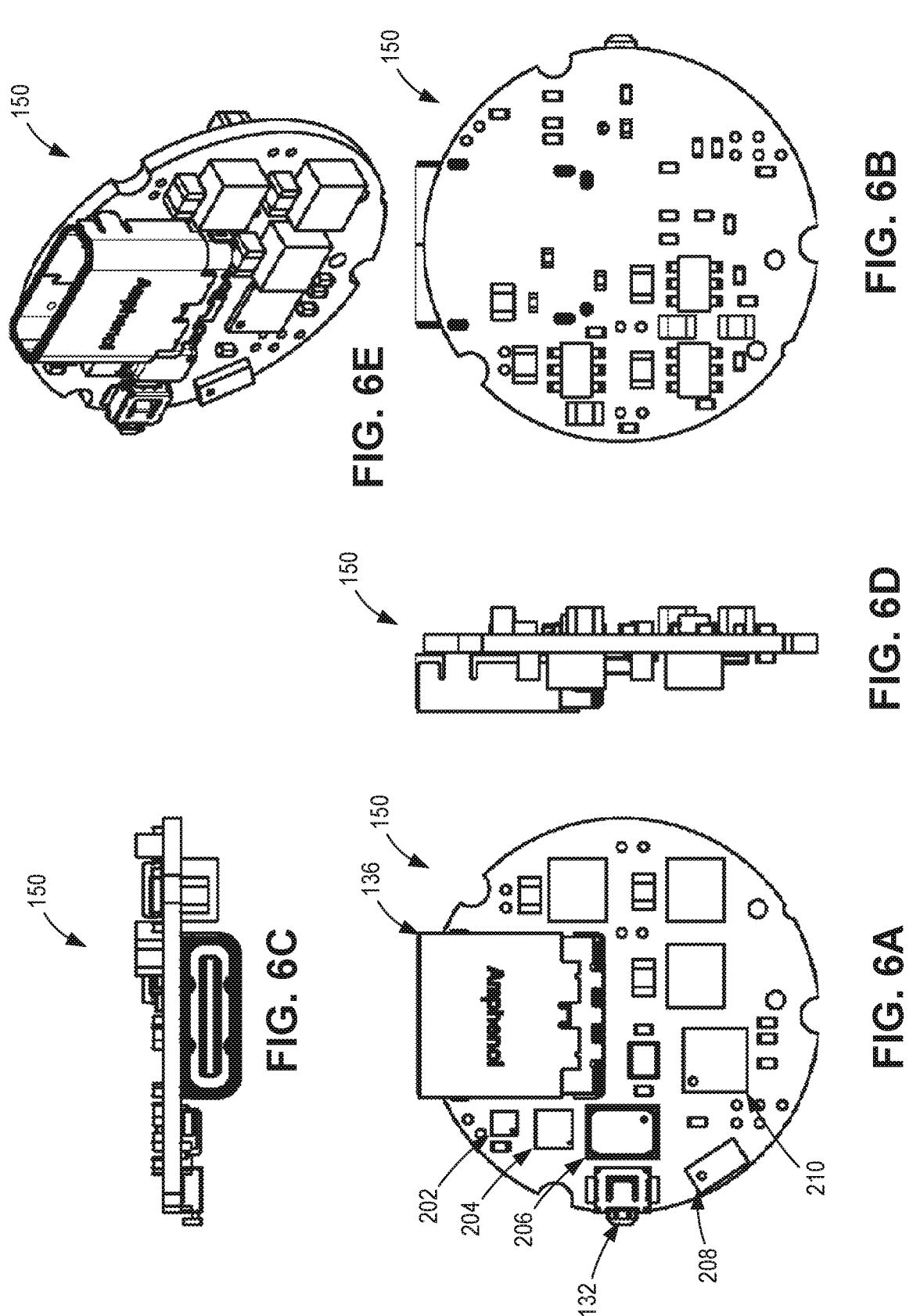
FIGS. 6A, 6B, 6C, 6D, and 6E illustrate front, rear, top, side, and perspective views, respectively, of a printed circuit board (PCB) of a surgical light of the present disclosure, in accordance with various embodiments.
Figure 6F:
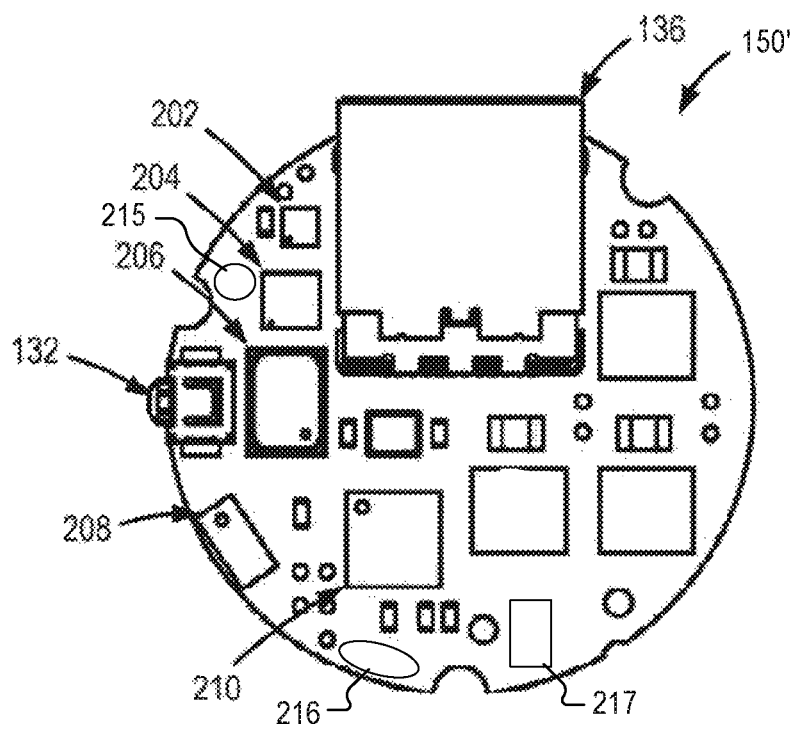
FIG. 6F illustrates a front view of a printed circuit board (PCB) of a surgical light according to various embodiments.
Figures 7A, 7B, 7C, 7D, 7E:
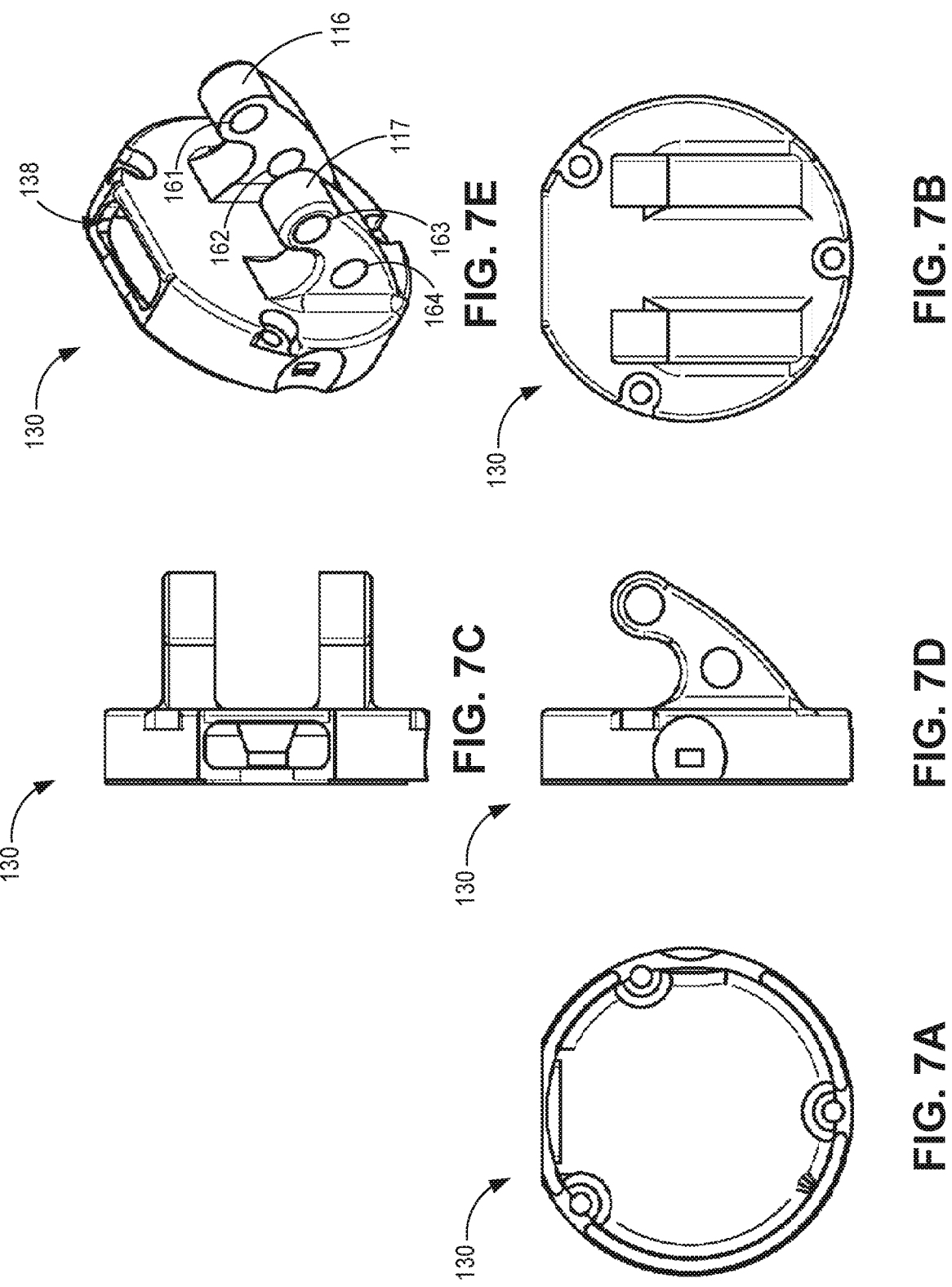
FIGS. 7A, 7B, 7C, 7D, and 7E illustrate front, rear, top, side, and perspective views, respectively, of a rear cap of a surgical light of the present disclosure, in accordance with various embodiments.
Figure 9C:
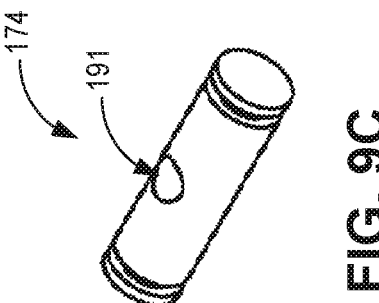
FIGS. 9A, 9B, 9C, and 9D illustrate top, front, perspective, and side views, respectively, of a top hinge pin of a surgical light of the present disclosure, in accordance with various embodiments.
Figure 9D:
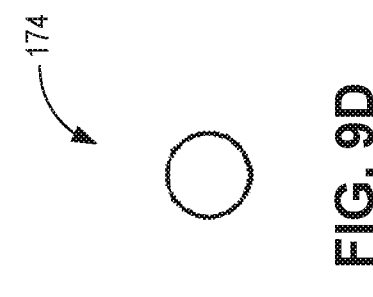
Figure 9A:
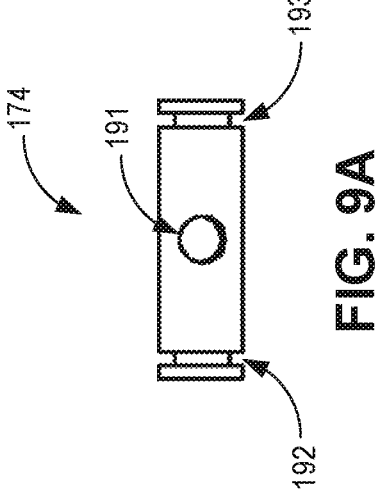
Figure 9B:
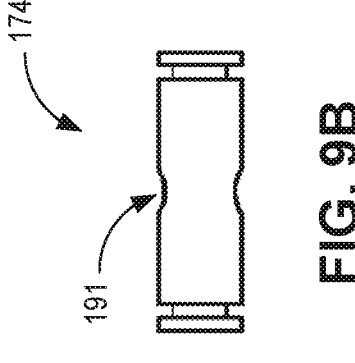
Figure 10C:
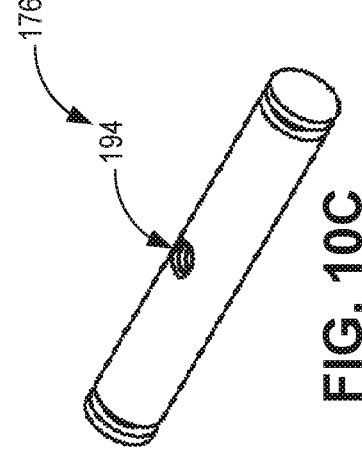
FIGS. 10A, 10B, 10C, and 10D illustrate top, front, perspective, and side views, respectively, of a bottom hinge pin of a surgical light of the present disclosure, in accordance with various embodiments.
Figure 10D:
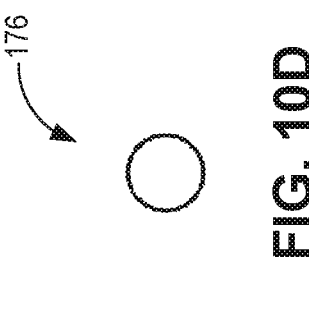
Figure 10A:
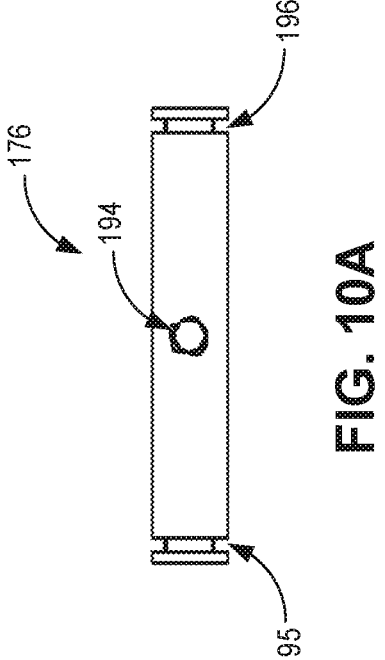
Figure 10B:
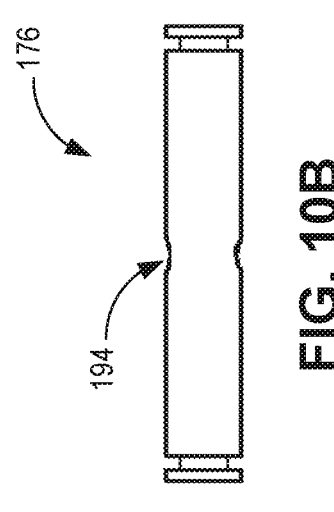

FIG. 6F illustrates a front view of a printed circuit board (PCB) of a surgical light according to various embodiments. In the example shown, PCB 210 includes through holes 215, 216, and 217. In some embodiments, the through holes provided on PCB 210 are positioned in areas of PCB 210 without any circuit elements or tracing between circuit elements (e.g., copper tracing to connect various components). As illustrated in FIG. 6F, the through holes may have various shapes (e.g., circle, ellipse, rectangle, square, etc.) or sizes.

FIG. 7A through FIG. 7E illustrate various views of the rear cap 130 of the surgical light 100, in accordance with various embodiments. With respect to FIG. 7E, elements with like element numbering, as depicted in FIG. 2B, are intended to be the same and will not necessarily be repeated for the sake of clarity.

FIG. 8A through FIG. 8E illustrate various views of the glasses bracket 140 of the surgical light 100, in accordance with various embodiments. With respect to FIG. 8A though FIG. 8E, elements with like element numbering, as depicted in FIG. 2B, are intended to be the same and will not necessarily be repeated for the sake of clarity. Bracket 140 may further include a clamp portion 142 configured to be placed over a portion of a user's glasses to secure the surgical light to the user's head. In various embodiments, clamp portion 142 may be placed over the bridge portion of a user's glasses (e.g., see FIG. 13). Clamp portion 142 may comprise a first finger 144 and a second finger 146. The portion of the user's glasses may be received between first finger 144 and second finger 146. First finger 144 may include a threaded aperture 148 for receiving a set screw 145, with momentary reference to FIG. 2B. Set screw 145 may be tightened and extend into the gap between first finger 144 and second finger 146, thereby contacting the portion of the user's glasses and compressing the portion of the user's glasses between the set screw 145 and second finger 146.

It should be appreciated that first finger 144 and second finger 146 may be sized and designed such that the portion of the user's glasses is compressed between first finger 144 and second finger 146 without a set screw. In various embodiments, the inner surfaces of first finger 144 and second finger 146 may be lined with a soft, compressible material to help clamp portion 142 grip the portion of the user's glasses.

FIG. 9A through FIG. 9D illustrate various views of the top hinge pin 174 of the surgical light 100, in accordance with various embodiments. Top hinge pin 174 may consist of a rod. In various embodiments, top hinge pin 174 may be made of a metal material, such as stainless steel. In various embodiments, top hinge pin 174 may be made of a hard plastic material. Top hinge pin 174 includes a through hole 191 extending through top hinge pin 174. Through hole 191 may extend orthogonal with respect to top hinge pin 174. Stated differently, a centerline axis of through hole 191 may be orthogonal with respect to a centerline axis of top hinge pin 174. In various embodiments, through hole 191 is located at a midpoint between the ends of top hinge pin 174.

In various embodiments, each end of top hinge pin 174 comprises an annular groove for receiving a lock ring to secure top hinge pin 174 to glasses bracket 140. For example, a first end of top hinge pin 174 may comprise a first annular groove 192 and a second end of top hinge pin 174 may comprise a second annular groove 193. However, it should be appreciated that only one end of top hinge pin 174 may comprise an annular groove, while the other end is secured via some other means (e.g., a flanged head or the like).

FIG. 10A through FIG. 10D illustrate various views of the bottom hinge pin 176 of the surgical light 100, in accordance with various embodiments. Bottom hinge pin 176 may be similar to top hinge pin 174, except that bottom hinge pin 176 is longer than top hinge pin 174, in various embodiments, and the through hole disposed in bottom hinge pin 176 is threaded. Bottom hinge pin 176 may consist of a metal, plastic, or composite rod. Bottom hinge pin 176 includes a threaded through hole 194 extending through bottom hinge pin 176. Through hole 194 may extend orthogonal with respect to bottom hinge pin 176. Stated differently, a centerline axis of through hole 194 may be orthogonal with respect to a centerline axis of bottom hinge pin 176. In various embodiments, through hole 191 is located at a midpoint between the ends of bottom hinge pin 176.

In various embodiments, each end of bottom hinge pin 176 comprises an annular groove for receiving a lock ring to secure bottom hinge pin 176 to glasses bracket 140. For example, a first end of bottom hinge pin 176 may comprise a first annular groove 195 and a second end of bottom hinge pin 176 may comprise a second annular groove 196. However, it should be appreciated that only one end of bottom hinge pin 176 may comprise an annular groove, while the other end is secured via some other means (e.g., a flanged head or the like).

FIG. 11A through FIG. 11D illustrate various views of the middle hinge pin 172 of the surgical light 100, in accordance with various embodiments. Middle hinge pin 172 may be similar to bottom hinge pin 176, except that middle hinge pin 172 does not necessarily include a through hole, in accordance with various embodiments. Middle hinge pin 172 may consist of a metal, plastic, or composite rod. In various embodiments, each end of middle hinge pin 172 comprises an annular groove for receiving a lock ring to secure middle hinge pin 172 to glasses bracket 140. For example, a first end of middle hinge pin 172 may comprise a first annular groove 197 and a second end of middle hinge pin 172 may comprise a second annular groove 198. However, it should be appreciated that only one end of middle hinge pin 172 may comprise an annular groove, while the other end is secured via some other means (e.g., a flanged head or the like).

Figure 12A:
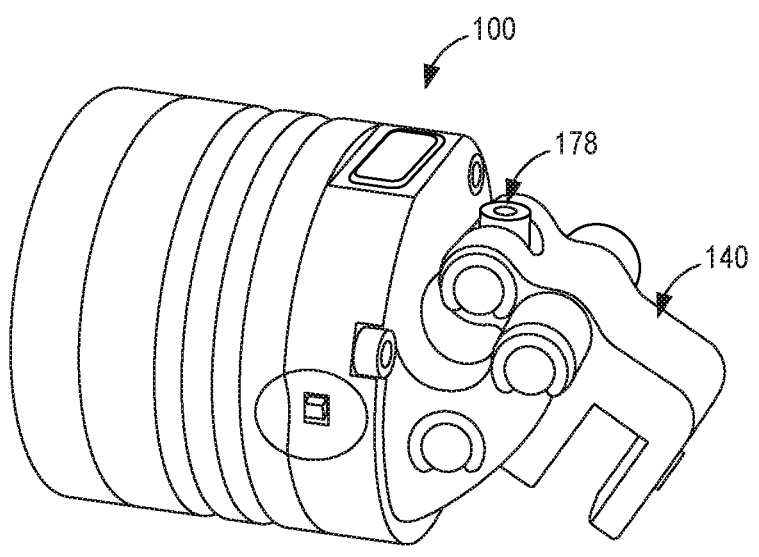
FIGS. 12A and 12B illustrate a glasses bracket of a surgical light of the present disclosure in a first position and a second position, respectively, in accordance with various embodiments.
Figure 12B:
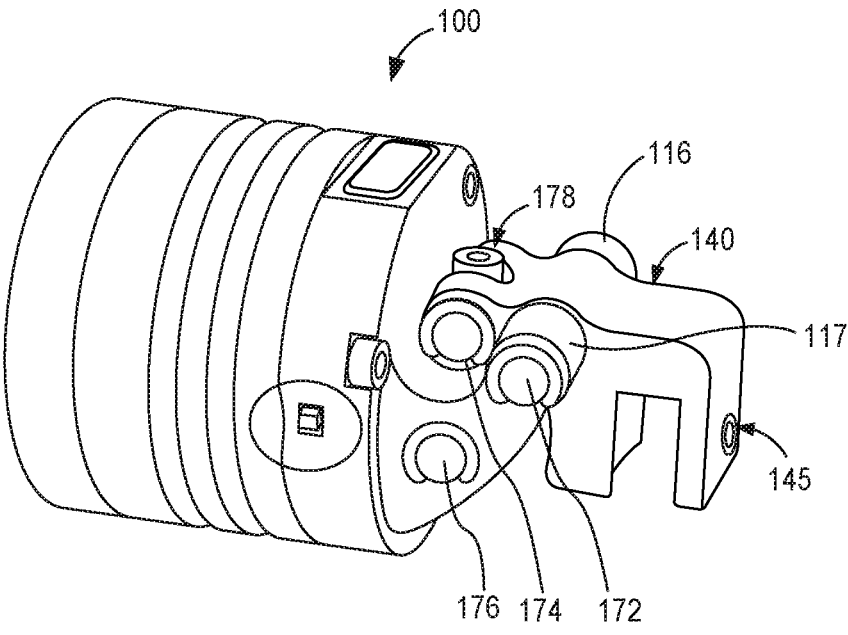

FIG. 12A and FIG. 12B illustrate the glasses bracket 140 of the surgical light 100 in a first position and a second position, respectively, in accordance with various embodiments. With respect to FIG. 12A and FIG. 12B, elements with like element numbering, as depicted in FIG. 1A through FIG. 11D, are intended to be the same and will not necessarily be repeated for the sake of clarity.

Figure 13:
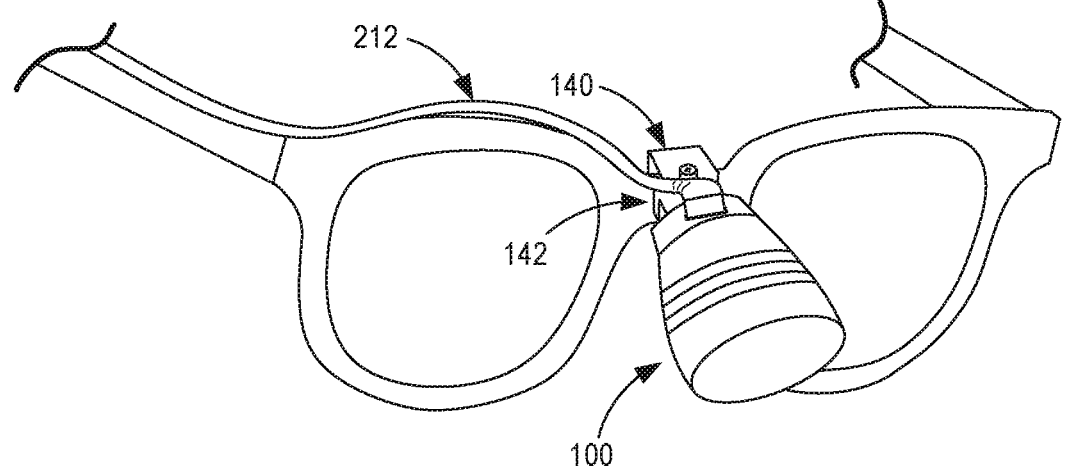
FIG. 13 illustrates a surgical light of the present disclosure installed onto a pair of glasses and connected to a power supply, in accordance with various embodiments.

FIG. 13 illustrates surgical light 100 installed onto a pair of glasses and connected to a power supply, in accordance with various embodiments. A power cord 212 may be connected to surgical light 100 (i.e., at power supply connector 136 with momentary reference to FIG. 1D). An opposite end of power cord 212 may be connected to a power supply which may be worn by the user, for example secured to a user's head, waist, or placed in the user's pocket. Power cord 212 may be routed around the user's head as desired, for example along the eyeglasses/loupe frame. Power cord 212 may be configured to be connected/disconnected at the back of the user's head. In this regard, power cord 212 may be a relatively short power cord extending from the light mounted on the loupes around the head and to a connector at the back of the surgeon's neck. By placing the connection to the power source at the surgeon's head, the surgeon's sterile field may tend to be better maintained. When the surgeon wants her or his loupes and associated light removed (e.g., in order to go under the surgical microscope), the connection at this location allows the assistant to disconnect the extension cord that connects the short cord to the battery pack and leave the extension cord on the surgeon beneath their gown. The loupes, light, and associated short cord are removed and able to be replaced simply as a unit and reconnected to allow resumption of loupes with headlamp lighting without significantly adding to the time that it takes for the assistant to replace the loupes.

In some embodiments, the power cord is between 33-55 inches long. In some embodiments, power cord 212 is between 13 and 24 inches long. In some embodiments, the surgical cord is between 16 and 20 inches long. Power cord 212 may comprise a USB-C female-to-male connector at the back of the user's head.

Figure 14:
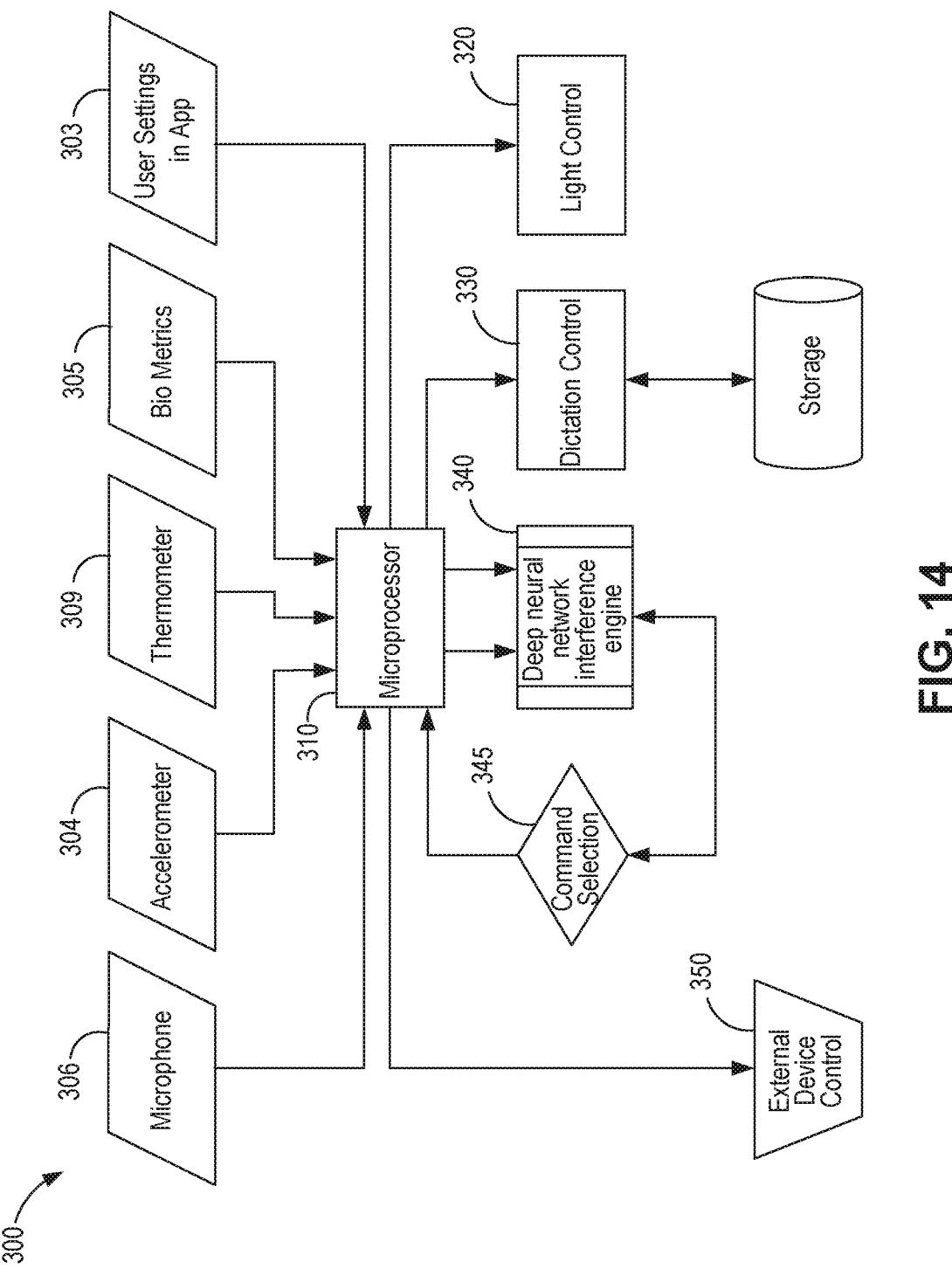
FIG. 14 illustrates a block diagram of a light control system for a surgical light of the present disclosure, in accordance with various embodiments.

With reference to FIG. 14, a block diagram of a control system 300 for a surgical light is illustrated, in accordance with various embodiments. Control system 300 includes a lighting controller 310 (e.g., a processor) configured to receive various input signals include from a microphone 306 (e.g., one or more microphones), an accelerometer 304, a temperature sensor 309 (e.g., one or more temperature sensors), bio metric sensor(s) 305, and/or user in-app settings 303 (e.g., from a mobile device). Controller 310 may be similar to processor 210 (see FIG. 6A).

Controller 310 may utilize these inputs and send commands to a light control 320 for controlling the state of the LEDs (e.g., ON, OFF, brightness, etc.).

Controller 310 may pass voice command inputs received from microphone 306 to dictation control 330 for interpreting the voice command inputs and generating appropriate light control commands. For example, in response to receiving the voice command input corresponding to a dictation command, controller 310 recognizes the command input and records the dictation (e.g., the speech input by the user). In some embodiments, controller 310 uses a neural network to determine when the dictation ends (e.g., when the speech stops). Accordingly, controller 310 controls to record dictation when the user instructs the system to do so and ends the dictation recording when the user stops talking/dictating.

Controller 310 may pass voice command inputs received from microphone 306 to neural network 340 for interpreting the voice command inputs and generating appropriate light control commands using command selection 345.

Controller 310 may similarly send command signals to external devices (e.g., overhead lighting) via external device control 350. In this regard, controller 310 may be configured to control other devices in an operating room (in addition to the surgical light) based on the inputs. Controller 310 may send commands back to a navigation system as described herein as well.

Various wavelength LEDs can also be controlled in real time by patient- and surgeon-measured characteristics and lab values. Controller(s) 310 can receive bio metric signals from one or more bio metric sensors 305 associated with a patient and/or a surgeon engaged transducers that are measuring temperature, pulse, blood pressure, oxygen saturation, photoplethysmography, plethysmography, medication and chemistry administration, ventilation parameters, somatosensory evoked potentials, motor evoked potentials, electromyogram, electroencephalography, electrocardiography, and other electrical, mechanical, and chemical sensors. These bio metric signals can be processed, interpreted and used to modulate light output characteristics in ways that provide additional insight into the patient's anatomy or in response to changes in surgeon condition. The bio metric signals can be received by wireless (e.g., Bluetooth Low Energy (BLE)) and/or wired signal.

In one exemplary embodiment, two wavelengths of light that are absorbed differently by oxygenated hemoglobin and deoxygenated hemoglobin may be modulated in a way that the light that is absorbed more completely by oxygenated arterial blood is shone more brightly in a pattern that is temporally associated with the arterial phase of the patient's cardiovascular cycle. Another wavelength of light that is absorbed more completely by deoxygenated blood may be modulated to shine more brightly during the venous phase of the patient's cardiovascular cycle. The differences appreciated may provide additional confidence and insight in differentiating between arterial and venous vessels as well as judging areas of relative ischemia during procedures.

In another exemplary embodiment, certain wavelengths of light may be modulated in a timed fashion that is coordinated with the administration of a substance or medication. This may be done to facilitate further visualization of the distribution of said substances or medications which may be selectively taken up by certain groups of cells representing healthy cells or pathologic cells.

Figure 15:
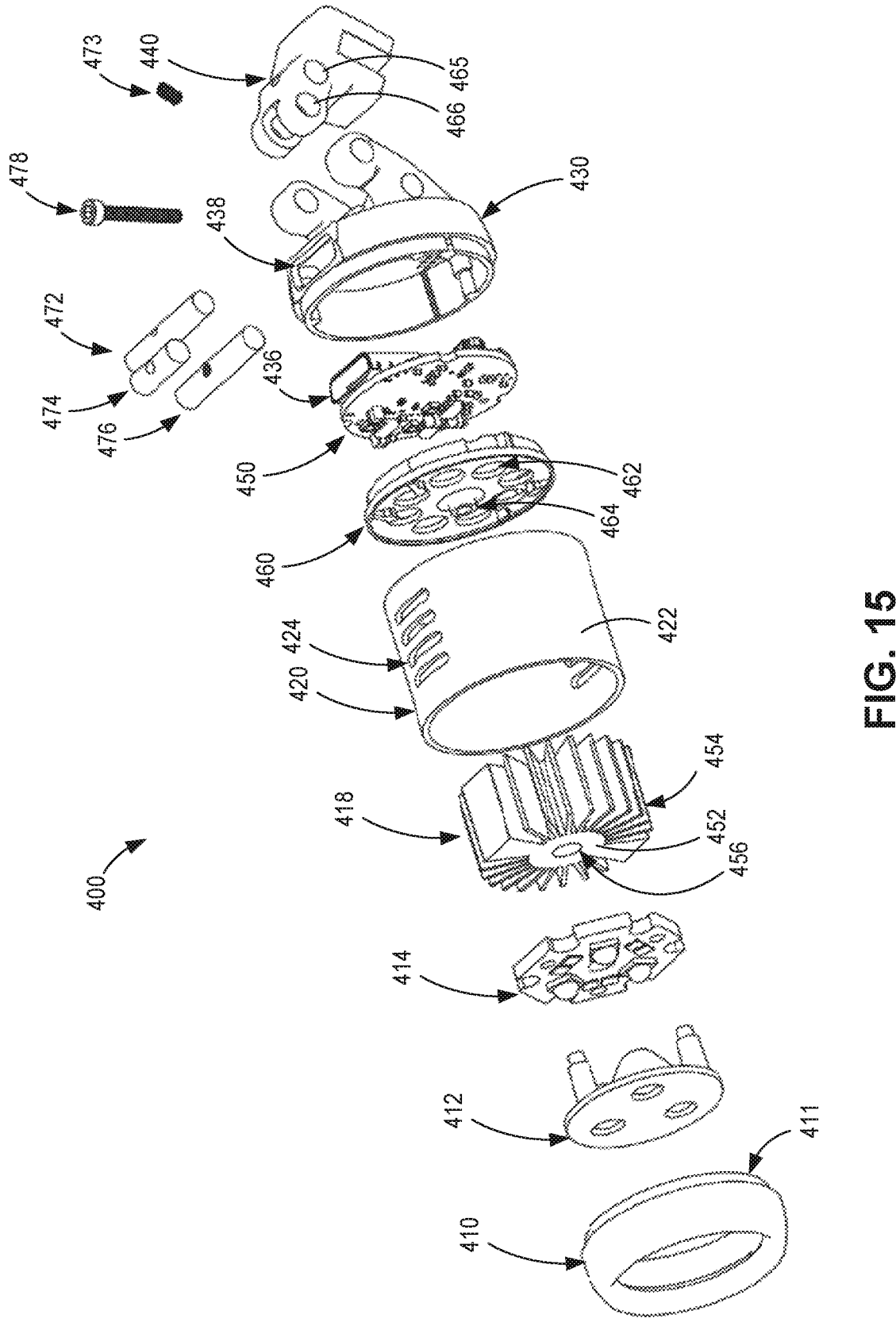
FIG. 15 illustrates an assembly view of a surgical light of the present disclosure, in accordance with various embodiments.

FIG. 15 illustrates an assembly view of a surgical light 400, in accordance with various embodiments. Surgical light 400 may operate similar to surgical light 100 (see FIG. 1 through FIG. 13). However, surgical light 400 may have structural differences from surgical light 100. Surgical light 400 includes a bezel 410, a light body 420, a rear cap 430, and a bracket 440 (also referred to herein as a glasses bracket). Bezel 410, light body 420, and rear cap 430 may be generally coaxially aligned in the installed position.

Surgical light 400 may further include a lens 412 for focusing light emitted from one or more LEDs (light emitting diodes) disposed on LED star 414. In this manner, LED star 414 may be disposed between lens 412 and light body 420. Lens 412 may be disposed between bezel 410 and LED star 414. A subset of a plurality of LEDs disposed on LED star 414 may emit light at different wavelengths.

Surgical light 400 may further include a PCB 450. PCB 450 may be disposed between light body 420 and rear cap 430. PCB 450 may be similar to PCB 150 (see FIG. 2A).

Surgical light 400 further includes a power supply connector 436 for connecting a power supply to surgical light 400. Rear cap 430 may include an opening 438 for accommodating power supply connector 436. Power supply connector 436 may be similar to power supply connector 136 (see FIG. 2A).

Rear cap 430 may be similar to rear cap 130 (see FIG. 2A and FIG. 2B). Surgical light 400 may further include a middle hinge pin 472, a top hinge pin 474, and a bottom hinge pin 476. Middle hinge pin 172, a top hinge pin 174, and a bottom hinge pin 176 may be similar to middle hinge pin 172, top hinge pin 174, and bottom hinge pin 176 (see FIG. 2A and FIG. 2B) in accordance with various embodiments. Middle hinge pin 472 and top hinge pin 474 may be made of plastic. Bottom hinge pin may be made of aluminum. Bracket 440 may be similar to bracket 140 (see FIG. 2A and FIG. 2B), except that bracket 440 further includes a set screw 473 configured to extend through bracket 440 and engage middle hinge pin 472 to secure middle hinge pin 472 to bracket 440. For example, set screw 473 may engage an aperture or dimple in middle hinge pin 472. Surgical light 400 may further include an adjustment member 478. Adjustment member 478 may be similar to adjustment member 178 (see FIG. 2A). Adjustment member 478 may comprise a bolt, a screw, or the like.

In some embodiments, rear cap 430 comprises one or more ports via which heat transferred from the heat sink is vented. For example, rear cap 430 comprises a plurality of ports corresponding to pathways via which heat is vented through fluting configured on an inner wall of light body 420 and/or rear cap 430 to vent air substantially around the outer circumference of PCB 450. In some embodiments, a subset of the one or more ports are used as tuned pathways for soundwave transmission to the microphone (e.g., the microphone ports) comprised in the circuit (e.g., PCB 150).

Surgical light 400 may further include a heat sink 418 configured to be disposed within light body 420. Heat sink 418 may be made from a metal material such as aluminum or an aluminum alloy. Heat sink 418 may comprise an annular body 452 with a plurality of circumferentially disposed fins 454 extending outward from the annular body 452. The plurality of fins 454 may terminate at the inner diameter surface of light body 420. Heat sink 418 may comprise an aperture 456 extending through the center of annular body 452.

Light body 420 may comprise an annular body 422. In some embodiments, light body 420 is a thermally insulative shell, such as a shell configured to receive heat sink 418. Annular body 422 may comprise a fiber-reinforced composite material, such as a carbon fiber-reinforced resin material. Annular body 422 may be a thin-walled annular body with a generally common thickness around the circumference and the length thereof. The wall thickness of annular body 422 may be less than ten percent (10%) of the diameter of annular body 422. The wall thickness of annular body 422 may be less than five percent (5%) of the diameter of annular body 422. Annular body 422 may comprise a plurality of vents 424 extending through annular body 422 (i.e., from the outer diameter surface to the inner diameter surface) to allow for heat to escape light body 420. One or more fins 454 may terminate at vents 424.

Surgical light 400 may further include a support plate 460. Support plate 460 may secure PCB 450 along the anterior margin. Support plate 460 may provide mechanical fixation of the posterior aspect of the heat sink 418. Support plate 460 may maintain appropriate alignment of the heat sink within the light body 420. Support plate 460 may be disposed at an interface between rear cap 430 and light body 420. Support plate 460 may be configured to be disposed at the rear opening of light body 420. Support plate 460 may extend at least partially into light body 420. An opposite side of support plate 460 may extend at least partially into rear cap 430. Support plate 460 may comprise a plurality of apertures 462 whereby one or more wires may be routed from PCB 450 to LED star 414. The apertures 462 may allow airflow for cooling the heat sink 418 as well as minimize weight. The apertures 462 may also allow for the passage of wires leaving the PCB 450 to head to the metal printed circuit board where the LEDs are mounted. When three LEDs are provided, there may be three sets of wires traveling past the heat sink 418. When a single LED is provided, there may be a single set of wires (i.e., two wires) that pass through the backside of the heat sink 418, through one or more apertures on the metal printed circuit board for the LED to supply power to the LED.

In various embodiments, support plate 460 may comprise a boss 464 extending longitudinally therefrom and configured to be received at least partially into aperture 456. Support plate 460 may at least partially support PCB 450 within light body 420.

In various embodiments, the forward side of rear cap 430 may be received at least partially into the rear side of light body 420. In various embodiments, bezel 410 comprises a lip 411 protruding from the rear side thereof and configured to be received at least partially into the forward side of light body 420.

Figure 16:
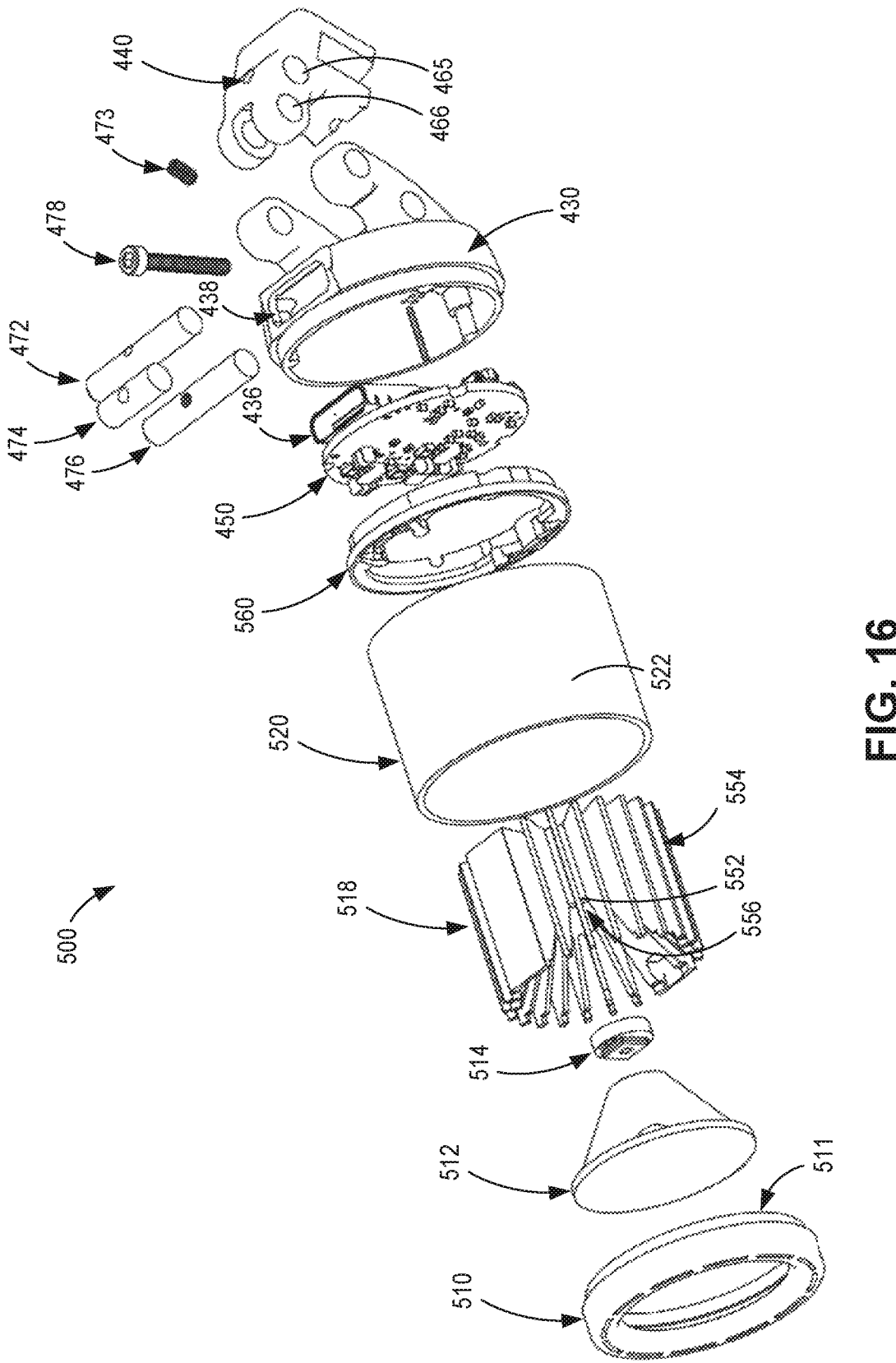
FIG. 16 illustrates an assembly view of a surgical light of the present disclosure, in accordance with various embodiments.

With respect to FIG. 16, elements with like element numbering, as depicted in FIG. 15, are intended to be the same and will not necessarily be repeated for the sake of clarity.

FIG. 16 illustrates an assembly view of a surgical light 500 having a single LED 514, in accordance with various embodiments. Surgical light 500 may operate similar to surgical light 100 (see FIG. 1 through FIG. 13). However, surgical light 500 may have structural differences from surgical light 100 and surgical light 400 (see FIG. 15). Surgical light may have a length of between 35 and 50 mm. In some embodiments, surgical light 500 has a length of 42 mm. Surgical light 500 includes a bezel 510, a light body 520, a rear cap 430, and a bracket 440. Bezel 510, light body 520, and rear cap 430 may be generally coaxially aligned in the installed position.

Surgical light 500 may further include lens 512 for focusing light emitted from LED 514. Although FIG. 16 illustrates a single LED (LED 514), according to various embodiments, surgical light 500 may comprise a plurality of LEDs, and each LED has an independent driver. For example, surgical light 500 comprises two LEDS. As another example, surgical light 500 comprises three LEDs. Lens 512 may comprise a frustoconical geometry. LED 514 may be disposed between lens 512 and heat sink 518. Lens 512 may be disposed between bezel 510 and LED 514.

In some embodiments, lens 415 is made from a polycarbonate.

In some embodiments, bezel is made from plastic.

Surgical light 500 may further include a heat sink 518 configured to be disposed within light body 520. In some embodiments, light body 420 is a thermally insulative shell, such as a shell configured to receive heat sink 418. In some embodiments, heat sink 518 is made from a metal material such as aluminum or an aluminum alloy. Heat sink 518 may comprise an annular body 552 with a plurality of circumferentially disposed fins 554 extending outward from the annular body 552. The plurality of fins 554 may terminate at the inner diameter surface of light body 520 when installed therein. Heat sink 518 may comprise an aperture 556 extending through the center of annular body 552. One or more wires may be routed through aperture 556 between PCB 450 and LED 514. The forward side of the fins 554 may form a frustoconical geometry defining an opening wherein led 514 and at least a portion of lens 512 are disposed when in the installed position. Heat sink 518 may be thermally coupled to the printed circuit board of LED 514. In this manner, heat generated by LED 514 may be conducted into heat sink 518. Heat sink 518 may be machined such that it provides the registration and mounting point of lens 512. In this manner, the total weight of surgical light 400 may be reduced.

According to various embodiments, light body 520 is made of a thermally insulative material, such as carbon fiber composite or plastic. Related art surgical lights include a light body that is thermally conductive to radiate heat from the outside surface of the light body. However, the use of thermally conductive materials for the light body may cause surgical light to be hot to human touch during (or after) operation. The thermally insulative properties of light body 520 minimize heat transfer from heat sink 518 or air within surgical light 500 to the outside walls of light body 520, such as to avoid excessive heat on surfaces that a user may touch surgical light 500. In addition, because related art surgical lamps relied on transferring heat via the light body, the form factor of the light body is relatively large in order to provide adequate surface area over which heat transferred by heat sink 518 is conducted/dissipated. In contrast, various embodiments comprise a substantially thermally insulative light body and a plurality of pathways via which heat transferred to the heat sink is vented through the rear of the surgical light (e.g., the proximal end of the surgical light).

Light body 520 may comprise an annular body 522. Annular body 522 may comprise a fiber-reinforced composite material, such as a carbon fiber-reinforced resin material. Annular body 522 may be a thin-walled annular body with a generally common thickness around the circumference and the length thereof. The wall thickness of annular body 522 may be less than ten percent (10%) of the diameter of annular body 522. The wall thickness of annular body 522 may be less than five percent (5%) of the diameter of annular body 522. In some embodiments, light body 520 has a diameter or cross-sectional length of between 20 mm and 30 mm. In some embodiments, light body 520 has a diameter or cross-sectional length substantially equal to 25.4 mm.

Surgical light 500 may further include a support plate 560. Support plate 560 may be configured to be disposed at the rear opening of light body 520. Support plate 560 may comprise an annular geometry. One side of support plate 560 may extend at least partially into light body 520 and an opposite side of support plate 560 may extend at least partially into rear cap 530. One or more wires may be routed from PCB 450 to LED 514 through support plate 560 (high temp plastic). Support plate 560 may at least partially support PCB 450 within light body 520. Support plate 560 may at least partially support heat sink 518 within light body 520. In some embodiments, support plate 560 at least partially supports heat sink 518, and thus support plate 560 is made of a high temperature plastic to be able withstand the heat transferred by heat sink 518.

In some embodiments, support plate 560 serves as a spacer between heat sink 518 and PCB 450. Support plate 560 is thermally insulative to limit the amount of heat transferred from heat sink 518 through support plate 560 to PCB 450. Support plate 560 may have a sufficient depth to provide sufficient clearance between heat sink 518 and PCB 450 to cause/allow most of the heat to be vented around the outside of PCB 450 (e.g., through pathways defined around the outside of PCB 450, such as via fluting in rear cap 430). As an example, support plate 560 may be configured to position heat sink 518 in surgical light 500 to minimize a surface area of heat sink 518 covered by (e.g., in contact with) support plate 560. Reducing the surface area of heat sink 518 covered by support plate 560 increases the amount of heat transfer performed around the PCB 450 (e.g., ensures that a greater amount of heat is vented through the plurality of pathways around PCB 450).

In some embodiments, support plate 560 is configured in a manner that does not introduce pathways (e.g., conductive air pathways) towards PCB 450. For example, support plate may be shaped to facilitate the flow of air to the outside of PCB 450. As another example, support plate 560 may have sufficient depth to provide clearance for the pathways to be formed at the outside of PCB 450.

In various embodiments, the forward side of rear cap 430 may be received at least partially into the rear side of light body 520. In various embodiments, bezel 510 comprises a lip 511 protruding from the rear side thereof and configured to be received at least partially into the forward side of light body 520.

In some embodiments, rear cap 430 comprises fluting on the inside wall(s) of rear cap 430. For example, rear cap 430 comprises a plurality of grooves extending from a distal end of rear cap 430 towards the proximal end of rear cap 430, and the plurality of grooves may be spaced around the inside circumference of rear cap 430. In some embodiments, length of the grooves is selected to ensure that the grooves extend past the circuit board (e.g., PCB 450 and circuit elements disposed on PCB 450). The configuration of the grooves to extend past the circuit board ensures that heat is vented in the pathways around the outside of the circuit board to a rear part of the light without the circuit components (e.g., which are generally sensitive to heat). In some embodiments, rear cap 430 comprises one or more ports via which heat transferred from heat sink 518 is vented.

Figure 17A:
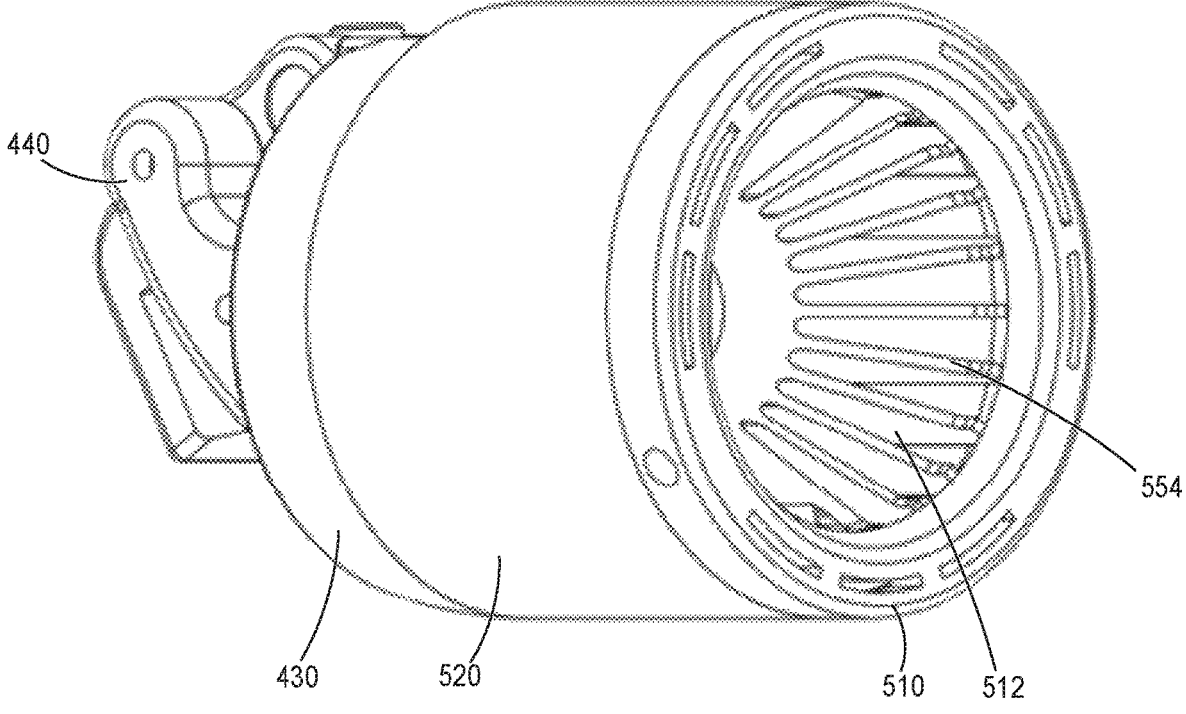
FIG. 17A illustrates a perspective view of a first side of the surgical light of FIG. 16, in accordance with various embodiments.

With reference to FIG. 17A, a perspective view of a first side of the surgical light 500 is illustrated, in accordance with various embodiments. In various embodiments, the outer diameter surface of light body 520 may sit flush with rear cap 430. In various embodiments, the outer diameter surface of light body 520 may sit flush with bezel 510.

In some embodiments, bezel 510 comprises a structure that is configured to be aligned with the edge of lens 512 and that permits light radiating from the edges of lens 512 to be visible from an outside edge of bezel 510 (e.g., light is visible from at side surface of bezel 510). In some embodiments, the structure comprised in bezel 510 includes a plurality of holes. In some embodiments, the structure comprises an area of bezel 510 that is thinner than other portions of bezel 510. For example, bezel 510 at the structure is thinner than a thickness of bezel 510 at a distal end of the surgical light. The visibility of light from the outside circumference allows other surgical observers to identify that the surgical light is on/operating properly while a surgeon may be looking into a cavity or if the surgical area has a lot of environmental light thereby causing difficulty in perceiving whether the surgical light is on.

Figure 17B:
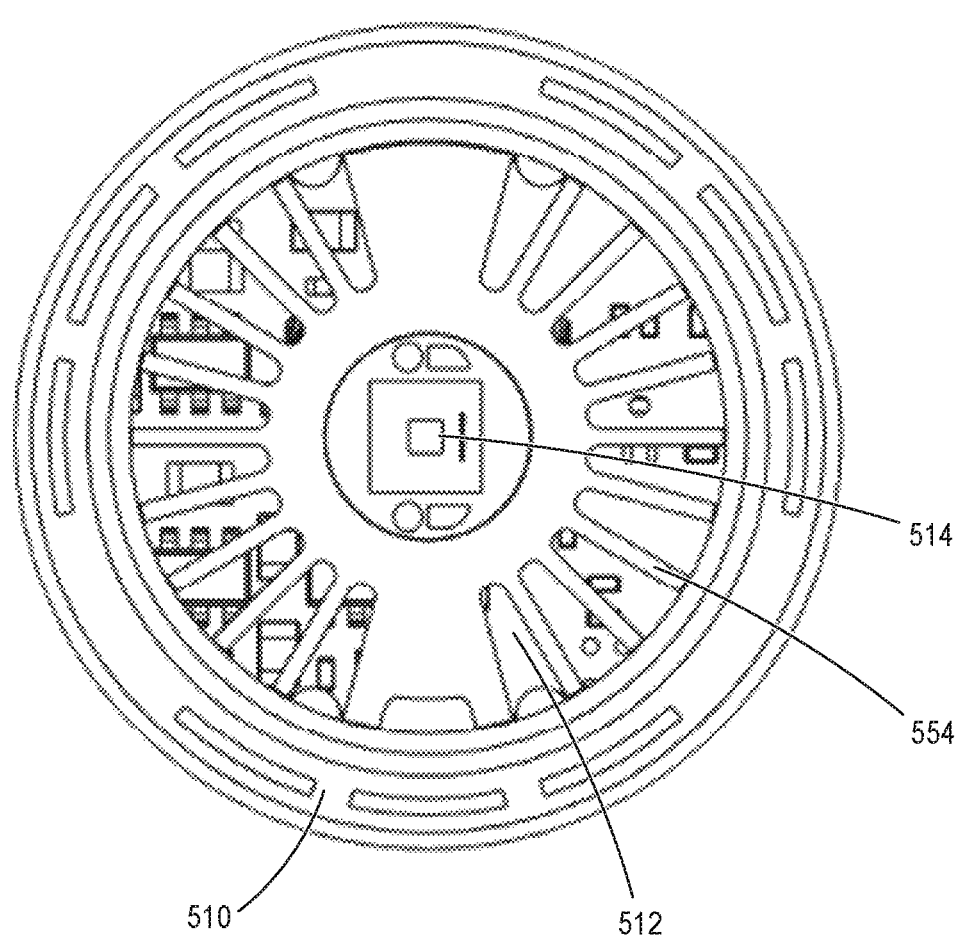
FIG. 17B illustrates a front view of the surgical light of FIG. 16, in accordance with various embodiments.

With reference to FIG. 17B, a front view of surgical light 500 is illustrated, in accordance with various embodiments. In various embodiments, the frustoconical shaped lens 512 may be centered around LED 514.

Figure 17C:
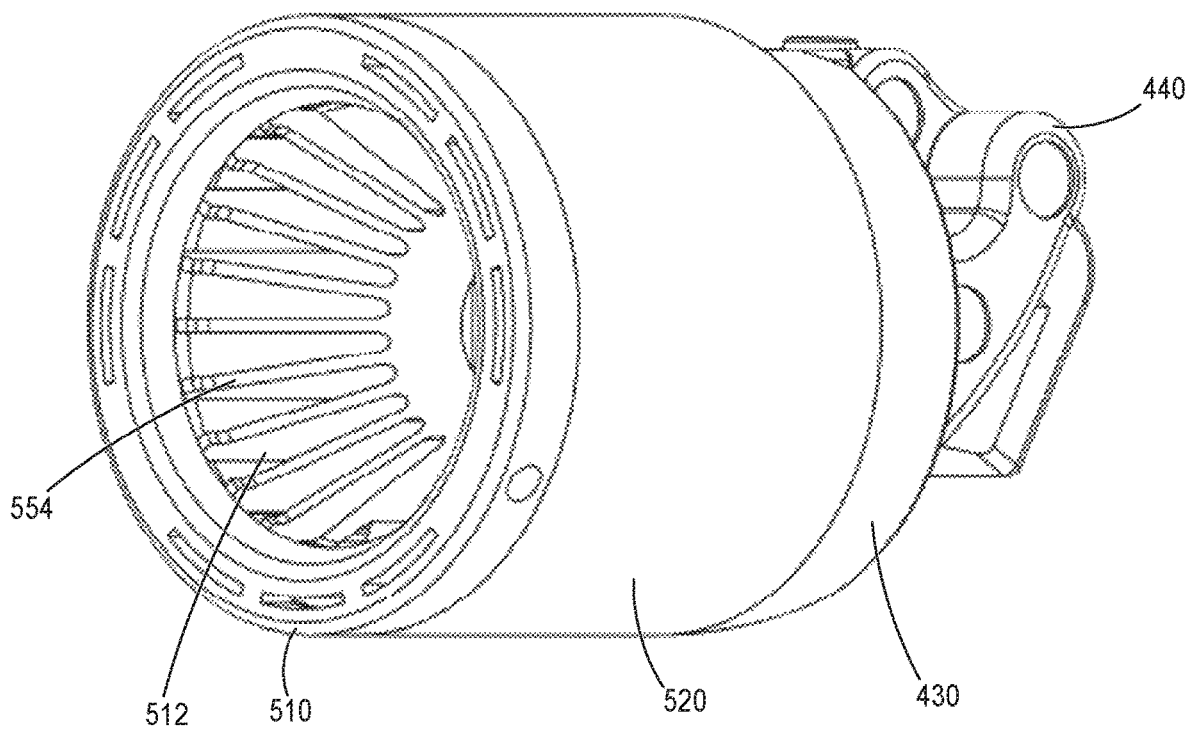
FIG. 17C illustrates a perspective view of a second side of the surgical light of FIG. 16, in accordance with various embodiments.

With reference to FIG. 17C, a perspective view of a second side (opposite the first side of FIG. 17A) of surgical light 500 is illustrated, in accordance with various embodiments.

Figure 17D:
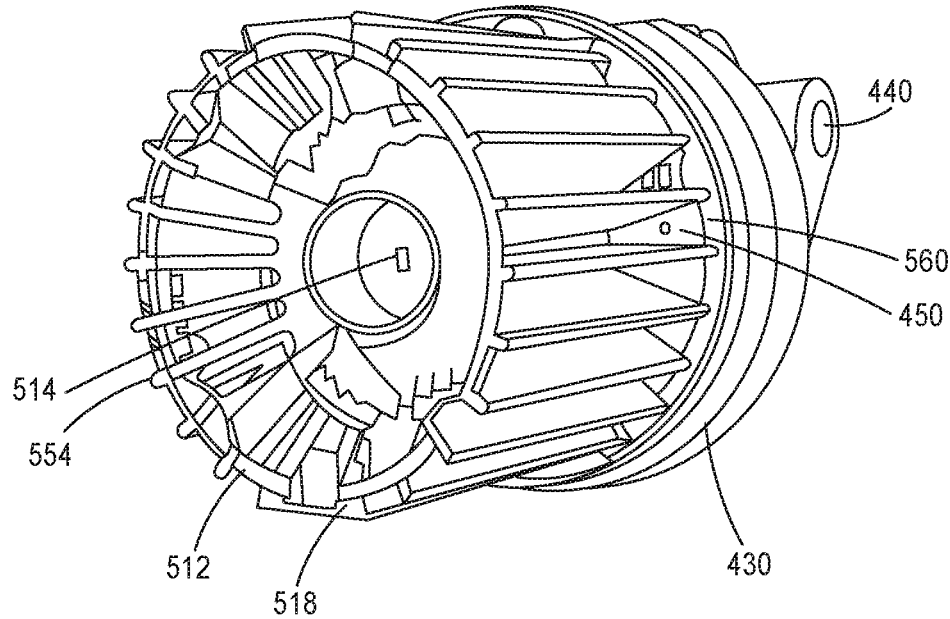
FIG. 17D illustrates the surgical light of FIG. 17C with the bezel and the light body removed for clarity purposes, in accordance with various embodiments.
Figure 17E:
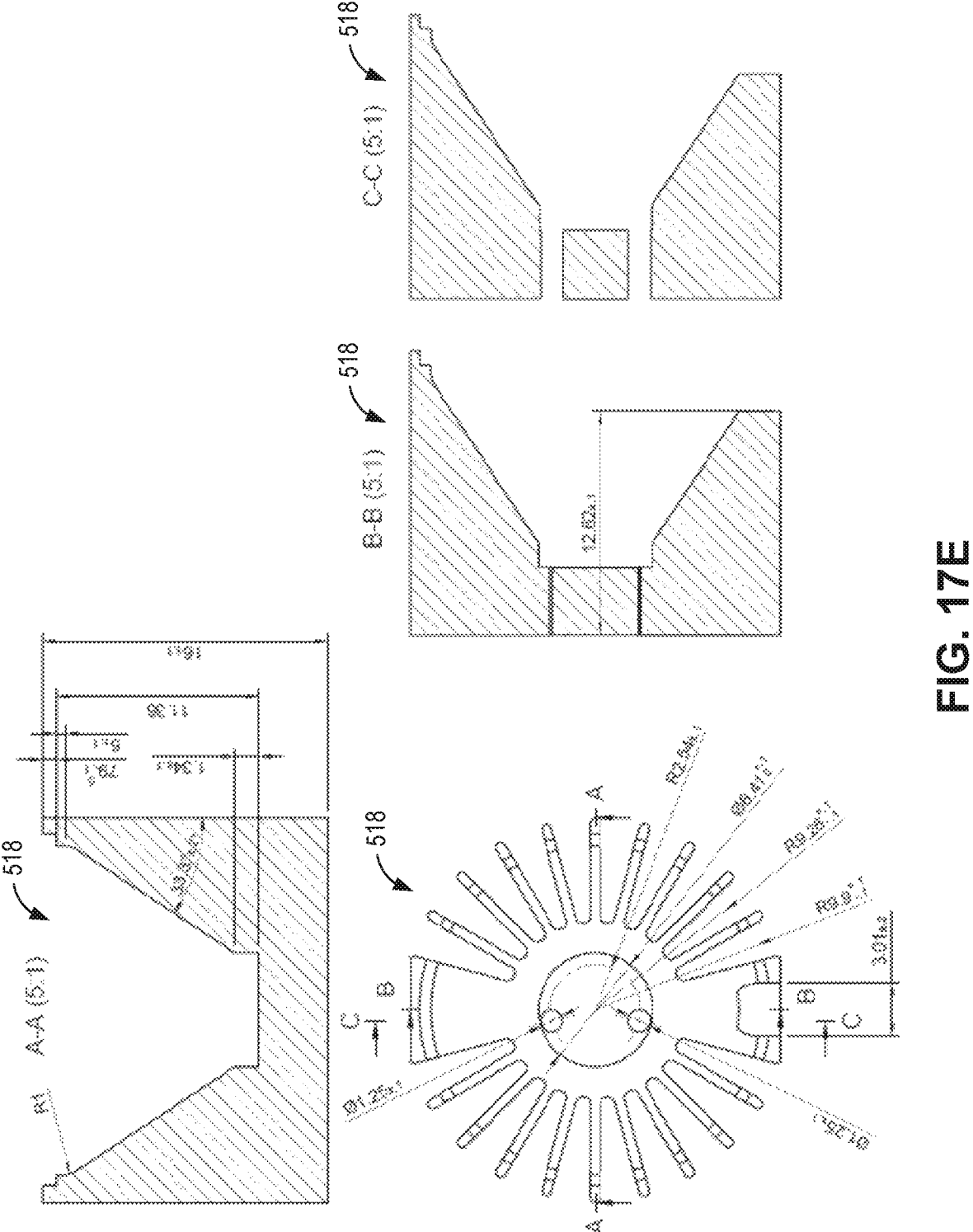
FIG. 17E illustrates section drawings of a thermal conductive heat sink of the surgical light of FIG. 17C, in accordance with various embodiments.

With reference to FIG. 17D, a perspective view of the second side of surgical light 500 is illustrated with the bezel 510 and the light body 520 removed for clarity purposes, in accordance with various embodiments. Fins 554 may at least partially surround lens 512 in the installed position. In various embodiments, lens 512 may seat against fins 554 in the installed position. In various embodiments, an outer lip of lens 512 may abut fins 554. In various embodiments, the forward side of support plate 560 may protrude slightly forward of the forward side of rear cap 430. In various embodiments, the rear side of fins 554 may be immediately adjacent the forward side of support plate 560.

With reference to FIG. 17D, front and section views of the heat sink 518 are illustrated, in accordance with various embodiments.

Figure 18A:
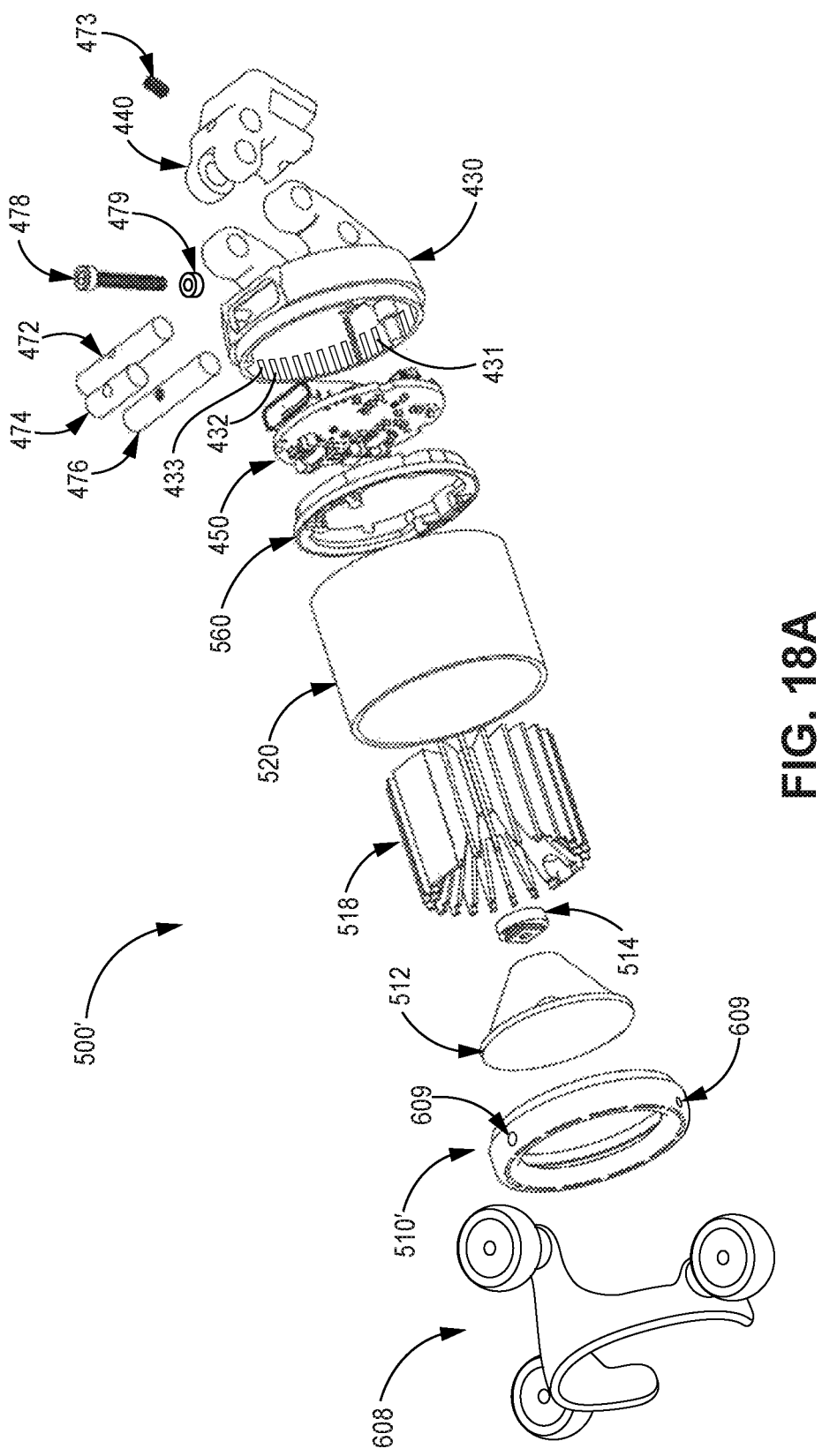
FIG. 18A illustrates an assembly view of a surgical light having a navigation collar of the present disclosure, in accordance with various embodiments.

With respect to FIG. 18A, elements with like element numbering, as depicted in FIG. 16, are intended to be the same and will not necessarily be repeated for the sake of clarity.

With reference to FIG. 18A, an assembly view of a surgical light 500' with a bezel 510' having a navigation, in accordance with various embodiments. Surgical light 500' may be similar to surgical light 500 (see FIG. 16). However, the bezel 510' of surgical light 500' may have structural differences from bezel 510. In particular, bezel 510' may include a plurality of dimples or detents 609 for securing navigation collar 608. Detents 609 may be disposed circumferentially around the outer surface of bezel 510'. Navigation collar 608 may include a plurality of bosses or tabs 607 (see FIG. 19B) configured to be received by detents 609 for securing navigation collar 608 to surgical light 500'.

Furthermore, surgical light 500' may include a collar 479 to help secure vertical adjustment member 478 captive within the top hinge pin 474 of the vertical adjustment assembly. Collar 479 may maintain the distance of the head of the adjustment member 478 relative to the top hinge pin 474 at all times. Collar 479 may be made of a metal or metal alloy, such as stainless steel for example. In practice, this collar 479 may be joined (e.g., welded) to the shaft of the adjustment member 478 once the adjustment member 478 is placed through the top hinge pin 474.

In the example shown in FIG. 18A, the inside walls of rear cap 430 comprises fluting. For example, rear cap 430 comprises a plurality of grooves such as grooves 431, 432, 433 that extend from a distal end of rear cap 430 towards the proximal end of rear cap 430. The plurality of grooves may help define the plurality of pathways via which air is vented from heat sink 518 around the circuit board, and to the external environment via ports in rear cap 430 (e.g., ports in a rear surface of rear cap 430).

Figure 18B:
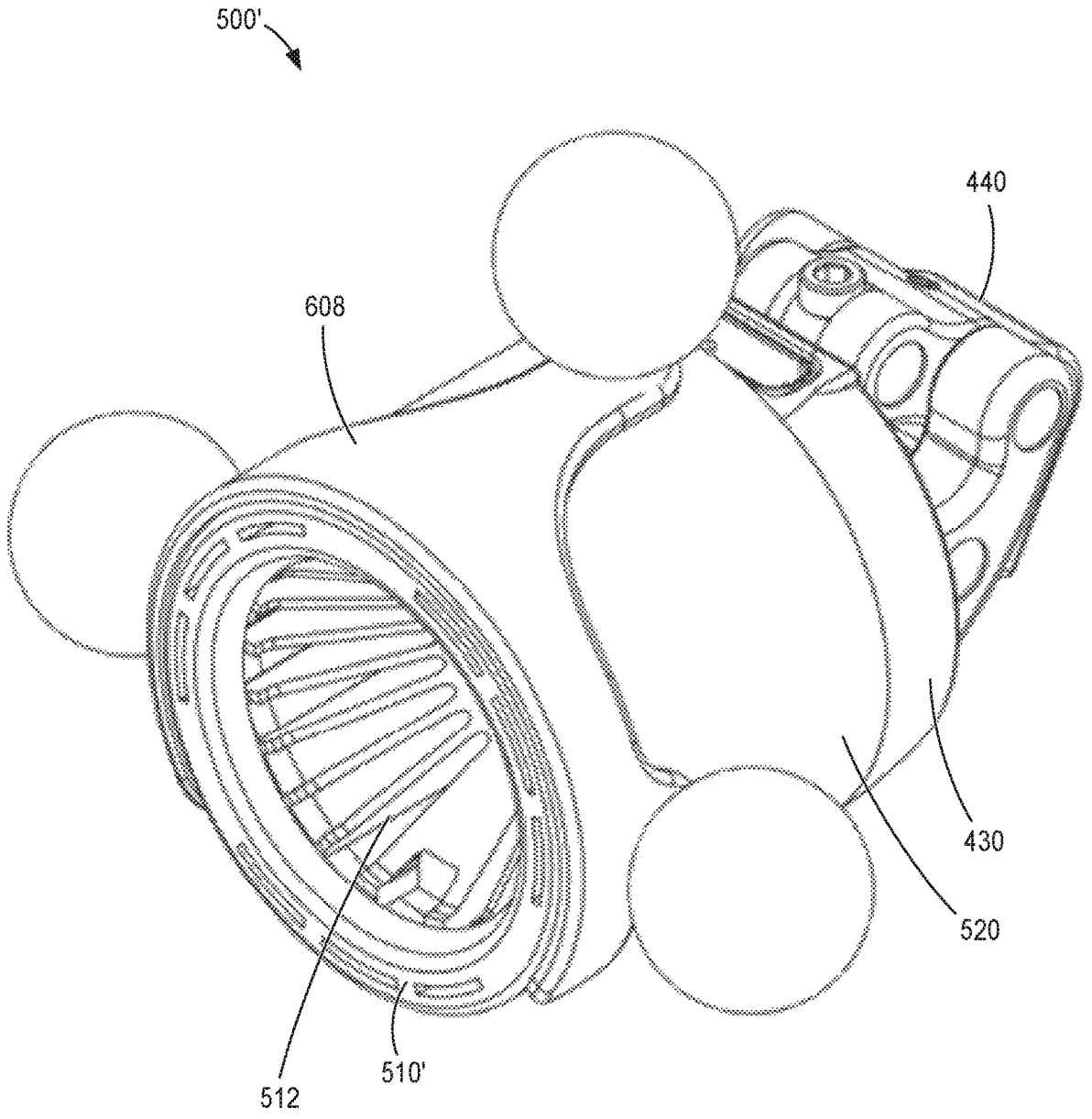
FIG. 18B illustrates a perspective view of the surgical light having the navigation collar of FIG. 18A of the present disclosure, in accordance with various embodiments.

With reference to FIG. 18B, a perspective view of navigation collar 608 installed onto surgical light 500'. Navigation collar 608 may be made from a plastic material. Navigation collar 608 may be easily installed and uninstalled from surgical light 500'. In particular, navigation collar 608 may snap on and off of the surgical light 500' to be used when convenient.

Figure 18C:
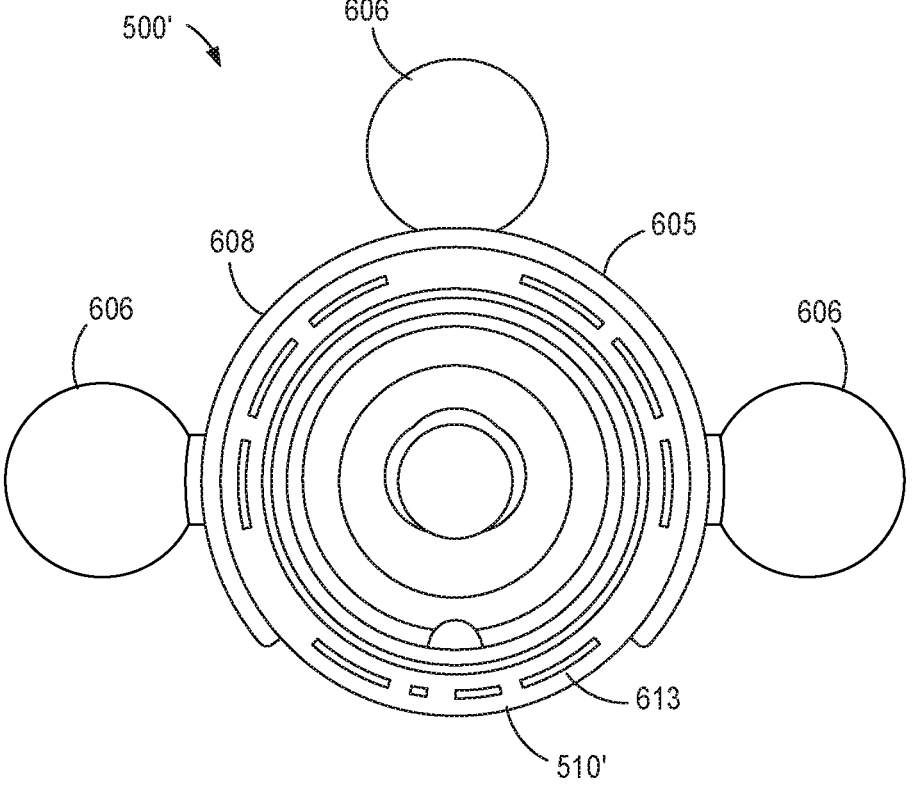
FIG. 18C illustrates a front view of the surgical light having the navigation collar of FIG. 18A of the present disclosure, in accordance with various embodiments.

With reference to FIG. 18C, a front view of surgical light 500' with navigation collar 608 installed thereon. Navigation collar 608 may comprise a geometry or form that conforms closely to the outer surface of bezel 510'. Navigation collar 608 may comprise a collar portion 605 that extends around a portion of bezel 510'. Collar portion 605 may extend between 180° and 360° around bezel 510' in various embodiments, between 180° and 300° around bezel 510' in various embodiments, and between 180° and 270° around bezel 510' in various embodiments. In this manner, collar portion 605 may be configured to flex radially outward to remove tabs 607 from detents 609 to remove navigation collar 608 from surgical light 500'.

Bezel 510' may comprise a plurality of radial vents 613 disposed circumferentially around bezel 510' and terminating at a forward surface thereof. The circumferential location of each detent 609 may be devoid of a radial vent 613 to provide structural support to the tabs 607 on the navigation collar 608. In some embodiments, the plurality of radial vents 613 permit air to travel into the surgical light, passed heat sink 518, and through the pathways through/around the circuit for venting at a rear of the surgical light.

Figure 18D:
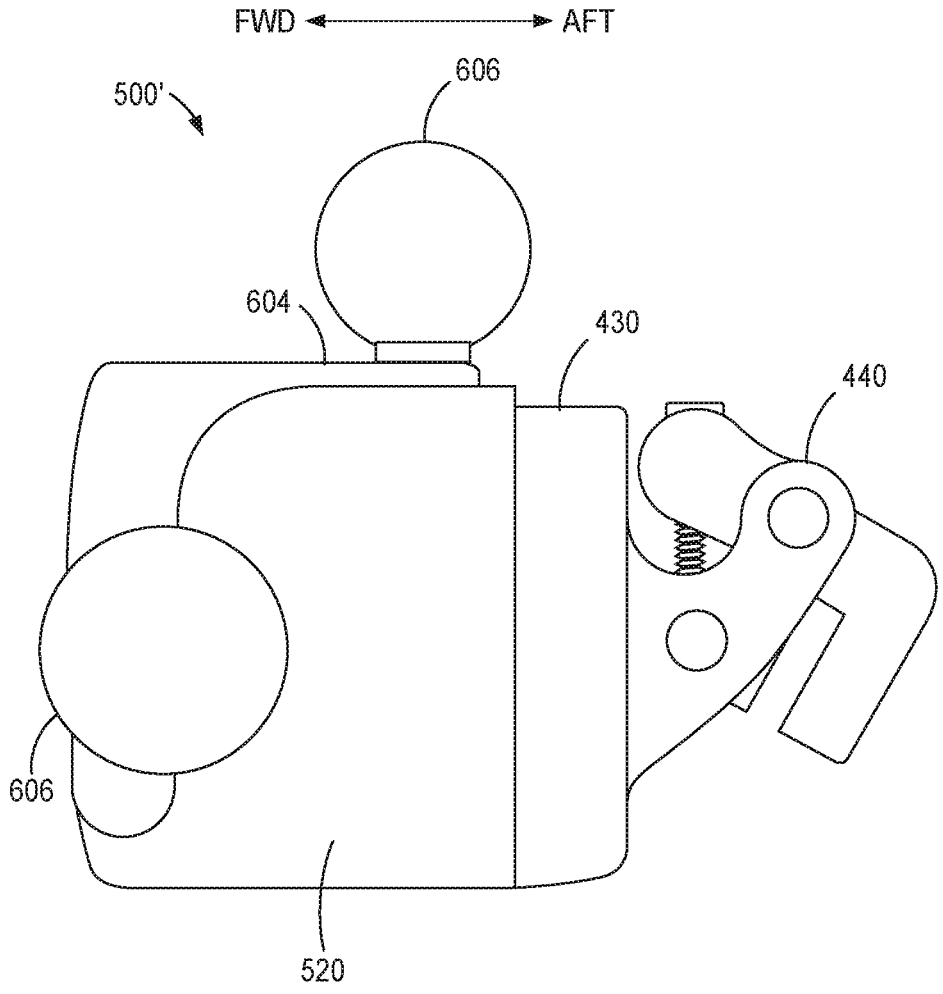
FIG. 18D illustrates a side view of the surgical light having the navigation collar of FIG. 18A of the present disclosure, in accordance with various embodiments.

With reference to FIG. 18D, a side view of surgical light 500' with navigation collar 608 installed thereon. Navigation collar 608 may further comprise an extension portion 604 that extends longitudinally aft from collar portion 605 and bezel 510'. In various embodiments, extension portion 604 extends over light body 520.

Navigation collar 608 may further comprise a plurality of reflective markers 606. Reflective markers 606 may be spherically shaped balls. Two of the reflective markers 606 may be attached to the collar portion 605 at opposite sides of bezel 510' and a third reflective marker may be attached to extension portion 604 and located aft from the other two reflective markers. Other arrangements of the reflective markers 606 are contemplated, including moving the front most pair of reflective markers 606 lower or higher to improve vision around these areas.

Figure 18E:
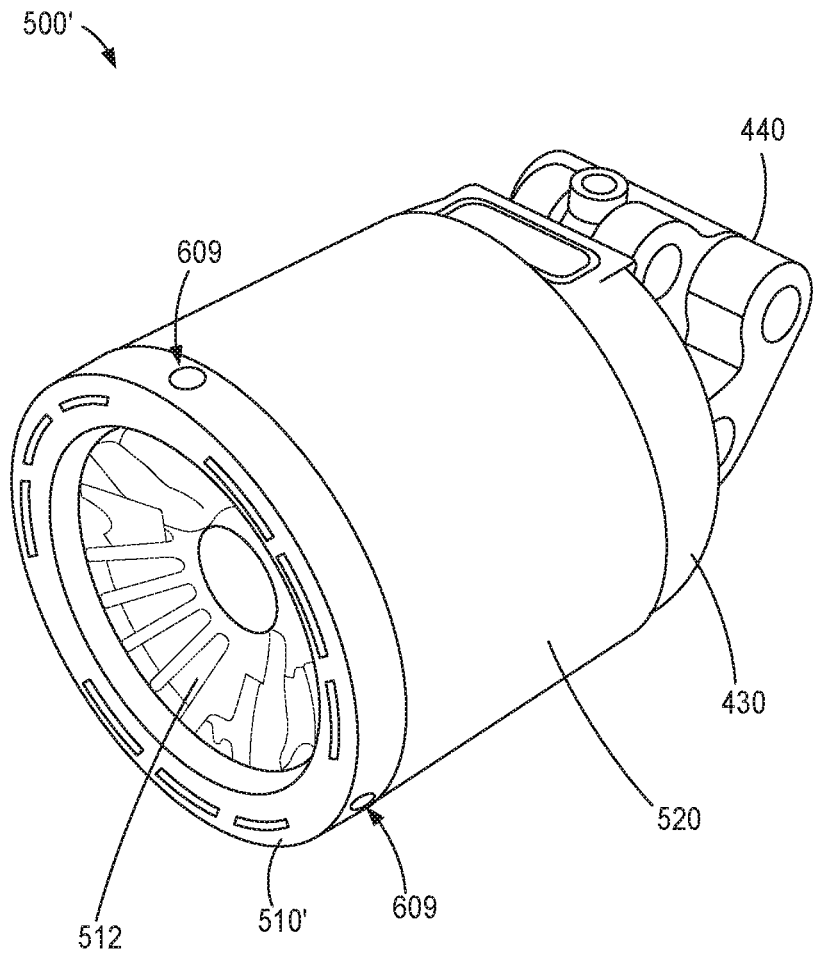
FIG. 18E illustrates a perspective view of the surgical light of FIG. 18A with the navigation collar omitted, in accordance with various embodiments.

With reference to FIG. 18E, a perspective view of surgical light 500' with the navigation collar 608 removed.

Figure 19A:
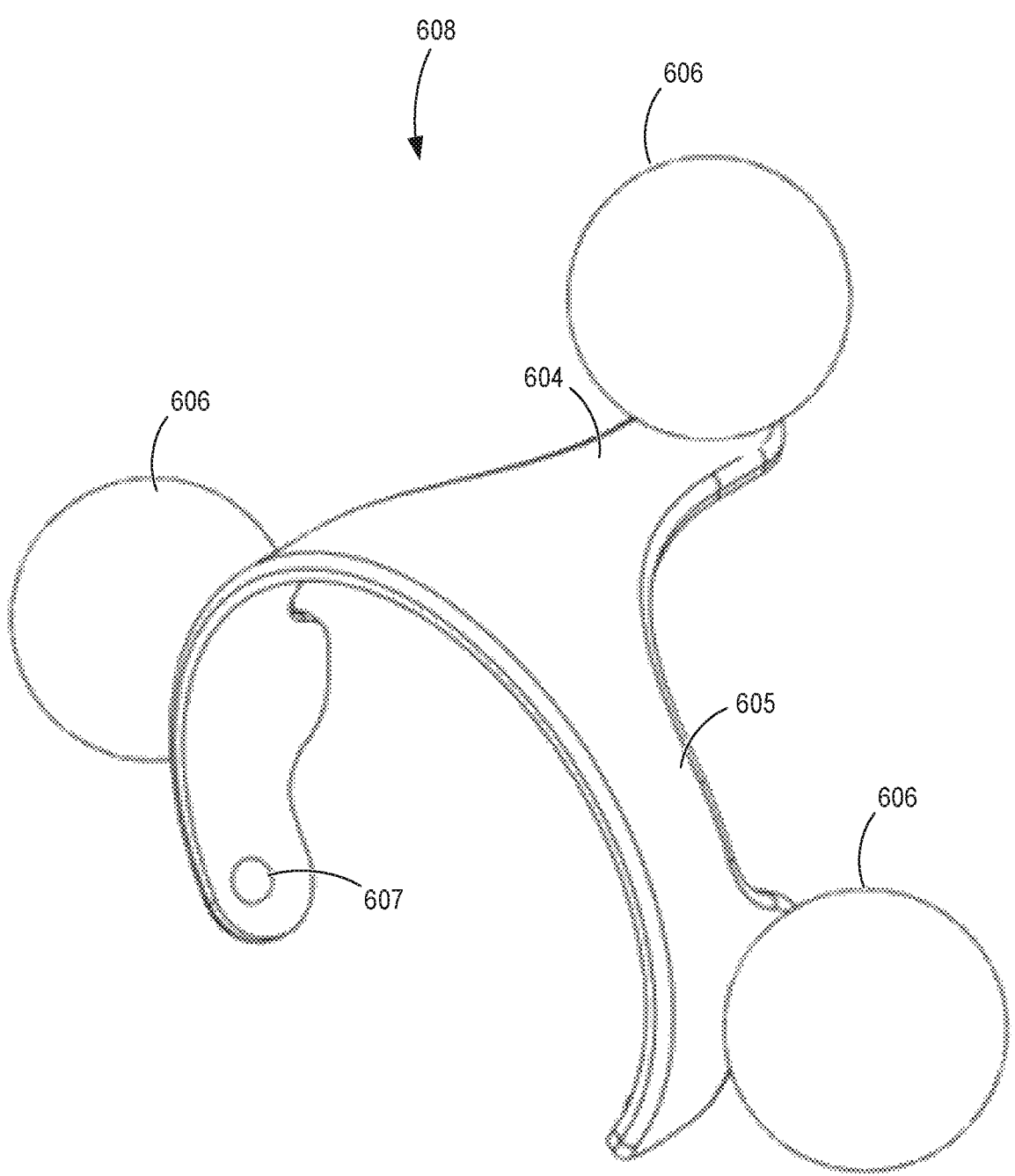
FIG. 19A illustrates a perspective view of the navigation collar for the surgical light of FIG. 18A, in accordance with various embodiments.
Figure 19B:
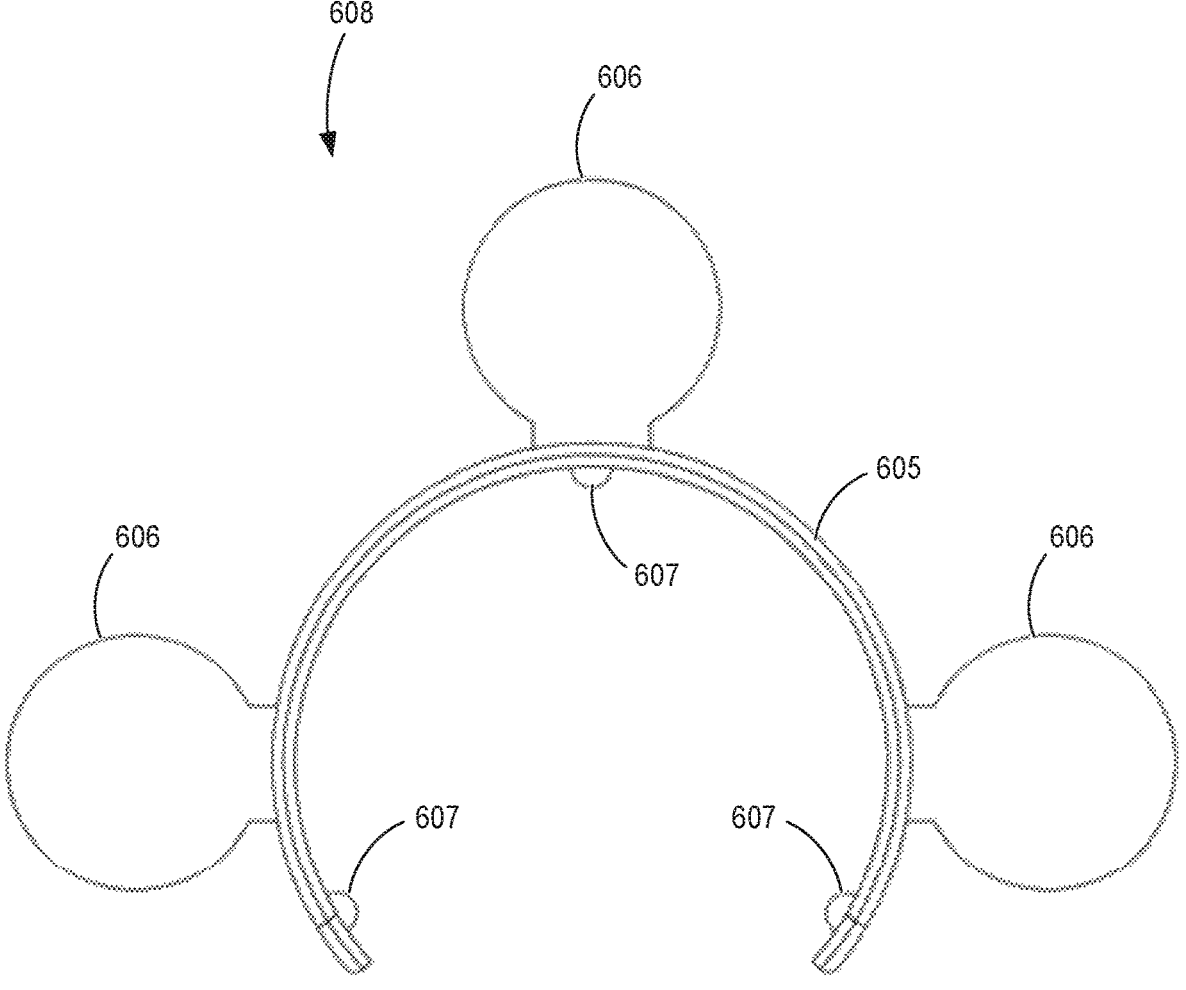
FIG. 19B illustrates a front view of the navigation collar of FIG. 19A, in accordance with various embodiments.
Figure 19C:
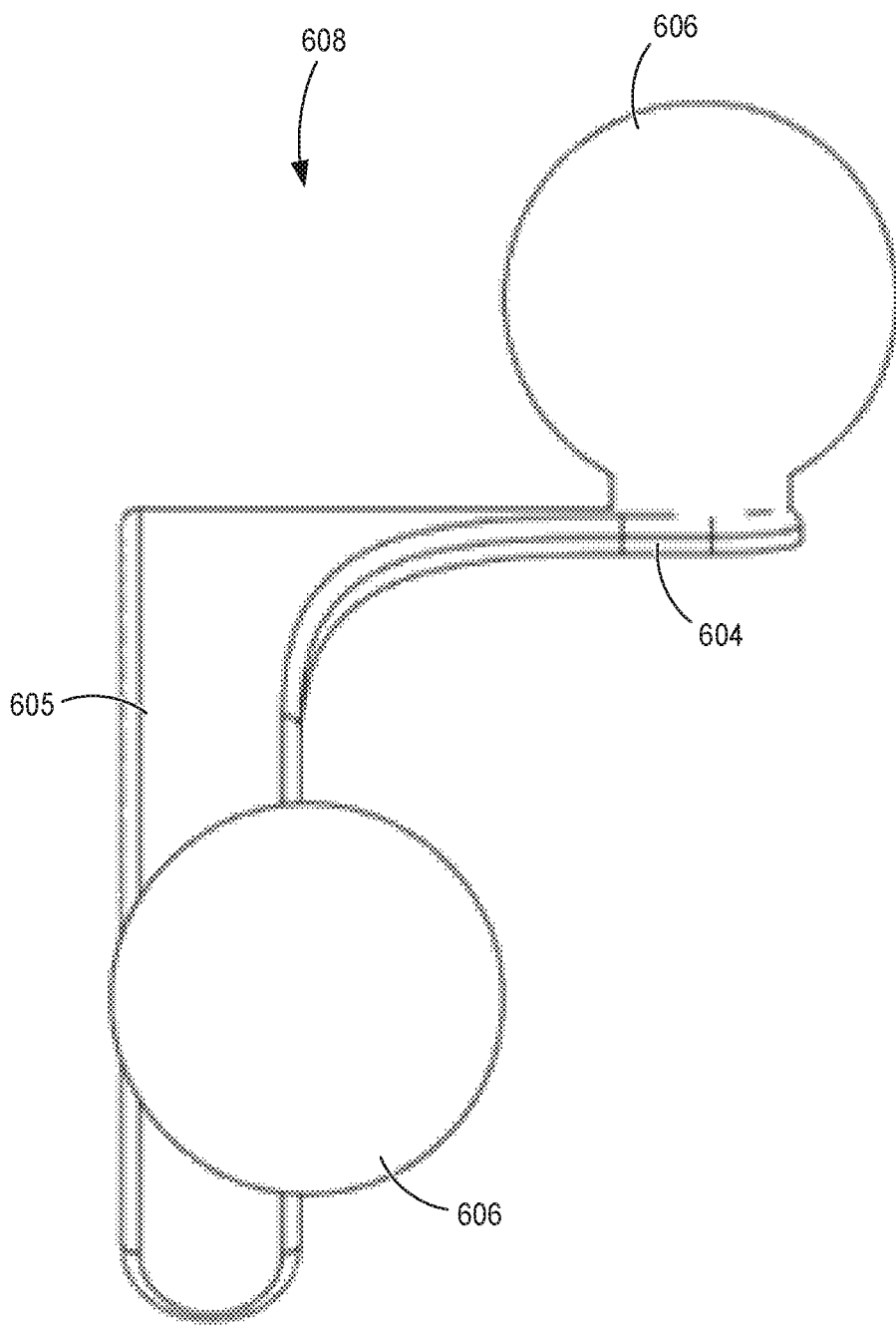
FIG. 19C illustrates a side view of the navigation collar of FIG. 19A, in accordance with various embodiments.

With reference to FIG. 19A through FIG. 19C, perspective, front, and side views of navigation collar 608 are illustrated, respectively. Tabs 607 may comprise hemispherical geometries. Tabs 607 may aid in registering the navigation collar 608 with the bezel 510' to maintain alignment during navigation. Reflective markers 606 may be removal and disposable. Reflective markers 606 may be snapped in place, screwed in place, or the like.

Figure 20:
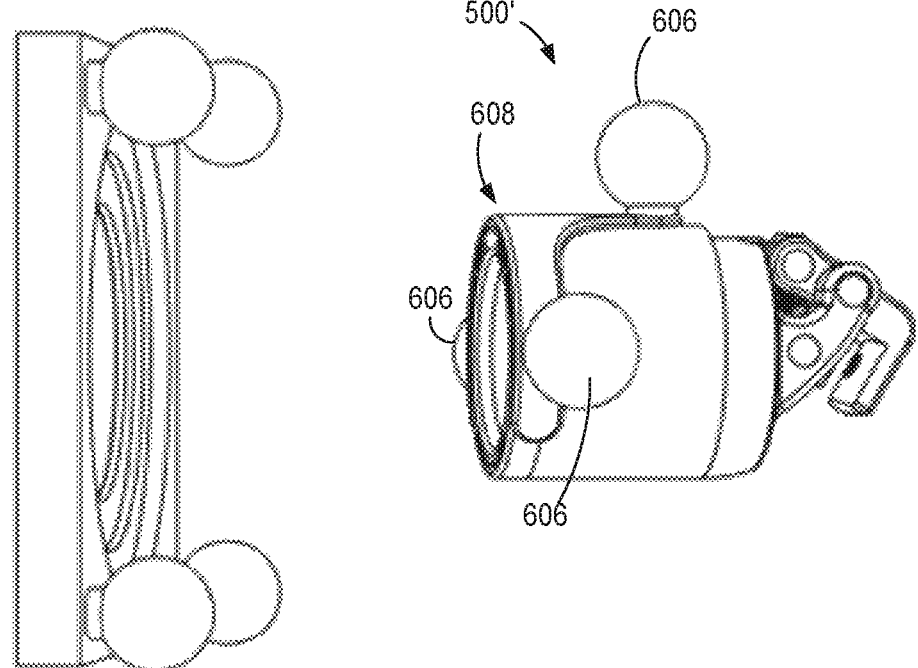
FIG. 20 illustrates a surgical light with the navigation collar calibrated with a navigation system, in accordance with various embodiments.

With reference to FIG. 20, a method of calibrating an operative navigation system may include equipping the surgical light 500' with navigation collar 608. The reflective markers 606 may be registered with an infrared camera while the surgical light 500' is pointing at a target. The operator positions the beam of light from surgical light 500' such that it is at the center of the target. The surgical light 500' may send an output to the navigation system (e.g., through Bluetooth) to communicate that it is centered on the target and to complete the calibration. This information will allow the navigation system to know where the surgical light 500', and consequently, the surgeon perspective is relative to the patient anatomy. In this way, a proposed target and trajectory can be drawn in the navigation system relative to the patients scanned imaging (a volume). The surgical light 500' can be found in space relative to the patient anatomy and surgical plan and can be used to change the viewing perspectives in the navigation software and associated screen and can also provide the surgeon feedback when his surgical light 500' and line of sight is aligned with a proposed surgical target and trajectory. This design may be incorporated into various surgical lights of the present disclosure.

Figure 21:
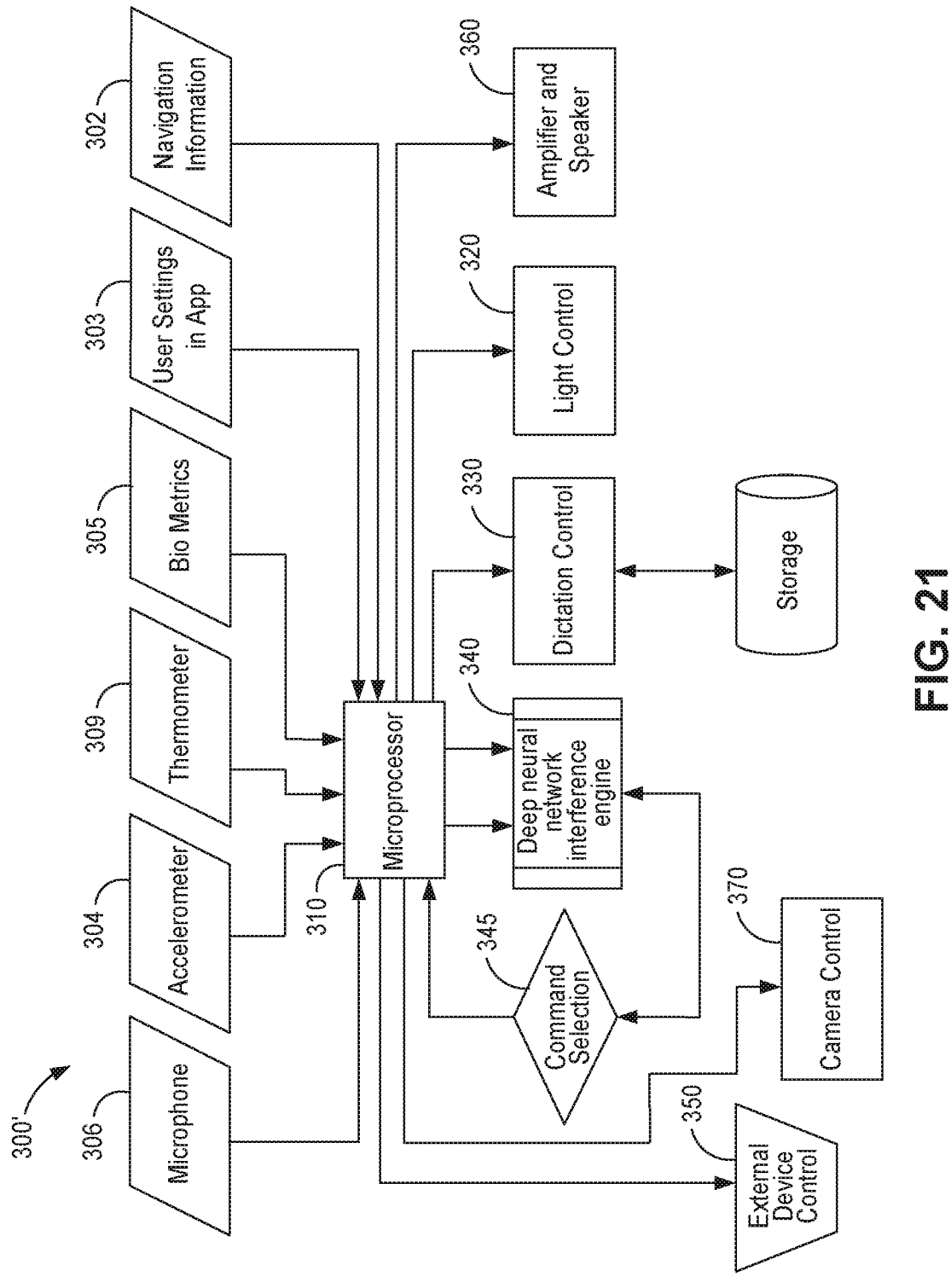
FIG. 21 illustrates a block diagram of a light control system for a surgical light of the present disclosure, in accordance with various embodiments.

With respect to FIG. 21, elements with like element numbering, as depicted in FIG. 14, are intended to be the same and will not necessarily be repeated for the sake of clarity.

With reference to FIG. 21, a block diagram of a control system 300' for a surgical light is illustrated, in accordance with various embodiments. Control system 300' may be similar to control system 300. Control system 300' further receives as an input navigation information 302. The navigation unit (e.g., control system 300') may know the surgical light position by the reflective markers 606 and may receive feedback (i.e., navigation information 302) from the surgical light. The surgical light may communicate with the navigation system by Bluetooth, or via an application running on a mobile device, such as a smartphone paired with the surgical light, etc. An amplifier and speaker 360 (e.g., audio output amplifier 202) may also be included onboard the PCB of the surgical light to provide feedback to the wearer. Control system 300' may further include a camera control 370.

Figure 22A:
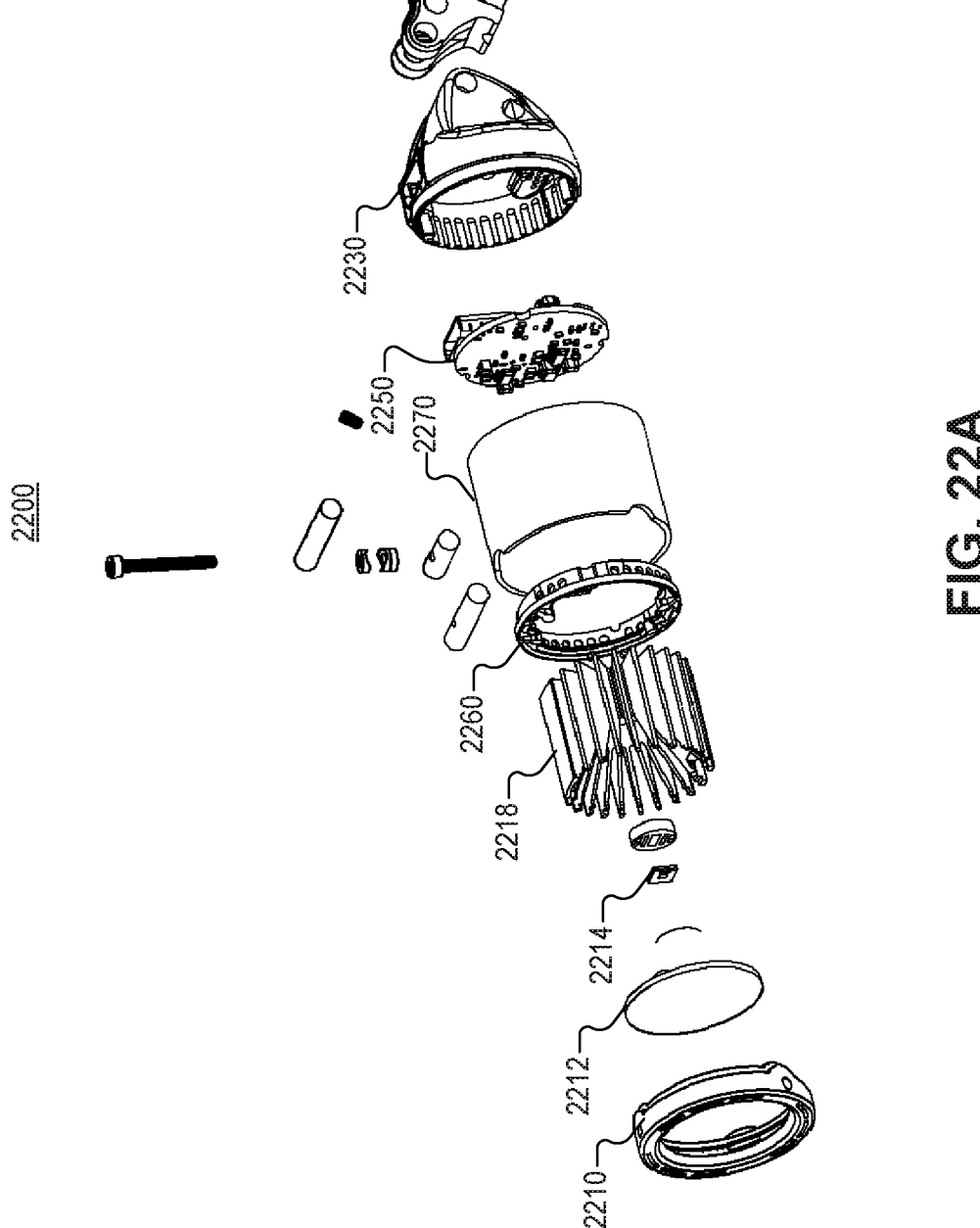
FIG. 22A illustrates an assembly view of a surgical light in accordance with various embodiments.

FIG. 22A illustrates an assembly view of a surgical light in accordance with various embodiments. Surgical light 2200 includes various elements which are similar to, or correspond to, the elements described in connection with FIGS. 15, 16, and 18A. In the example shown, surgical light 2200 includes light source 2214 (e.g., one or more LEDs) and a housing.

In some embodiments, the housing includes thermal insulating shell 2720. In various embodiments, the housing may include bezel 2210 and rear cap 2230. One or more of bezel 2210 and rear cap 2230 may include a port(s) via which air is dissipated/vented.

In the example shown, surgical light 2200 includes bezel 2210, lens 2212, light source 2214, heat sink 2218, support structure 2260 (e.g., which may be similar to the support plate described herein, such as support plate 560), thermal insulating shell 2270, circuit board 2250, and rear cap 2230.

In some embodiments, surgical light 2200 comprises a plurality of pathways (e.g., heat conductive pathways) via which heat is vented from surgical light 2200. In the example shown, air may be vented through one or more ports in the bezel or rear cap. For example, bezel 2210 may include a plurality of ports. As another example, rear cap 2230 may include a plurality of ports. Heat from the light source may be transferred to heat sink 2218. Heat from heat sink 2218 may be transferred to air flowing through surgical light 2200, and the air flows through one or more of the plurality of pathways. As an illustrative example, air may flow over heat sink 2218 and the air flows around (or in some cases, partly through) circuit board 2250 and exits through one or more ports in rear cap 2230.

In some embodiments, circuit board 2250 comprises one or more cutaways (e.g., through holes) via which air is vented through the ports comprised in rear cap 2230.

In some embodiments, support structure 2260 (e.g., a spacer) is configured to direct/guide air around or through circuit board 2250. As an example, rear cap 2230 may comprise fluting, such as a plurality of flutes/grooves configured on an inside wall, to direct air through a port in rear cap 2230 (e.g., a port in the proximal end/rear of rear cap 2230). Support structure 2260 directs air towards the fluting of rear cap 2230 and air may be carried around circuit board 2250. As an example, support structure 2260 comprises a substantially thermally insulative material, such as plastic. Support structure 2260 is configured to be thermally insulative material to avoid the transfer of heat (e.g., conducted via support structure 2260) from heat sink 2218 to circuit board 2250 and to promote cooling via venting.

Figure 22B:
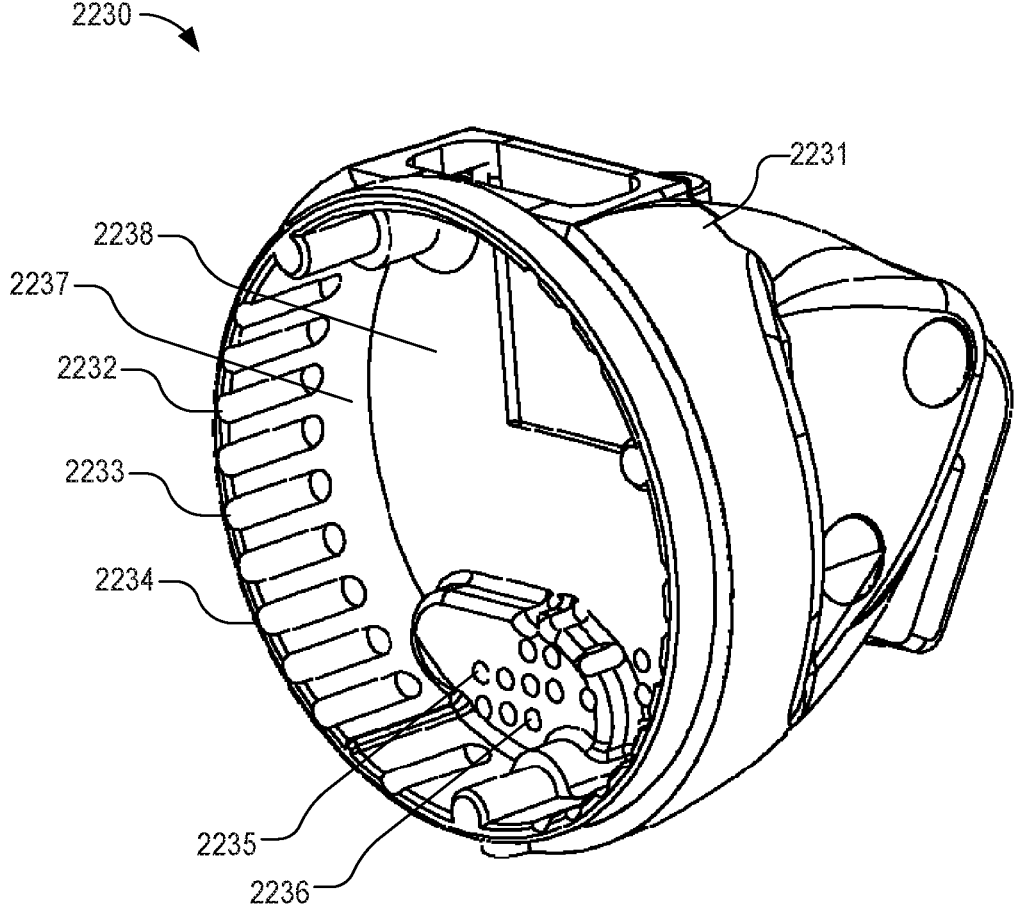
FIG. 22B illustrates a perspective view of a rear cap of a surgical light in accordance with various embodiments.

FIG. 22B illustrates a perspective view of a rear cap of a surgical light in accordance with various embodiments. As illustrated in FIG. 22B, an example of rear cap 2230 is provided.

In the example shown, rear cap 2230 comprises support structure 2231. Support structure 2231 may at least partly define the housing of surgical light 2200. In some embodiments, support structure 2231 defines one or more pathways, such as to vent heat from ports in rear cap 2230 (e.g., ports 2235, 2236 in back wall 2238). For example, inner wall 2237 of support structure 2231 comprises a plurality of flutes (also referred to herein as grooves).

In some embodiments, the plurality of flutes extends from a front end of rear cap 2230 to a back wall 2238 of rear cap 2230. In some embodiments, the plurality of flutes extends a partial distance between the front end of rear cap 2230 and back wall 2238. For example, in the example shown, flutes 2232, 2233, and 2234 extend from a front end of rear cap 2230, such as where support structure 2260 directs air for venting, to a distance between the front end and back wall 2238. In some embodiments, the fluting is configured for the flutes to extend sufficiently far towards rear cap 2230 to carry air from heat sink 2218 to an area that is past/behind circuit board 2250.

Figure 22C:
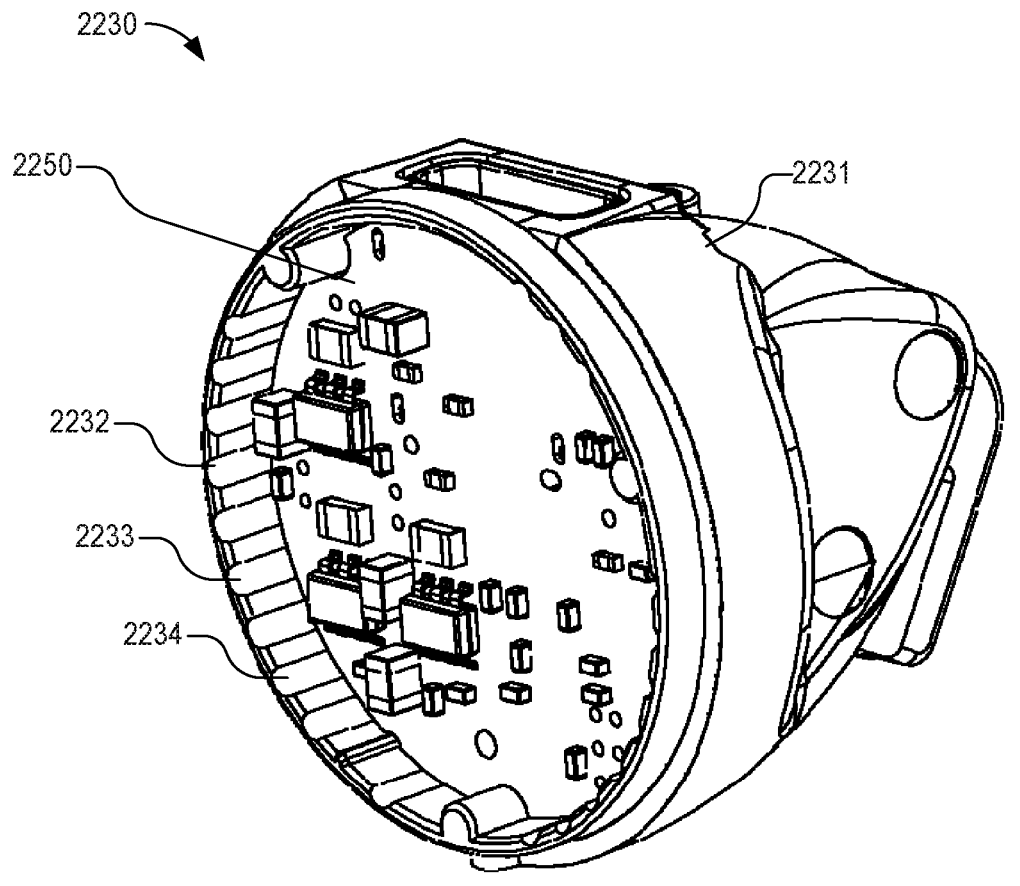
FIG. 22C illustrates a perspective view of a rear cap of a surgical light in accordance with various embodiments.

FIG. 22C illustrates a perspective view of a rear cap of a surgical light in accordance with various embodiments. As illustrated in FIG. 22C, an example of rear cap 2230 is provided in which circuit board 2250 is disposed within support structure 2231. In the example shown, circuit board 2250 is disposed within support structure 2231 sufficiently close to back wall 2238 for flutes 2232, 2233, and 2234 begin at the front of circuit board 2250 and extend to behind circuit board 2250.

Figure 22D:
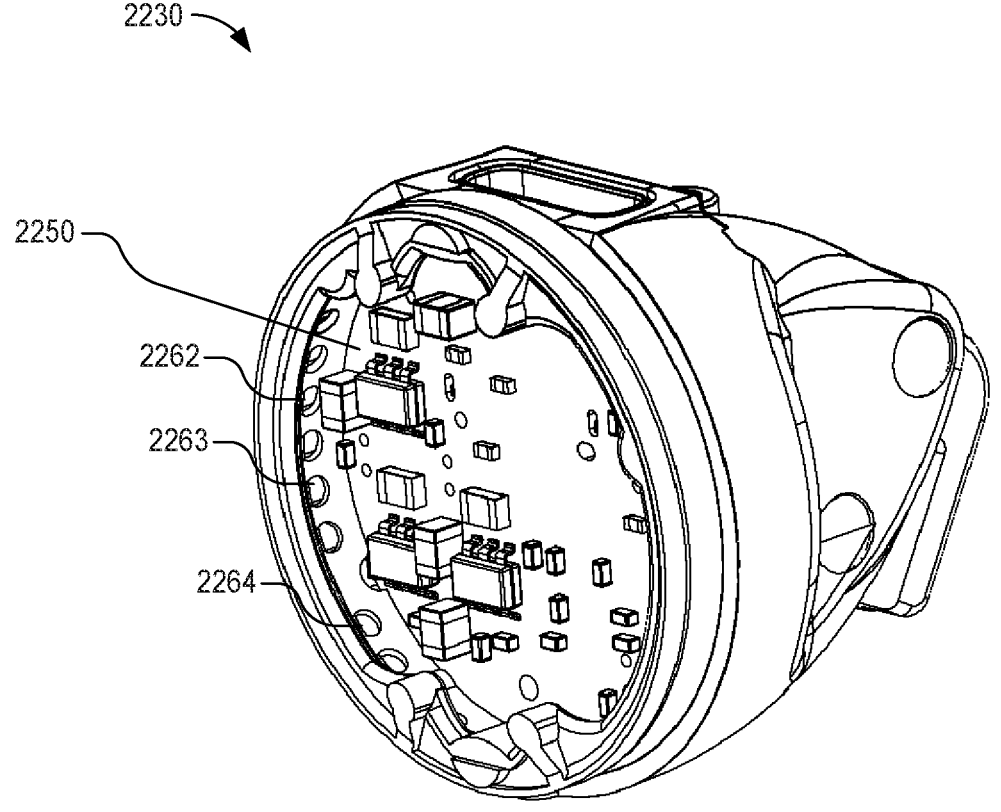
FIG. 22D illustrates a perspective view of a rear cap of a surgical light in accordance with various embodiments.

FIG. 22D illustrates a perspective view of a rear cap of a surgical light in accordance with various embodiments. As illustrated in FIG. 22D, an example of rear cap 2230 is provided in which support structure 2260 (e.g., the spacer) is placed over circuit board 2250. For example, support structure is disposed at a point more distal than circuit board 2250. In some embodiments, support structure 2260 is configured to, at least partly, direct heat around circuit board 2250. For example, support structure comprises ports 2262, 2263, and 2264 in a side wall to promote venting via the fluting in rear cap 230.

FIGS. 22E-H illustrate views of a bezel of a surgical light in accordance with various embodiments. As illustrated in FIGS. 22E-H, an example of bezel 2210 is provided.

Figure 22E:
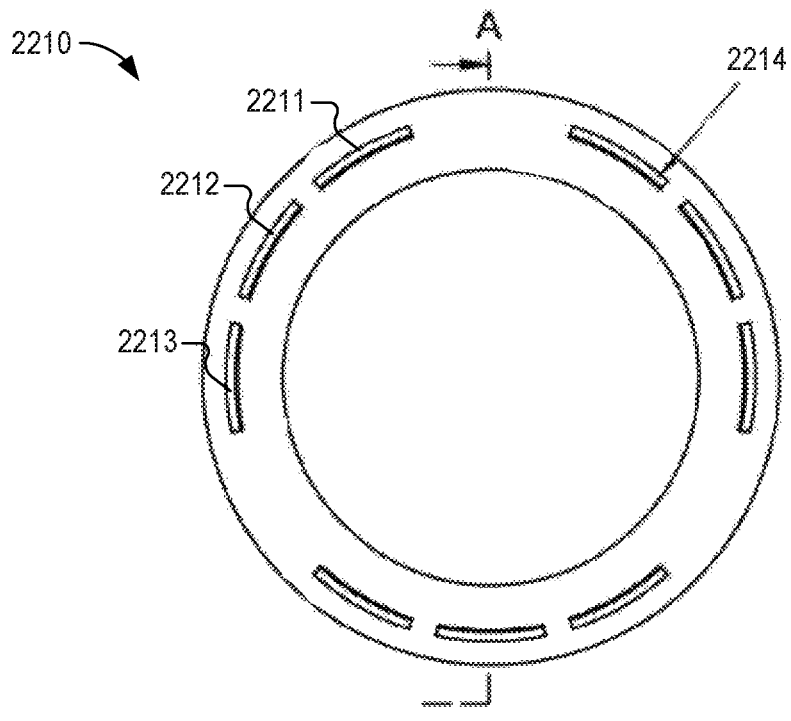
FIGS. 22E-H illustrate views of a bezel of a surgical light in accordance with various embodiments.

FIG. 22E is a front view of bezel 2210. In some embodiments, bezel 2210 comprises one or more ports via which air flows, such as in connection with dissipating heat from heat sink 2218. In the example shown, bezel 2210 comprises bezels 2211, 2212, 2213, and 2214.

Figure 22F:
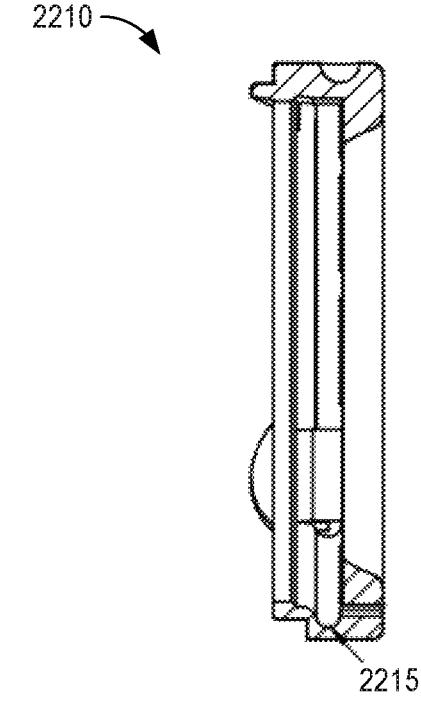

FIG. 22F is a cross-sectional view of bezel 2210 along axis A. In some embodiments, bezel 2210 comprises a structure that enables light emitted by lens 2212 to be viewable at sides of bezel 2210. For example, bezel 2210 transmits at least part of the light emitted by the edge(s) of lens 2212. In the example shown, bezel 2210 includes groove 2215 at an inner side wall of bezel 2210. The groove 2215 may be configured so that at least part of the inner side wall is sufficiently thin for light emitted by lens 2212 to be viewable from the external environment of surgical light 2200.

Figure 22G:
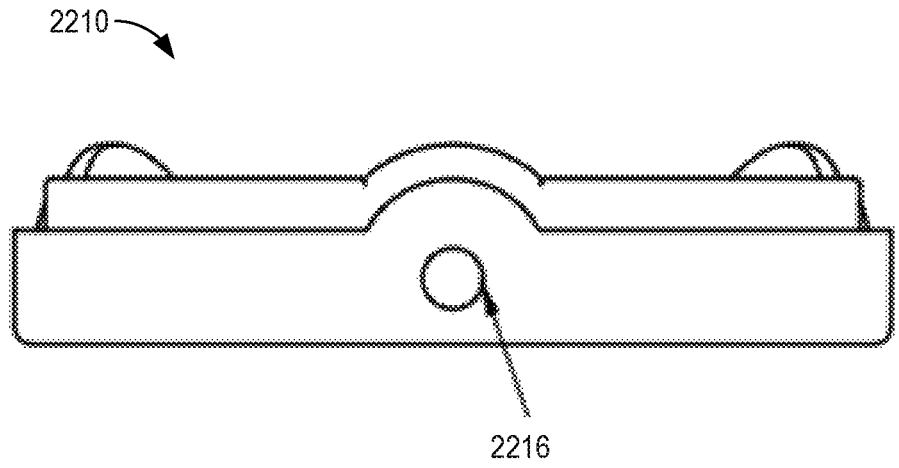

FIG. 22G is a side view of bezel 2210 along axis A. In some embodiments, bezel 2210 comprises one or more structures to which a navigation collar, such as navigation collar 608 of FIG. 18B, is mounted. In the example shown, bezel 2210 comprises detent 2216 on an exterior side wall. A navigational collar may be mounted to bezel 2210 using corresponding structures that interface with the one or more detents. For example, the navigational collar may have one or more protrusions that are inserted into the detent(s) when mounted.

Figure 22H:
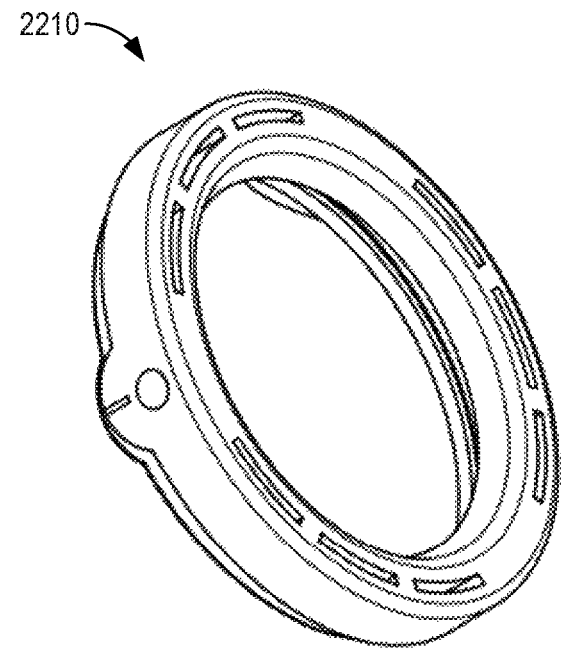

FIG. 22H is a perspective view of bezel 2210.

Figure 23:
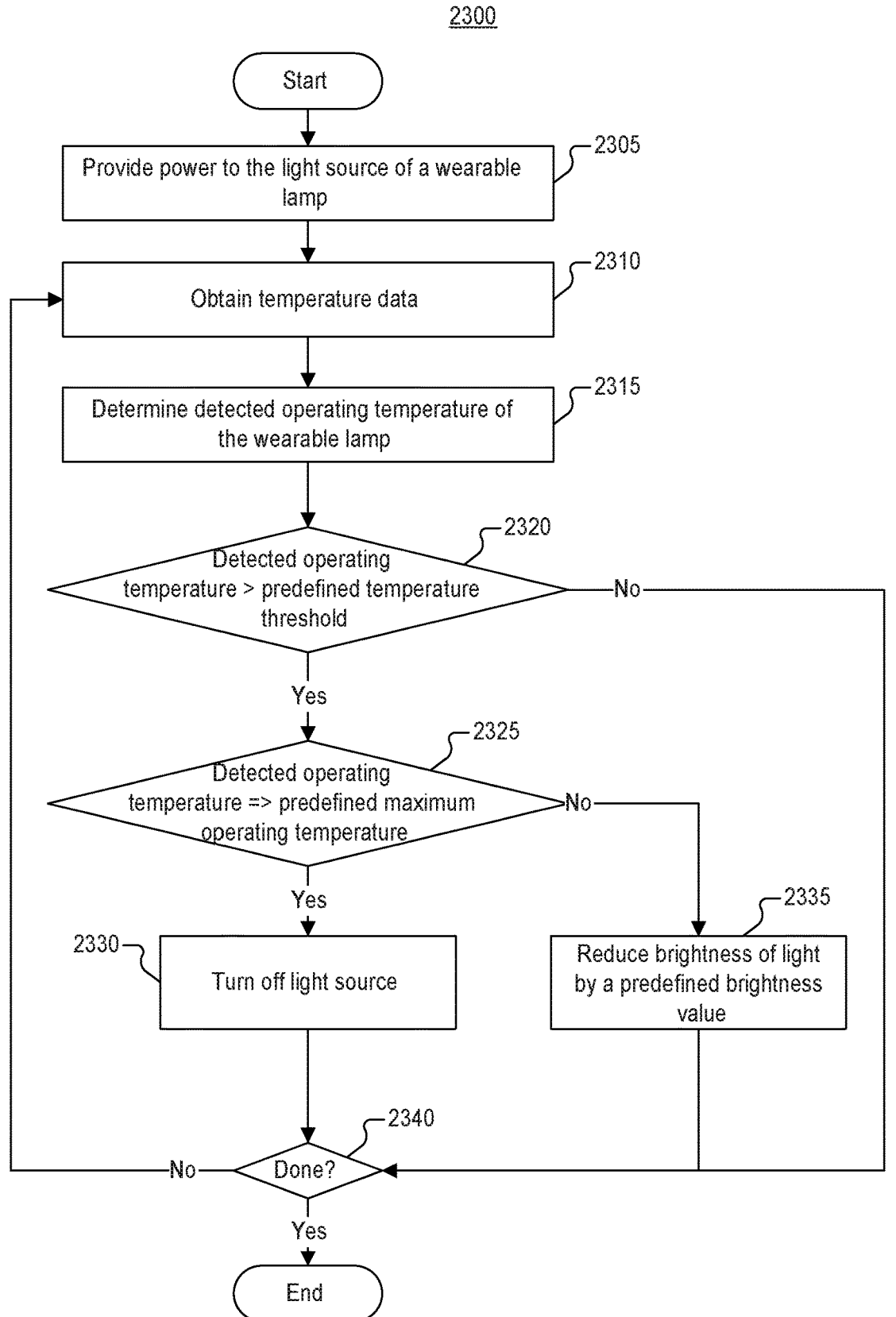
FIG. 23 illustrates a flow diagram of a method for controlling a wearable lamp based at least in part on detected temperature according to various embodiments.

FIG. 23 illustrates a flow diagram of a method for controlling a wearable lamp based at least in part on detected temperature according to various embodiments. In various embodiments, process 2300 is implemented by a processor comprised in the wearable lamp.

At 2305, power is provided to the light source of a wearable lamp. In some embodiments, the system provides power to the light source in response to the wearable lamp being turned on.

At 2310, temperature data is obtained. In some embodiments, the system obtains the temperature data via a heat sensor (e.g., a thermometer, a thermocouple, etc.). The temperature data may substantially serve as a proxy for the temperature at the circuit board, or temperature at which the components on the circuit board are operating. The heat sensor may be disposed on the circuit board, the heat sink, or another location within the wearable lamp according to which a detected temperature is substantially a proxy for the heat at the circuit board. In some embodiments, the heat sensor may be disposed in the surgical light at a location where the temp sensor monitors temperature that is substantially a proxy for the temperature of the light source junction (e.g., the LED junction). For example, the heat sensor may be disposed on or around the heat sink to monitor heat sink temperature, which the system uses as being indicative of the temperature of the light source junction.

At 2315, the system determines a detected operating temperature of the wearable lamp based at least in part on the temperature data. In response to obtaining the temperature data, the system determines a detected operating temperature of the wearable device. For example, the system may convert (e.g., according to a predefined conversion function) the temperature data to a temperature under which the components on the circuit board are operating.

At 2320, the system determines whether the detected operating temperature is greater than a predefined temperature threshold. In response to determining the detected operating temperature, the system compares the detected operating temperature to one or more predefined thresholds. The predefined thresholds may be configurable by a user such as based on user settings for temperatures at which the brightness of the light source is to be changed (e.g., to maintain a safe operating temperature and/or to avoid overheating of the components on the circuit board).

In various embodiments, the system stores a plurality of predefined temperature thresholds against which the system compares the detected operating temperature in order to provide the system with granular control for adjusting the light source responsive to changing operating temperatures. As an example, the system uses the predefined temperature thresholds in connection with changing/regulating an amount of light emitted from the wearable lamp in a manner that a change to the light is substantially imperceptible to the human eye.

In some embodiments, a first predefined temperature threshold is 70 degrees Celsius. For example, the system begins regulating the brightness of the light source when the detected operating temperature reaches 70 degrees Celsius.

In response to determining that detected operating temperature is greater than the predefined temperature threshold at 2320, process 2300 proceeds to 2325 at the system determines if the detected operating temperature is greater than or equal to a predefined maximum operating temperature. In some embodiments, the predefined maximum operating temperature is between 75 and 85 degrees Celsius. In some embodiments, the predefined maximum operating temperature is 80 degrees Celsius.

In response to determining that the detected operating temperature is greater than or equal to a predefined maximum operating temperature at 2325, process 2300 proceeds to 2330 at which the system turns the light source off. The system may use the predefined maximum operating temperature as a threshold according to which the light source is turned off to avoid overheating of the components on the circuit board (or elsewhere in the system). As an example, the predefined maximum operating temperature is 95% of the temperature that the circuit board or components thereon are able to withstand. As another example, the predefined maximum operating temperature is configurable, such as in accordance with user settings.

In response to determining that the detected operating temperature is not greater than or equal to a predefined maximum operating temperature at 2325, process 2300 proceeds to 2335 at which the system reduces the brightness of light by a predefined brightness value.

In response to determining that detected operating temperature is not greater than the predefined temperature threshold at 2320, process 2300 proceeds to 2340 at which the brightness of the light source is reduced. The system adjusts the light source in response to determining that the detected operating temperature is greater than a predefined temperature threshold and less than a predefined maximum operating temperature. In some embodiments, adjusting the brightness of the light emitted by the light source is performed by changing an amount of power used to drive the light source.

In some embodiments, the reducing the brightness of the light source includes reducing the brightness of light emitted by the light source based at least in part on a predefined brightness value. The predefined brightness value may correspond to an absolute change in brightness (e.g., a specific number of lumens by which the light emitted is to be reduced), a relative change in brightness in relation to a specific brightness value (e.g., a specific percentage of a maximum light, such reducing the brightness by 5% of the maximum number of lumens for which the light source is rated, or reducing the brightness by 5% in relation to light emitted when the wearable lamp is operating in a normal mode where light is not being regulated based on temperature), a relative change in brightness in relation to a brightness value at which the system is currently operating (e.g., before the reduction of the light). Various brightness values may be implemented, and the various brightness values may be configurable, such as based on user preferences. In some embodiments, the brightness values used in connection with determining an extent to reduce the brightness are determined based on a change or rate of change that is perceptible to the human eye or determined based on changes that are disruptive to the task at hand (e.g., that would disrupt a surgeon during a surgical procedure).

According to various embodiments, the system stores a mapping of predefined temperature thresholds to corresponding predefined brightness values to be used to adjust the brightness of the light source. In response to determining that the detected operating temperature exceeds a particular predefined temperature threshold, the system queries the mapping to determine the corresponding predefined brightness value (e.g., the system determines an extent by which the brightness is to be changed/reduced).

At 2340, a determination is made as to whether process 2300 is complete. In some embodiments, process 2300 is determined to be complete in response to a determination that the wearable lamp is turned off, the wearable lamp is no longer configured to be controlled based on orientation data, a user indicates that process 2300 is to be paused or stopped, etc. In response to a determination that process 2300 is complete, process 2300 ends. In response to a determination that process 2300 is not complete, process 2300 returns to 2310.

Although process 2300 is described in the context of adjusting brightness if a detected operating temperature exceeds a predefined temperature threshold, various embodiments may similarly compare the detected operating temperature to a predefined temperature threshold and correspondingly increase the brightness in response to determining that the detected operating temperature is less than a predefined temperature threshold. Accordingly, as the temperature of the wearable lamp decreases (e.g., by reducing power to the light source) the system may gradually increase the brightness level.

Figure 24:
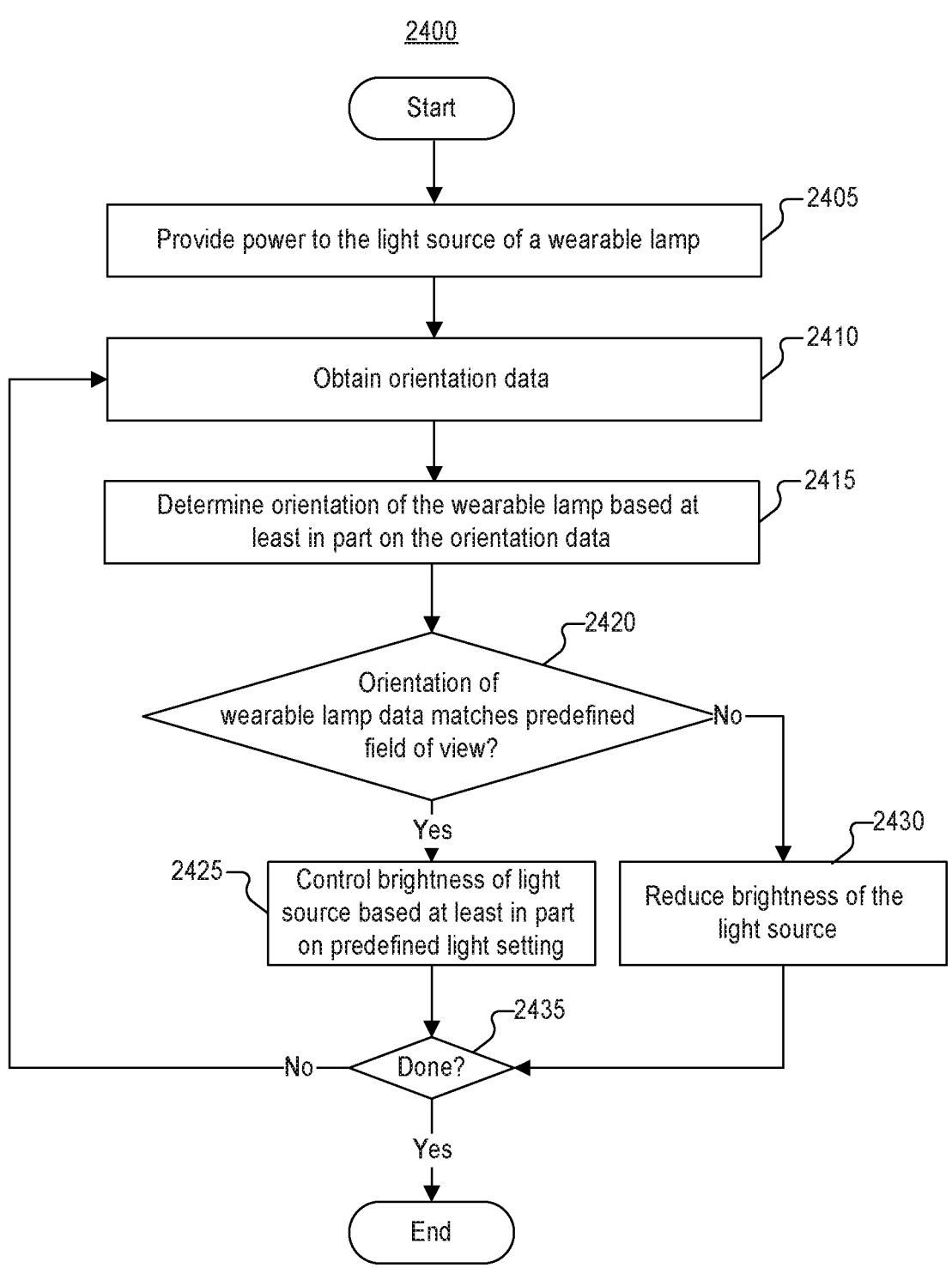
FIG. 24 illustrates a flow diagram of a method for controlling a wearable lamp based at least in part on an orientation of the wearable lamp according to various embodiments.

FIG. 24 illustrates a flow diagram of a method for controlling a wearable lamp based at least in part on an orientation of the wearable lamp according to various embodiments. In various embodiments, process 2400 is implemented by a processor comprised in the wearable lamp.

At 2405, power is provided to the light source of a wearable lamp. In some embodiments, the system provides power to the light source in response to the wearable lamp being turned on.

At 2410, orientation data is obtained. In some embodiments, the system obtains the orientation data from one or more sensors or a navigational system (e.g., a surgical navigation system) with which the system (e.g., the wearable lamp) is registered.

As an example, the system comprises an accelerometer that the system uses to collect orientation data, such as an extent to which the wearable lamp is tilted.

As another example, the surgical navigation system tracks orientation of the wearable lamp (e.g., and thus the system may track the surgical field of view) and uses the orientation as feedback. The surgical navigation system may communicate orientation data to the wearable lamp, such as via an application running on a smartphone that is connected to the wearable lamp.

At 2415, the system determines an orientation of the wearable lamp based at least in part on the orientation data. In response to obtaining the orientation data, the system determines the orientation of the wearable lamp. As an example, the system determines an absolute orientation of the wearable lamp. As another example, the system determines a relative orientation of the wearable lamp (e.g., an extent to which an orientation has changed from an earlier measurement, such as a determination of whether the wearable lamp has been tilted down or tilted up).

At 2420, the system determines whether the orientation of the wearable lamp matches a predefined field of view. The predefined field of view may be defined based on a user setting, such as based on performing an initialization of the wearable lamp after being turned on or based on a surgical room configuration or predetermined posture of a user (e.g., as detected by a surgical navigation system, etc.). In some embodiments, the predefined field of view comprises a surgeon perspective directed to a patient anatomy. As an example, the system uses the orientation data in connection with determining whether the wearable lamp is directed in a particular direction (e.g., such that a surgeon is looking to the patient anatomy). As another example, the system uses the orientation data in connection with determining whether the wearable lamp is tilted upwards, such as in the case that a surgeon looks up from the patient anatomy to view a patient film or chart.

In response to determining that the orientation of the wearable lamp matches a predefined field of view at 2420, process 2400 proceeds to 2425 at which the brightness of the light source is controlled based at least in part on a predefined light setting. Conversely, in response to determining that the orientation of the wearable lamp does not match a predefined field at 2420, process 2400 proceeds to 2430 at which the brightness of the light source is reduced.

In some embodiments, in response to determining that a wearable lamp is moved to be oriented such that the user's field of view is not consistent with the view of the patient anatomy (e.g., in the case that the surgeon has looked up to read a patient chart, film, or surgical plan), the system reduces the brightness of the light source. When a surgeon is attempting to read patient chart, film, or surgical plan, a wearable lamp generally causes glare which makes reading such chart, film, or surgical plan more difficult. Conversely, in response to determining that the wearable lamp is moved to be oriented consistent with a field of view directed to a patient anatomy (e.g., in the case that the surgeon is looking down towards the patient anatomy or surgical area, the system may turn on the light source or increase the brightness of the light source.

In some embodiments, the system toggles the light source on/off based on whether the wearable lamp is oriented in a first orientation (e.g., when the surgeon's field of view is directed to the surgical site), or the wearable lap is not oriented in the first orientation (e.g., when the surgeon has looked up from the surgical site).

In some embodiments, the system changes a brightness of the light source based on whether the wearable lamp is oriented in a first orientation (e.g., when the surgeon's field of view is directed to the surgical site), or the wearable lamp is not oriented in the first orientation (e.g., when the surgeon has looked up from the surgical site). For example, when the surgeon's field of view is directed to the surgical site and the surgeon looks up from the surgical site, the system may control the wearable lamp to reduce a brightness of the light source. As another example, when the surgeon's field of view is directed away from the surgical site and the surgeon subsequently looks towards the surgical site, the system may control the wearable lamp to increase a brightness of the light source.

In some embodiments, changing (e.g., increasing or decreasing) the brightness of the light source includes changing the light brightness by a predefined brightness value. As an example, the predefined brightness value may be a predefined number of lumens by which the light source brightness is to be changed. As another example, the predefined brightness value may be a predefined percentage (e.g., the brightness is changed by a predefined percentage of a current brightness before the orientation is changed, or by a predefined percentage of a brightness threshold such as a maximum brightness of the light source). As an illustrative example, when the surgeon's field of view is directed to the surgical sight, the light source brightness may be 75% of the maximum brightness of the light source. When the surgeon's field of view changes (e.g., when the orientation of the wearable lamp is changed), the system may decrease the brightness by 40% from the current brightness (e.g., the new brightness is 40% of the 75% of the maximum brightness). As another illustrative example, when the surgeon's field of view is directed to the surgical sight, the light source brightness may be 400 lumens. When the surgeon's field of view changes (e.g., when the orientation of the wearable lamp is changed), the system may decrease the brightness by 200 lumens or may set the brightness of the light source to a predefined brightness level (e.g., sets the brightness at 100 lumens, etc.).

In some embodiments, the predefined field of view is the surgical site. In response to determining that the wearable lamp is directed to the predefined field of view, the system controls the wearable lamp to operate at a brightness such as a normal operating brightness, or a last used brightness when the surgeon previously was viewing the surgical site (e.g., the brightness of the wearable lamp before the surgeon looked away from the surgical site).

At 2435, a determination is made as to whether process 2400 is complete. In some embodiments, process 2400 is determined to be complete in response to a determination that the wearable lamp is turned off, the wearable lamp is no longer configured to be controlled based on orientation data, a user indicates that process 2400 is to be paused or stopped, etc. In response to a determination that process 2400 is complete, process 2400 ends. In response to a determination that process 2400 is not complete, process 2400 returns to 2410.

Figure 25:
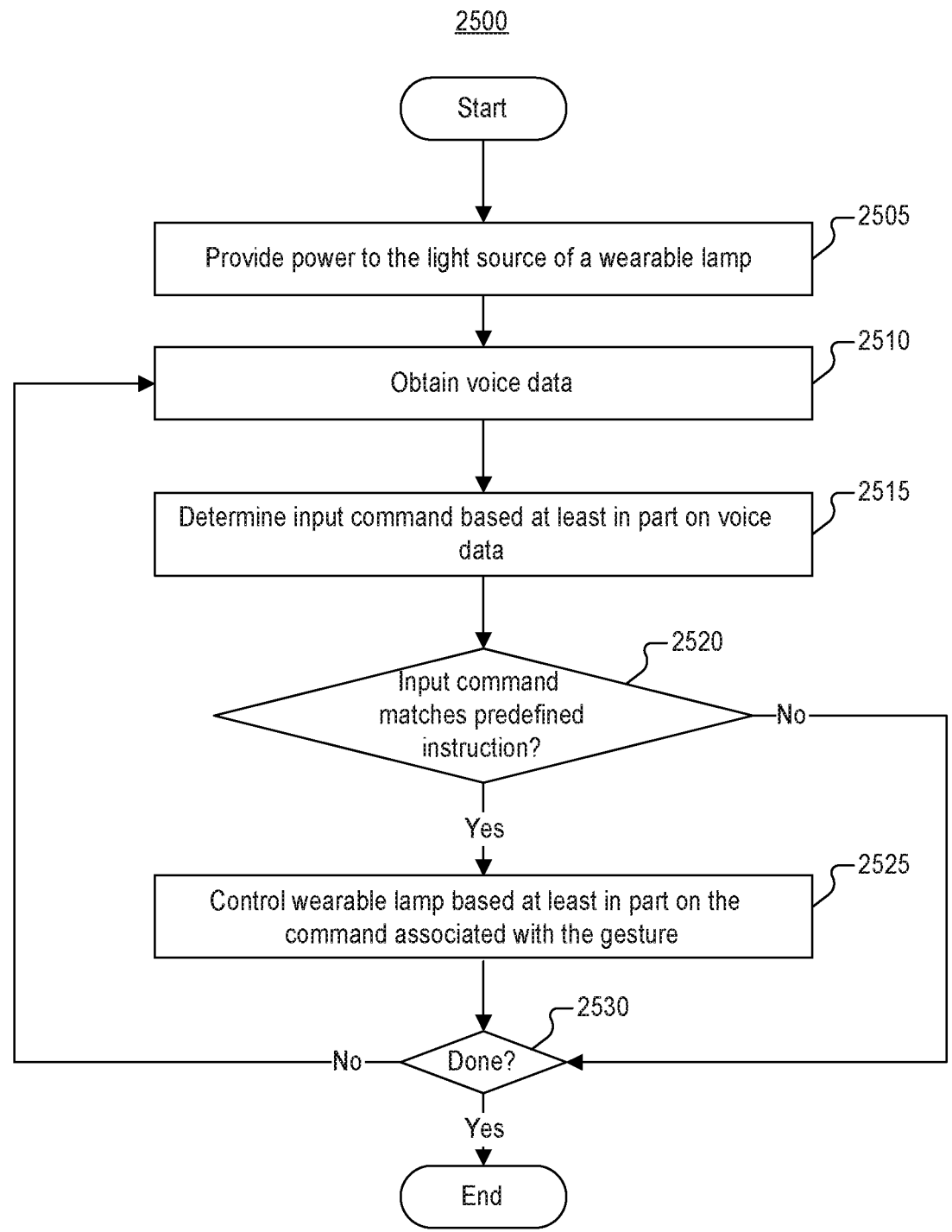
FIG. 25 illustrates a flow diagram of a method for controlling a wearable lamp based at least in part on voice data according to various embodiments.

FIG. 25 illustrates a flow diagram of a method for controlling a wearable lamp based at least in part on voice data according to various embodiments. In various embodiments, process 2500 is implemented by a processor comprised in the wearable lamp.

At 2505, power is provided to the light source of a wearable lamp. In some embodiments, the system provides power to the light source in response to the wearable lamp being turned on.

At 2510, voice data is obtained. In some embodiments, the system obtains the voice data from an onboard microphone. The voice data may comprise a voice command spoken/input by the user (e.g., a surgeon). For example, a surgeon may say "increase brightness" and the system obtains such voice data.

At 2515, the system determines an input command based at least in part on the voice data. The system analyzes the voice data to determine the input command comprised in the voice data. In some embodiments, the system determines the input command comprised in the voice data by querying a machine learning model (or other speech recognition process) based on the voice data.

At 2520, the system determines whether the input command matches a predefined instruction. Examples of predefined instructions include: turn-on the light source; turn off the light source; increase the brightness by a predefined brightness value (e.g., number of lumens or percentage of brightness); decrease the brightness by a predefined brightness value; change a color of light; perform a strobing of the light source; etc. Various other predefined instructions may be implemented.

In response to determining that the input command matches a predefined instruction at 2520, process 2500 proceeds to 2525 at which the wearable lamp is controlled based at least in part on the input command. As an example, the system uses the input command to control the wearable lamp.

In some embodiments, the system stores a mapping of input commands to instructions to use to control the light source. For example, the system may store a mapping of the predefined instruction for turning-off the light source to a predefined light control instruction for stopping providing power to the light source.

Conversely, in response to determining that the input command does not match a predefined instruction at 2520, process 2500 proceeds to 2530.

At 2530, a determination is made as to whether process 2500 is complete. In some embodiments, process 2500 is determined to be complete in response to a determination that the wearable lamp is turned off, the wearable lamp is no longer configured to be controlled based on gesture data, a user indicates that process 2500 is to be paused or stopped, etc. In response to a determination that process 2500 is complete, process 2500 ends. In response to a determination that process 2500 is not complete, process 2500 returns to 2510.

Figure 26:
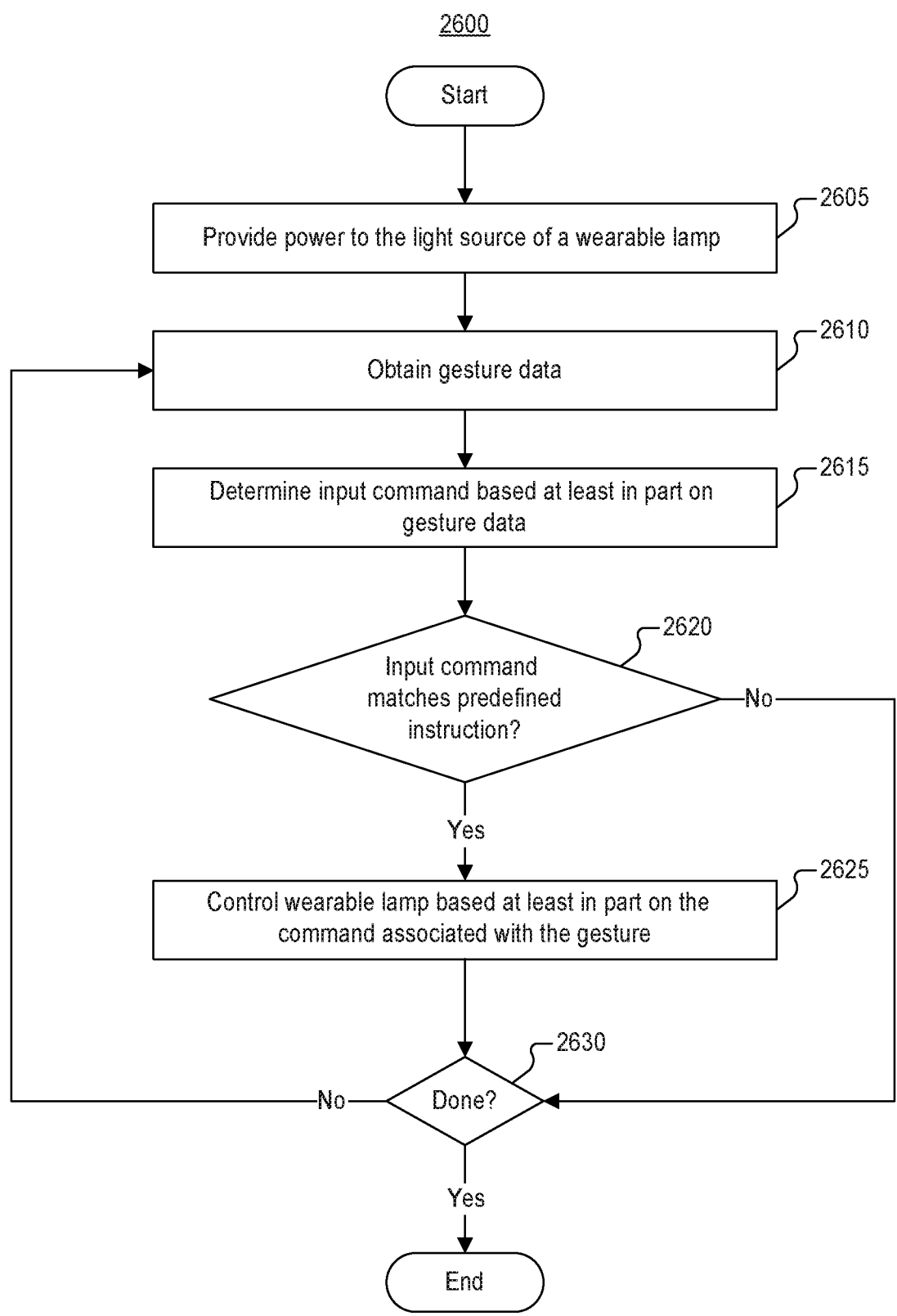
FIG. 26 illustrates a flow diagram of a method for controlling a wearable lamp based at least in part on a gesture according to various embodiments.

FIG. 26 illustrates a flow diagram of a method for controlling a wearable lamp based at least in part on a gesture according to various embodiments. In various embodiments, process 2600 is implemented by a processor comprised in the wearable lamp.

At 2605, power is provided to the light source of a wearable lamp. In some embodiments, the system provides power to the light source in response to the wearable lamp being turned on.

At 2610, gesture data is obtained. In some embodiments, the system obtains the gesture data based at least in part on information obtained by one or more sensors comprised in the wearable lamp. In some embodiments, the system obtains the gesture data by receiving an indication of a detected gesture from another device that is operatively connected to the wearable lamp. For example, a surgical navigation system may detect a surgeon's gesture and provide the gesture data to the wearable lamp, such as via an application running on a smartphone connected to the wearable lamp. Examples of gesture data includes: an indication that a surgeon is making a fist; an indication that a surgeon is waving its hand; an indication that the surgeon is holding up a certain number of fingers; an indication that the surgeon configures its fingers in a particular manner, etc. Various other gestures may be implemented. For example, gesture data may be predefined by a user. The user may train the wearable lamp to store a mapping of a particular gesture to a particular function/command.

At 2615, the system determines an input command based at least in part on the gesture data. In some embodiments, the system stores a mapping of gestures to input commands. In response to determining the detected gesture, the system queries the mapping of gestures to input commands to determine the input command matching the detected gesture.

At 2620, the system determines whether the input command matches a predefined instruction. In some embodiments, the system stores a mapping of input commands to predefined instructions. As an example, an input command to increase brightness may be mapped to a predefined instruction to increase the brightness by a particular number of lumens (e.g., by 50 lumens), or to increase the brightness by a particular percentage (e.g., by 5%), etc. The system may determine whether the input command has a corresponding predefined instruction. As an example, the system may determine that the input command is not mapped to a particular predefined instruction, such as in the case that the user has not registered the input command with a desired outcome.

In response to determining that the input command matches a predefined instruction at 2620, process 2600 proceeds to 2625 at which the wearable lamp is controlled based at least in part on the input command. Conversely, in response to determining that the input command does not match a predefined instruction at 2620, process 2600 proceeds to 2630.

At 2630, a determination is made as to whether process 2600 is complete. In some embodiments, process 2600 is determined to be complete in response to a determination that the wearable lamp is turned off, the wearable lamp is no longer configured to be controlled based on gesture data, a user indicates that process 2600 is to be paused or stopped, etc. In response to a determination that process 2600 is complete, process 2600 ends. In response to a determination that process 2600 is not complete, process 2600 returns to 2610.

FIG. 27 illustrates a flow diagram of a method for providing surgical feedback based at least in part on an orientation of a wearable lamp according to various embodiments. In various embodiments, process 2700 is implemented by a computer system, such as a surgical navigational system.

At 2705, the system detects light from a light source of a wearable lamp. In some embodiments, the system performs an initialization/alignment of the wearable element by detecting light emitted from a light source, or light reflected by one or more reflectors in the surgical site (e.g., a light reflector(s) comprised in, or mounted on, the wearable lamp).

At 2710, alignment of the wearable lamp is registered. In some embodiments, the alignment of the wearable lamp is registered when the wearable lamp is directed to a particular location. For example, a user may provide an input to the wearable lamp when the wearable lamp is pointing at a target in the surgical room. The wearable lamp may communicate the indication of the user input, and the system may register the alignment of the wearable lamp.

At 2715, the system detects light reflected from one or more reflective markers on the wearable lamp. After registration of alignment of the wearable lamp, the system monitors light reflected from the one or more reflective markers to determine the field of view of the surgeon. For example, the system determines a location and orientation of the wearable lamp in relation to the surgical room (e.g., in relation to the surgical site, or patient anatomy).

At 2720, an orientation of the wearable lamp is determined. In some embodiments, the system determines orientation of the wearable lamp based at least in part on the detected light reflected from the one or more reflective markers on the wearable lamp.

At 2725, surgical feedback is configured based at least in part on the orientation of the wearable lamp and a surgical plan. In some embodiments, in response to determining an orientation of the wearable lamp, the system provides surgical feedback (e.g., to the surgeon) based on the orientation of the wearable lamp. For example, in response to detecting that the orientation of the wearable lamp corresponds to the surgeon viewing a chart, film, or surgical plan, the system may annotate the chart/film, such as to include (e.g., as an overlay) a planned/projected surgical path or trajectory. As another example, in response to detecting that the wearable lamp is re-oriented such that the surgeon's field of view if the surgical site, the system may provide a surgical feedback when the wearable lamp/line of sight is aligned with a proposed surgical target and trajectory. The system may provide the surgical feedback as a sound, or communicating an indication to an application integrated with the wearable lamp (e.g., an application running on a smartphone connected to the wearable lamp.

At 2730, the surgical feedback is provided. In some embodiments, the system provides the surgical feedback based on configuring a user interface and causing the user interface to be displayed. In some embodiments, the system provides the surgical feedback based at least in part on configuring an instruction for controlling the wearable lamp and communicating the instruction to the wearable lamp or integrated software associated with the wearable lamp (e.g., a phone app running on a phone connected to the wearable lamp). Examples of surgical feedback include: modifying a perspective of patient films/scanned image (e.g., to correspond to the surgical perspective associated with the orientation of the wearable lamp), annotating the patient films/scanned image with one or more recommendations (e.g., highlighting a proposed target for surgical intervention, drawing a trajectory on the patient films/scanned image), controlling the wearable lamp (e.g., modifying a brightness level of the wearable lamp, modifying a color of light emitted from the wearable lamp, etc.), providing an indication that the surgeon perspective and/or line of sight is aligned with a proposed surgical target or trajectory.

At 2735, a determination is made as to whether process 2700 is complete. In some embodiments, process 2700 is determined to be complete in response to a determination that no further surgical feedback is to be provided, in response to a determination that a surgical procedure is complete, a user indicates that process 2700 is to be paused or stopped, etc. In response to a determination that process 2700 is complete, process 2700 ends. In response to a determination that process 2700 is not complete, process 2700 returns to 2715.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a nonexclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

Various examples of embodiments described herein are described in connection with flow diagrams. Although the examples may include certain steps performed in a particular order, according to various embodiments, various steps may be performed in various orders and/or various steps may be combined into a single step or in parallel.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A surgical lamp, comprising:
   a light source;
   a heat sink into which heat from the light source is transferred;
   a housing, comprising:
      a front portion configured to emit light from the light source;
      a back portion opposite the front portion;
      a thermal insulating shell substantially surrounding the heat sink; and
      a plurality of ports that enable airflow to dissipate the heat transferred to the heat sink;
   a circuit board configured to drive the light source, the circuit board disposed between the heat sink and the back portion of the housing;
   a plurality of pathways configured to direct the airflow and the heat around the circuit board; and
   a spacer connected to the heat sink,
   wherein the spacer is configured to direct the heat to an outside of the circuit board,
   wherein an inner wall of the housing comprises a plurality of flutes that at least partly define the plurality of pathways and direct the heat transferred to the heat sink towards the back portion of the housing, and
   wherein the circuit board comprises a plurality of through holes that define an additional plurality of pathways that direct the heat transferred to the heat sink towards the back portion of the housing.

2. The surgical lamp of claim 1, wherein the light source comprises a light-emitting diode (LED).

3. The surgical lamp of claim 1, wherein the heat sink comprises aluminum or an aluminum alloy.

4. The surgical lamp of claim 1, wherein a subset of the plurality of ports are disposed in the back portion of the housing, and wherein one or more of the plurality of pathways enables the heat transferred to the heat sink to dissipate through the subset of the plurality of ports.

5. The surgical lamp of claim 1, wherein the spacer comprises a thermally insulative material.

6. The surgical lamp of claim 1, wherein the spacer comprises a plurality of connection structures via which the housing contacts the spacer.

7. The surgical lamp of claim 1, wherein the circuit board comprises at least one of a microprocessor, an audio output amplifier, an accelerometer, one or more microphones, and an antenna.

8. The surgical lamp of claim 1, wherein the housing comprises a front bezel including a plurality of input vents through which air flows from an external environment and around the heat sink.

9. The surgical lamp of claim 1, wherein the light source comprises a plurality of light-emitting diodes (LEDs).

10. The surgical lamp of claim 9, wherein at least two of the LEDs are configured to emit different color light.

11. The surgical lamp of claim 1, wherein the light source is configured to have a brightness of at least 300 lumens.

12. The surgical lamp of claim 1, wherein the surgical lamp weighs less than 25 grams.

13. The surgical lamp of claim 1, wherein the surgical lamp weighs less than 20 grams.

14. The surgical lamp of claim 1, wherein the thermal insulating shell comprises a carbon-fiber composite.

15. The surgical lamp of claim 1, further comprising a mounting structure that is configured to mount the surgical lamp to eyewear worn by a user.

16. The surgical lamp of claim 1, further comprising:

a processor that is configured to control the light source based on voice input.

17. The surgical lamp of claim 16, wherein controlling the light source based on voice input includes changing a brightness of the light source.

18. The surgical lamp of claim 16, wherein:

the light source comprises a plurality of lighting elements; and controlling the light source based on voice input includes individually controlling one or more of the plurality of lighting elements.

19. The surgical lamp of claim 1, further comprising:

a processor that is configured to control the light source based at least in part on a tilt of the light source.

20. The surgical lamp of claim 1, further comprising:

a processor mounted to the circuit board; and a temperature sensor configured to detect one or more of heat at the circuit board and heat associated with one or more of the plurality of pathways;

wherein the processor is configured to regulate the light source based on the detected heat.

21. The surgical lamp of claim 1, wherein the surgical lamp is connected to a USB battery.

22. The surgical lamp of claim 21, wherein a connection between the surgical lamp and the USB battery is configured to be disposed at a back of a user's head.

23. A surgical lamp-of claim 1, comprising:

a light source;

a heat sink into which heat from the light source is transferred;

a housing, comprising:

a front portion configured to emit light from the light source;

a back portion opposite the front portion;

a thermal insulating shell substantially surrounding the heat sink; and a plurality of ports that enable airflow to dissipate the heat transferred to the heat sink;

a circuit board configured to drive the light source, the circuit board disposed between the heat sink and the back portion of the housing; and a plurality of pathways configured to direct the airflow and the heat around the circuit board, wherein the light source is configured to have a brightness of at least 250,000 LUX at a working distance of 13 inches.

24. A surgical lamp, comprising:

a light source;

a housing;

a heat sink into which heat from the light source is transferred;

a spacer connected to the heat sink; and a circuit board disposed behind the heat sink, wherein the spacer is configured to direct the heat to an outside of the circuit board, wherein the housing includes a thermal insulating shell substantially surrounding the heat sink and a plurality of ports that enable airflow to dissipate the heat transferred to the heat sink, wherein an inner wall of the housing comprises a plurality of flutes that at least partly define a first plurality of pathways that direct the heat transferred to the heat sink towards a back of the housing, and wherein the circuit board comprises a plurality of through holes that define a second plurality of pathways that direct the heat transferred to the heat sink towards the back of the housing.

* * * * *